(12) United States Patent
Saint-Remy et al.

(10) Patent No.: US 8,293,234 B2
(45) Date of Patent: *Oct. 23, 2012

(54) ANTIBODIES WHICH BIND AND INHIBIT BLOOD FACTOR VIII

(75) Inventors: Jean-Marie Saint-Remy, Grez-Doiceau (BE); Marc Jacquemin, Sart-Bernard (BE)

(73) Assignee: Life Sciences Research Partners, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,478

(22) Filed: Mar. 29, 2010

(65) Prior Publication Data

US 2010/0266586 A1 Oct. 21, 2010

Related U.S. Application Data

(63) Continuation of application No. 10/566,851, filed as application No. PCT/BE2004/000118 on Aug. 16, 2004, now Pat. No. 7,785,594.

(30) Foreign Application Priority Data

Aug. 14, 2003 (GB) .................................. 0319118.6
Aug. 18, 2003 (GB) .................................. 0319345.5

(51) Int. Cl.
*A61K 39/395* (2006.01)
(52) U.S. Cl. ............... 424/133.1; 424/141.1; 424/145.1; 514/13.7; 514/14.3; 514/14.9; 530/387.3; 530/388.1; 530/388.25
(58) Field of Classification Search ........................ None
See application file for complete search history.

(56) References Cited

U.S. PATENT DOCUMENTS

| | | | |
|---|---|---|---|
| 4,451,454 | A | 5/1984 | Wong |
| 5,545,403 | A | 8/1996 | Page |
| 5,545,404 | A | 8/1996 | Page |
| 5,545,405 | A | 8/1996 | Page |
| 5,602,015 | A | 2/1997 | Sudhir |
| 5,714,350 | A | 2/1998 | Co et al. |
| 5,744,446 | A | 4/1998 | Lollar et al. |
| 6,005,091 | A | 12/1999 | Blackburn et al. |
| 6,127,337 | A | 10/2000 | Konishi et al. |
| 6,210,675 | B1 | 4/2001 | Highfield et al. |
| 6,881,408 | B1 | 4/2005 | Heinrich et al. |
| 6,984,649 | B1 | 1/2006 | Murata et al. |
| 6,989,401 | B2 | 1/2006 | Maeda et al. |
| 7,008,962 | B2 | 3/2006 | Palovich et al. |
| 7,067,313 | B1 | 6/2006 | Jacquemin et al. |
| 7,214,785 | B2 | 5/2007 | Nakashima et al. |
| 7,785,594 | B2 | 8/2010 | Saint-Remy |
| 7,829,085 | B2 | 11/2010 | Jacquemin |
| 2001/0018052 | A1 | 8/2001 | Feuerstein |
| 2002/0182208 | A1 | 12/2002 | Page et al. |
| 2003/0035799 | A1 | 2/2003 | Page et al. |
| 2003/0175268 | A1 | 9/2003 | Saint-Remy et al. |
| 2004/0120951 | A1 | 6/2004 | Nakashima et al. |
| 2004/0228857 | A1 | 11/2004 | Page et al. |
| 2006/0115474 | A1 | 6/2006 | Jacquemin |
| 2006/0292149 | A1 | 12/2006 | Saint-Remy et al. |
| 2008/0206254 | A1 | 8/2008 | Jacquemin et al. |
| 2010/0266586 | A1 | 10/2010 | Saint-Remy |
| 2010/0272715 | A1 | 10/2010 | Saint-Remy |
| 2010/0285021 | A1 | 11/2010 | Jacquemin |
| 2011/0070226 | A1 | 3/2011 | Saint-Remy |

FOREIGN PATENT DOCUMENTS

| | | |
|---|---|---|
| EP | 0 822 255 A2 | 2/1998 |
| EP | 1222929 A2 | 7/2002 |
| EP | 1396539 A1 | 3/2004 |
| EP | 1706079 A | 2/2005 |
| EP | 1910420 | 2/2007 |
| EP | 1194528 B1 | 3/2007 |
| WO | WO 96/27010 A1 | 9/1996 |
| WO | WO 97/26010 A1 | 7/1997 |
| WO | WO 99/58680 | 11/1999 |
| WO | WO 01/04269 A1 | 1/2001 |
| WO | WO 02/101040 | 12/2002 |
| WO | WO 03/048328 A2 | 6/2003 |
| WO | WO 2005/016455 A2 | 2/2005 |
| WO | WO 2005/046583 A2 | 5/2005 |
| WO | WO 2007/017154 A2 | 2/2007 |

OTHER PUBLICATIONS

Alberts et al., Molecular Biology of the Cell, 3rd edition, 1994, pp. 589-591.*
Jefferis, R. Trends Pharmacol Sci. Jul. 2009;30(7):356-62. Epub Jun. 22, 2009.*
Batlle et al, (1997), "Alloantibody from a patient with severe von Willebrand disease inhibits von Willebrand factor-FVIII interaction", Ann. Hematol. 75, 111-115.
Beers et al, (1999), "Bacteremia and septic shock in the Merck Manual of Diagnosis and Therapy", eds. Merck Research Laboratories, pp. 1143-1147.
Begany, (2000), "Monoclonal Antibodies improves sepsis", Pulmonary Reviews. com 5.
Cobb et al, (1984), "Septic polyarthritis in a hemophiliac", J. Rheumatol. 11, 87-89.
Endo et al, (1995), "Glycosylation of the variable region of immunoglobulin G—site specific maturation of the sugar chains", Mol. Immunol. 32, 931-940.
Ferenz et al, (1989), "Sepsis due to an infected pseudocyst of hemophilia. A case report", Clin. Orthop. Relat Res. 254-257.
Freeman et al, (1999), "The role of inflammation in sepsis and septic shock: a meta-analysis of both clinical and preclinical trials of anti-inflammatory therapies", In Inflammation: Basic Principles and Clinical Correlates, J.I.Gallin and R.Snyderman, eds. (Philadelphia: Lippincott Williams & Wilkins), pp. 965-975.

(Continued)

*Primary Examiner* — Michael Szperka
(74) *Attorney, Agent, or Firm* — Nixon & Vanderhye P.C.

(57) ABSTRACT

The present invention discloses inhibitory antibodies against Factor VIII with modified glycosylation, either by enzymatic deglycosylation or by site directed mutagenesis. Said antibodies with modified glycosylation have equal affinity for FVIII but show different inhibiting properties. The use of one or a mixture of said antibodies allow modulation of the inhibition of factor VIII to levels between 40 and 95%. The present invention further discloses pharmaceutical compositions comprising inhibitory antibodies against Factor VIII with modified glycosylation, combinations of these antibodies and methods for treating haemostasis disorders using said antibodies and antibody mixtures.

3 Claims, 14 Drawing Sheets

OTHER PUBLICATIONS

Gawry et al, (1982)", Inactivation of factor VIII coagulant activity by two different types of human antibodies", Blood 60, 1103-1109.

Gilles et al, (1993), "Anti-factor VIII antibodies of hemophiliac patients are frequently directed towards nonfunctional determinants and do not exhibit isotypic restriction", Blood 82, 2452-2461.

Gilles et al, (1998), "The Arg 2150 His mutation within the factor VIII C1 domain eliminates a B cell epitope that is present only on factor VIII-von Willebrand factor complexes", Blood 92, 710.

Gilles et al, (1994), "Healthy subjects produce both anti-factor VIII and specific anti-idiotypic antibodies". J. Clin. Invest 94, 1496-1505.

Ingerslev et al, (1988), "Applications of immunoperoxidase techniques in specificity testing of monoclonal antibodies (Mabs) against von Willebrand factor (vWf)", Clin Chim. Acta 174, 65-81.

Jacquemin et al, (2000), "A human antibody directed to the factor VIII C1 domain inhibits factor VIII cofactor activity and binding to von Willebrand factor", Blood 95, 156-163.

Jacquemin et al, (1998), "Mechanism and kinetics of factor VIII inactivation: study with an IgG4 monoclonal antibody derived from a hemophilia A patient with inhibitor", Blood 92, 496-506.

Jacquemin et al", Glycosylation of a type 2 factor VIII inhibitor determines its maximum level of FVIII inhibition", Blood 102[11], 163a. Nov. 6, 2003.

Janeway et al, (1997),"The interaction of the antibody molecule with specific antigen", In Immunobiology. The Immune System in Health and Disease., eds. Current Biology Ltd., Garland Publishing Inc., p. 3:7-3:11.

Janeway et al, (2005), "Germinal center B cells undergo V-region somatic hypermutation,and cells with mutations that improve affinity for antigen are selected" In Immunobiology. The Immune System in Health and Disease., eds. Garland Science Publishing, pp. 379-381.

Kallas et al, (2002), "Epitope specificity of anti-FVIII antibodies during immune tolerance therapy with factor VIII preparation containing von Willebrand factor", Thromb. Res. 107, 291-302.

Kato et al, (1993), "Activity enhancement of a lung cancer-associated human monoclonal antibody HB4C5 by N-deglycosylation", Hum. Antibodies Hybridomas 4, 9-14.

Khurana et al, (1997), "The variable domain glycosylation in a monoclonal antibody specific to GnRH modulates antigen binding", Biochem. Biophys. Res. Commun. 234, 465-469.

Lenting et al, (1994), "Identification of a binding site for blood coagulation factor IXa on the light chain of human factor VIII", J. Biol. Chem. 269, 7150-7155.

Ly et al, (1982), "Characterization of an antibody to factor VIII in a patient with acquired hemophilia with circulating immune complexes", Scand. J. Haematol. 28, 132-140.

Martinell et al, (1985), "Peritonitis and septic shock—an evaluation of two experimental models in the rat", Eur. Surg. Res. 17, 160-166.

Near et al, (1993), "Characterization of an anti-digoxin antibody binding site by site-directed in vitro mutagenesis", Mol. Immunol. 30, 369-377.

Palmer et al, (1997), "Identification of novel factor VIII inhibitor epitopes using synthetic peptide arrays", Vox Sang. 72, 148-161.

Peerlinck et al, (1999), "Antifactor VIII antibody inhibiting allogeneic but not autologous factor VIII in patients with mild hemophilia A", Blood 93, 2267-2273.

Portolano et al, (1993), Lack of promiscuity in autoantigen-specific H and L chain combinations as revealed by human H and L chain "roulette", J. Immunol. 150, 880-887.

Price et al, (2004), "Tissue factor and tissue factor pathway inhibitor", Anaesthesia 59, 483-492.

Riedemann et al, (2003), "Anti-inflammatory strategies for the treatment of sepsis". Expert. Opin. Biol. Ther. 3, 339-350.

Rudikoff et al, (1982), "Single amino acid substitution altering antigen-binding specificity," Proc. Natl. Acad. Sci. U. S. A 79, 1979-1983.

Saint-Remy, (2000), "Hemophilia factor VIII therapy. B- and T-cell tolerance: from basic concepts to clinical practice", Haematologica 85, 93-96.

Sato et al, (1996), "Humanization of an anti-human IL-6 mouse monoclonal antibody glycosylated in its heavy chain variable region", Hum. Antibodies Hybridomas 7, 175-183.

Scandella et al, (1989), "Localization of epitopes for human factor VIII inhibitor antibodies by immunoblotting and antibody neutralization", Blood 74, 1618-1626.

Singh et al, (2002), "Antithrombotic effects of controlled inhibition of factor VIII with a partially inhibitory human monoclonal antibody in a murine vena cava thrombosis model", Blood 99, 3235-3240.

Taylor et al, (1997), "7E3 F(ab')2, a monoclonal antibody to the platelet GPIIb/IIIa receptor, protects against microangiopathic hemolytic anemia and microvascular thrombotic renal failure in baboons treated with C4b binding protein and a sublethal infusion of *Escherichia coli*", Blood 89, 4078-4084.

Wright et al, (1991), "Antibody variable region glycosylation: position effects on antigen binding and carbohydrate structure", EMBO J. 10, 2717-2723.

Yan et al, (2004), "Therapeutic effects of lysophosphatidylcholine in experimental sepsis", Nat. Med. 10, 161-167.

Yelton et al, (1995), "Affinity maturation of the BR96 anti-carcinoma antibody by codon-based mutagenesis", J. Immunol. 155, 1994-2004.

Ziegler et al, (1991), "Treatment of gram-negative bacteremia and septic shock with HA-1A human monoclonal antibody against endotoxin. A randomized, double-blind, placebo-controlled trial. The HA-1A Sepsis Study Group", N. Engl. J. Med. 324, 429-436.

Algiman et al, (1992), "Natural antibodies to factor VIII (antihemophilic factor) in healthy individuals", Proc. Natl. Acad. Sci. U. S. A 89, 3795-3799.

Amit et al, (1986), "Three-dimensional structure of an antigen-antibody complex at 2.8 A resolution", Science 233, 747-753.

Campbell, (1984)", General properties and applications of monoclonal antibodies", In Laboratory Techniques in Biochemistry and Molecular Biology. Monoclonal Antibody Technology., R.H. Burdon and P.H.Knippenberg, eds. (Amsterdam: Elsevier Science Publishers), pp. 1-4.

Chatellier et al, (1995), "Codon-based combinatorial alanine scanning site-directed mutagenesis: design, implementation, and polymerase chain reaction screening", Anal. Biochem. 229, 282-290.

Davies et al, (1996), "Affinity improvement of single antibody VH domains: residues in all three hypervariable regions affect antigen binding", Immunotechnology. 2, 169-179.

Fay et al, (1999), "Human inhibitor antibodies specific for the factor VIII A2 domain disrupt the interaction between the subunit and factor IXa", J. Biol. Chem. 274, 29826-29830.

Foster et al, (1988), "An immunogenic region within residues Val1670-Glu1684 of the factor VIII light chain induces antibodies which inhibit binding of factor VIII to von Willebrand factor", J. Biol. Chem. 263, 5230-5234.

Fukui et al, (1981), "Laboratory evidence of DIC under FEIBA treatment of a hemophilic patient with intracranial bleeding and high titre factor VIII inhibitor", Thromb. Res. 22, 177-184.

Fulcher et al, (1985), "Human factor VIII procoagulant protein. Monoclonal antibodies define precursor-product relationships and functional epitopes", J. Clin. Invest 76, 117-124.

Gilles et al, (1996), "Neutralizing antiidiotypic antibodies to factor VIII inhibitors after desensitization in patients with hemophilia A", J. Clin. Invest 97, 1382-1388.

Gilles et al, (1999), "Antibodies to idiotypes of human monoclonal anti-factor VIII (FVIII) antibodies neutralise their inhibitory activity", Blood 94, 460a.

Gilles et al, (1997), "Factor VIII inhibitors", Thromb. Haemost. 78, 641-646.

Healey et al, (1995), "Residues 484-508 contain a major determinant of the inhibitory epitope in the A2 domain of human factor VIII", J. Biol. Chem. 270, 14505-14509.

Holt et al, (2003), "Domain antibodies: proteins for therapy", Trends Biotechnol. 21, 484-490.

Jacquemin et al, (1998), "Mutation ARG2150 → HIS in the factor VIII C1 domain alters the binding of factor VIII to von Willebrand factor and is responsible for a mild hemophilia A phenotype", Blood 92, 710.

Jacquemin et al , (2003) "Glycosylation of a type 2 factor VIII inhibitor determines its maximum level of FVIII inhibition", Blood 102[11], 163a.

Kaufman et al, (1988), "Synthesis, processing, and secretion of recombinant human factor VIII expressed in mammalian cells", J. Biol. Chem. 263, 6352-6362.

Lenting et al, (1999), "The light chain of factor VIII comprises a binding site for low density lipoprotein receptor-related protein", J. Biol. Chem. 274, 23734-23739.

Lollar et al, (1994), "Inhibition of human factor VIIIa by anti-A2 subunit antibodies", J. Clin. Invest 93, 2497-2504.

Lubahn et al, (1990), "Characterization of a monoclonal anti-idiotype antibody to human anti-factor VIII antibodies", Proc. Natl. Acad. Sci. U. S. A 87, 8232-8236.

Manivel et al, (2000), "Maturation of an antibody response is governed by modulations in flexibility of the antigen-combining site", Immunity. 13, 611-620.

Muhle et al, (2004), "Epitope mapping of polyclonal clotting factor VIII-inhibitory antibodies using phage display", Thromb. Haemost. 91, 619-625.

Nystrom. (1998), "The systemic inflammatory response syndrome: definitions and aetiology", J. Antimicrob. Chemother. 41 Suppl A, 1-7.

Owens et al, (1994), "The genetic engineering of monoclonal antibodies", J. Immunol. Methods 168, 149-165.

Pratt et al, (1999), "Structure of the C2 domain of human factor VIII at 1.5 A resolution", Nature 402, 439-442.

Precup et al, (1991), "A monoclonal antibody to factor VIII inhibits von Willebrand factor binding and thrombin cleavage", Blood 77, 1929-1936.

Saenko et al, (1999)", Role of the low density lipoprotein-related protein receptor in mediation of factor VIII catabolism", J. Biol. Chem. 274, 37685-37692.

Saint-Remy et al, (1999), "Anti-idiotypic antibodies:from regulation to therapy of factor VIII inhibitors". Vox Sang. 77 (Suppl. 1), 21-24.

Shima et al, (1993), "A factor VIII neutralizing monoclonal antibody and a human inhibitor alloantibody recognizing epitopes in the C2 domain inhibit factor VIII binding to von Willebrand factor and to phosphatidylserine", Thromb. Haemost. 69, 240-246.

Spiegel et al, (2001), "Structure of a factor VIII C2 domain-immunoglobulin G4kappa Fab complex: identification of an inhibitory antibody epitope on the surface of factor VIII", Blood 98, 13-19.

Stoilova-McPhie et al, (2002), "3-Dimensional structure of membrane-bound coagulation factor VIII: modeling of the factor VIII heterodimer within a 3-dimensional density map derived by electron crystallography", Blood 99, 1215-1223.

Sultan et al, (1987), "Recovery from anti-VIII:C (antihemophilic factor) autoimmune disease is dependent on generation of antiidiotypes against anti-VIII:C autoantibodies", Proc. Natl. Acad. Sci. U. S. A 84, 828-831.

van den Brink et al, (2002), "Two classes of germline genes both derived from the V(H)1 family direct the formation of human antibodies that recognize distinct antigenic sites in the C2 domain of factor VIII", Blood 99, 2828-2834.

van den Brink et al, (2000), "Molecular analysis of human anti-factor VIII antibodies by V gene phage display identifies a new epitope in the acidic region following the A2 domain", Blood 96, 540-545.

Wilbur et al, (1983), "Rapid similarity searches of nucleic acid and protein data banks", Proc. Natl. Acad. Sci. U. S. A 80, 726-730.

Office Action dated Apr. 26, 2011, issued in connection with U.S. Appl. No. 12/732,556.

The Merck Manual of Diagnosis and Therapy, $17^{th}$ edition, Merck Research Laboratories, 1999, pp. 2816-2819.

Declaration of Marc G. Jacquemin, Ph.D. Under 37 CFR § 1.131 dated Sep. 1, 2008, filed in U.S. Appl. No. 11/298,560.

Final Decision rejection JP 509473/2001, mailed Apr. 8, 2008—Japanese text and English translation.

Restriction Requirement U.S. Appl. No. 10/566,851, mailed Dec. 24, 2009.

Response to written opinion issued to PCT/BE2004/000118, of Apr. 22, 2005.

Declaration of Marc G. Jacquemin, filed in U.S. Appl. No. 10/030,522, executed dated Apr. 15, 2005.

Shapiro et al. 2001—Hemaware 6(5), 13-16 an overview of thrombophilia.

Sawamoto et al, (1997), "Anti-factor VIII inhibitor alloantibodies recognizing the A2 domain in the human factor VIII heavy chain poorly bind to porcine factor VIII", Int. J. Hematol. 65, 151-158.

International Preliminary Report on Patentability for PCT/BE2004/000118, dated Dec. 2, 2005.

International Search Report for PCT/BE2004/000118, mailed Feb. 2, 2005.

Merck Manual of Diagnosis and Disease, 17th Ed., Beers et al (Eds.), Merck Research Laboratories, Whitehouse, NJ, pp. 1143-1147 (1999).

Written Opinion for PCT/BE2004/000118 mailed Feb. 2, 2005.

Office Action issued in connection with U.S. Appl. No. 11/298,560, dated Jul. 30, 2009.

Office Action issued in connection with U.S. Appl. No. 11/298,560, dated Feb. 24, 2010.

Official Communication issued in connection with European Patent Application No. 04 761 479.7, dated Mar. 26, 2010.

Official Communication issued in connection with European Patent Application No. 02 447 005.6, dated Jun. 5, 2009.

Official Communication issued in connection with Canadian Patent Application No. 2,381,125, dated May 5, 2009.

Official Communication issued in connection with European Patent Application No. 04 761 479.7, dated May 24, 2011.

* cited by examiner

Krix-1 Variable heavy chain (SEQ ID NO: 1 and 2)

```
1/1                                      31/11
ATG GAC TGG ACC TGG AGG ATC CTC TTC TTG GTG GCA GCA GCC ACA GGA GCC CAC TCC CAG
 M   D   W   T   W   R   I   L   F   L   V   A   A   A   T   G   A   H   S   Q
<---------------------------- Leader peptide ---------------------------->

61/21                                    91/31
GTG CAA CTG GTG CAA TCT GGG GCT GAG GTG AAG AAG CCT GGG GCC TCA GTG AAG GTC TCC
 V   Q   L   V   Q   S   G   A   E   V   K   K   P   G   A   S   V   K   V   S

121/41              47      49   151/51
TGC AAG ACC TCT GGA TAC AAC TTC ACC GGC TAC TCT GCT TCT GGA CAT ATC TTC ACC GCC
 C   K   T   S   G   Y   N   F   T   G   Y   S   A   S   G   H   I   F   T   A
                         *       *
              <-----------------------------------CDR1 (SEQ ID NO:33)--------

181/61                                   211/71
TAC TCT GTG CAC TGG GTG CGA CAG GCC CCT GGA CAA GGG CTT GAG TGG ATG GGA AGG ATC
 Y   S   V   H   W   V   R   Q   A   P   G   Q   G   L   E   W   M   G   R   I
-------------->                                                     <-------

241/81                                   271/91
AAC CCT AAC AGT GGT GCC ACA GAC TAT GCA CAT AAA TTT CAG GGC AGG GTC ACC ATG TCC
 N   P   N   S   G   A   T   D   Y   A   H   K   F   Q   G   R   V   T   M   S
----------- CDR2 (SEQ ID NO:34) ------------------------>

301/101                                  331/111
AGG GAC ACG TCC ATC AGC ACA GCC TAC ATG GAA CTG AGC AGG CTG ACA TCT GAC GAC ACG
 R   D   T   S   I   S   T   A   Y   M   E   L   S   R   L   T   S   D   D   T

361/121                                  391/131
GCC ATG TAT TAC TGT GCG AGA GCC GAC AAC TAT TTC GAT ATT GTG ACT GGC TAT ACT TCT
 A   M   Y   Y   C   A   R   A   D   N   Y   F   D   I   V   T   G   Y   T   S
                         <-------------------- CDR3 (SEQ ID NO:35) ---

421/141                                  451/151
CAT TAC TTT GAC TAC TGG GGC CGG GGA ACC CTG GTC ACC GTC TCC TCA GCC TCC ACC AAG
 H   Y   F   D   Y   W   G   R   G   T   L   V   T   V   S   S   A   S   T   K
------------------>

481/161
GGC CCA TCG GTC TTC C
 G   P   S   V   F
```

Figure 17

Krix-1 Variable light chain (SEQ ID NO: 3 and 4)

```
1/1                                           31/11
ATG GAA ACC CCA GCT CAG CTT CTC TTC CTC CTG CTA CTC TGG CTC CCA GAT ACC ACC GGA
 M   E   T   P   A   Q   L   L   F   L   L   L   W   L   P   D   T   T   G
<------------------------------ Leader ------------------------------>

61/21                                         91/31
GAA ATT GTG TTG ACG CAG TCT CCA GGC ACC CTG TCT TTG TCT CCA GGG GAA AGA GCC ACC
 E   I   V   L   T   Q   S   P   G   T   L   S   L   S   P   G   E   R   A   T

121/41                                        151/51
CTC TCC TGC AGG GCC AGT CAG AGT GTT GCC AGC GCC TAC TTA GCC TGG TAC CAG CAA AAA
 L   S   C   R   A   S   Q   S   V   A   S   A   Y   L   A   W   Y   Q   Q   K
             <------------ CDR1 (SEQ ID NO:36) ------------>

181/61                                        211/71
CCT GGC CAG GCT CCC AGG CTC CTC ATC TAT GGT GCA TCC AGT AGG GCC ACC GAC ATC CCA
 P   G   Q   A   P   R   L   L   I   Y   G   A   S   S   R   A   T   D   I   P
                                     <--- CDR2 (SEQ ID NO:37)--->

241/81                                        271/91
CAC AGG TTC AGT GGC AGT GGG TCT GGG ACA GAC TTC ACT CTC ACC ATC AGC AGA CTG GAG
 H   R   F   S   G   S   G   S   G   T   D   F   T   L   T   I   S   R   L   E

301/101                                       331/111
CCT GAA GAT TTT GCA GTG TAC TAC TGT CAG CAA TAT GGT ACC TCA GCC TTA CTC ACT TTC
 P   E   D   F   A   V   Y   Y   C   Q   Q   Y   G   T   S   A   L   L   T   F
                                 <------- CDR3 (SEQ ID NO:38) --------->

361/121                                       391/131
GGC GGA GGG ACC AAG GTG GAG ATC AAA CGA ACT GTG GCT GCA CCA TCT GTC TTC ATC TTC
 G   G   G   T   K   V   E   I   K   R   T   V   A   A   P   S   V   F   I   F

421/141
CCG CCA TCT
 P   P   S
```

Figure 17 (continued)

scFvLE2E9VLVH Q(His) (SEQ ID 25 and 26)

```
1/1                                  31/11
atg gaa acc cca gcg cag ctt ctc ttc ctc ctg cta ctc tgg ctc cca gat acc acc gga
 M   E   T   P   A   Q   L   L   F   L   L   L   W   L   P   D   T   T   G
<--------------------- Leader peptide --------------------------------->

61/21                                91/31
gaa att gtg ttg acg cag tct cca ggc acc ctg tct ttg tct cca ggg gaa aga gcc acc
 E   I   V   L   T   Q   S   P   G   T   L   S   L   S   P   G   E   R   A   T
<---------------------------------------------------------------------------

121/41                               151/51
ctc tcc tgc agg gcc agt cag agt gtt gcc agc gcc tac tta gcc tgg tac cag caa aaa
 L   S   C   R   A   S   Q   S   V   A   S   A   Y   L   A   W   Y   Q   Q   K
---------------------------------------------------------------------------

181/61                               211/71
cct ggc cag gct ccc agg ctc ctc atc tat ggt gca tcc agt agg gcc acc gac atc cca
 P   G   Q   A   P   R   L   L   I   Y   G   A   S   S   R   A   T   D   I   P
---------------------------------------- VLJk ------------------------------

241/81                               271/91
cac agg ttc agt ggc agt ggg tct ggg aca gac ttc act ctc acc atc agc aga ctg gag
 H   R   F   S   G   S   G   S   G   T   D   F   T   L   T   I   S   R   L   E
---------------------------------------------------------------------------

301/101                              331/111
cct gaa gat ttt gca gtg tac tac tgt cag caa tat ggt acc tca gcc tta ctc act ttc
 P   E   D   F   A   V   Y   Y   C   Q   Q   Y   G   T   S   A   L   L   T   F
---------------------------------------------------------------------------

361/121                              391/131
ggc gga ggg acc aag gtg gag atc aaa cga ggt gga ggc ggt tca ggc gga ggt ggc tct
 G   G   G   T   K   V   E   I   K   R   G   G   G   G   S   G   G   G   G   S
---------------------------------------> <--------------------- Linker ---

421/141                              451/151
ggc ggt ggc gga tcg cag gta cag ctg gtg cag tct ggg gct gag gtg aag aag cct ggg
 G   G   G   G   S   Q   V   Q   L   V   Q   S   G   A   E   V   K   K   P   G
-------------------> <-----------------------------------------------------

481/161                              511/171
gcc tca gtg aag gtc tcc tgc aag acc tct gga tac caa ttc acc ggc tac tct gct tct
 A   S   V   K   V   S   C   K   T   S   G   Y   Q   F   T   G   Y   S   A   S
                                                Gln47             Thr49

541/181                              571/191
gga cat atc ttc acc gcc tac tct gtg cac tgg gtg cga cag gcc cct gga caa ggg ctt
 G   H   I   F   T   A   Y   S   V   H   W   V   R   Q   A   P   G   Q   G   L
---------------------------------------------------------------------------
```

Figure 18

```
601/201                                    631/211
gag tgg atg gga agg atc aac cct aac agt ggt gcc aca gac tat gca cat aaa ttt cag
 E   W   M   G   R   I   N   P   N   S   G   A   T   D   Y   A   H   K   F   Q
------------------------------------------ VHDJH ------------------------------

661/221                                    691/231
ggc agg gtc acc atg tcc agg gac acg tcc atc agc aca gcc tac atg gaa ctg agc agg
 G   R   V   T   M   S   R   D   T   S   I   S   T   A   Y   M   E   L   S   R
-------------------------------------------------------------------------------

721/241                                    751/251
ctg aca tct gac gac aca gcc atg tat tac tgt gcg aga gcc gac aac tat ttc gat att
 L   T   S   D   D   T   A   M   Y   Y   C   A   R   A   D   N   Y   F   D   I
-------------------------------------------------------------------------------

781/261                                    811/271
gtg act ggc tat act tct cat tac ttt gac tac tgg ggc cgg gga acc ctg gtc acc gtc
 V   T   G   Y   T   S   H   Y   F   D   Y   W   G   R   G   T   L   V   T   V
-------------------------------------------------------------------------------

841/281
tcc tca cat cat cat cat cat cat tga
 S   S   H   H   H   H   H   H   *
------>  <----- His(6)tag ----->
```

Figure 18 (continued)

RHD5 heavy chain variable region (SEQ ID NO: 29 and 30)

```
1/1                                        31/11
ATG GAC TGG ACC TGG AGG TTC CTC TTT GTG GTG GCA GCA GCT GCA GGT GTC CAG TCC CAG
 M   D   W   T   W   R   F   L   F   V   V   A   A   A   A   G   V   Q   S   Q
<-------------------------- Leader peptide -------------------------------->
61/21                                      91/31
GTG CAG CTG GTG CAG TCT GGG GCT GAG GTG AAG AAG CCC GGG TCG TCG GTG ATG GTC TCC
 V   Q   L   V   Q   S   G   A   E   V   K   K   P   G   S   S   V   M   V   S 121/41                                     151/51
TGC AAG GCT TCT GGA GGC ACC TTC AGC AGC TTT GGT ATC AGC TGG GTG CGA CAG GCC CCT
 C   K   A   S   G   G   T   F   S   S   F   G   I   S   W   V   R   Q   A   P
                    <---------------- CDR1 ---------------->

181/61                                     211/71
GGA CAA GGG CTT GAG TGG GTG GGA GGG ATC ATC CCT ATC TTT GGT ACA GCA AAC ACC GCA
 G   Q   G   L   E   W   V   G   G   I   I   P   I   F   G   T   A   N   T   A
                                    <--------------------------- CDR2 -----------

241/81                                     271/91
CGG AAC TTC CAG AAT AGA GTC ACC ATT ACC GCG GAC GAA TTC ACG AGC ACA GCC TAC ATA
 R   N   F   Q   N   R   V   T   I   T   A   D   E   F   T   S   T   A   Y   I
----------------->

301/101                                    331/111
CGA CTG AGG AGC CTG AGA TCT GAA GAT ACG GCC GTG TAT TAC TGT GTC GGC GGT CGA GAT
 R   L   R   S   L   R   S   E   D   T   A   V   Y   Y   C   V   G   G   R   D
                                                                    <-----------
361/121                                    391/131
GCC TAC AGC TTT GAT GGT TTT GAT GTC TGG GGC CAA GGG ACA ATG GTC ACC GTC TCT TCA
 A   Y   S   F   D   G   F   D   V   W   G   Q   G   T   M   V   T   V   S   S
-------- CDR3 ---------------->

421/141
GCC TCC ACC AAG GGC CCA TCG GTC TTC CCC
 A   S   T   K   G   P   S   V   F   P
<-----------constant region-----------
```

Figure 19

RHD5 Light Chain Variable Region ( SEQ ID NO: 31 And 32)

```
1/1                                           31/11
ATG GCA TGG ATC CCT CTC TTC CTC GGC GTC CTT GTT TAC TGC ACA GGA TCC GTG GCC TCC
 M   A   W   I   P   L   F   L   G   V   L   V   Y   C   T   G   S   V   A   S
<--------------------------- Leader peptide --------------------------------->

61/21                                         91/31
TCT GGG CTG ACT CAG CCA CAC TCA GTG TCC GTG TCC CCA GGA CAG ACA GCC AAC ATC ACC
 S   G   L   T   Q   P   H   S   V   S   V   S   P   G   Q   T   A   N   I   T
                                                                        *       *
121/41                                        151/51
TGC TCT AGA GAT AAG TTG GGT CAT AAA TTT GCT TCC TGG TAT CAA CAG AAG CCA GGC CAG
 C   S   R   D   K   L   G   H   K   F   A   S   W   Y   Q   Q   K   P   G   Q
         <---------------- CDR1 ------------------->

181/61                                        211/71
TCC CCT GCT CTT CTC ATC TAT CAA GAC AGC AAG CGG CCC TCA GGG ATC CCT GAG CGA TTC
 S   P   A   L   L   I   Y   Q   D   S   K   R   P   S   G   I   P   E   R   F
                         <---------- CDR2 ---------->

241/81                                        271/91
TCT GGC TCC AAC TCT GGG AAC ACA GCC ACT CTG ACC ATC AGC GGG ACC CAG GCT ATG GAT
 S   G   S   N   S   G   N   T   A   T   L   T   I   S   G   T   Q   A   M   D

301/101                                       331/111
GAG GCT GAC TAT TAC TGT CAG GCG TGG GAC AAC ACC ACT GCC GTA TTC GGC GGA GGG ACC
 E   A   D   Y   Y   C   Q   A   W   D   N   T   T   A   V   F   G   G   G   T
                 <----------------- CDR3 ----------------->
                                          *       *
361/121                                       391/131
AAG TTG ACA GTC CTA AGT CAG CCC AAG GCT GCC CCC TCG GTC ACT CTG TTC CCG CCC TCC
 K   L   T   V   L   S   Q   P   K   A   A   P   S   V   T   L   F   P   P   S
                 <----------------------constant region--------------------
```

Figure 19 (continued)

SEQUENCE LISTING

<160> NUMBER OF SEQ ID NOS: 38

<210> SEQ ID NO 1
<211> LENGTH: 496
<212> TYPE: DNA
<213> ORGANISM: Homo sapiens
<220> FEATURE:
<221> NAME/KEY: misc_feature
<223> OTHER INFORMATION: KRIX-1 heavy chain variable region
<220> FEATURE:
<221> NAME/KEY: misc_feature
<222> LOCATION: (1)..(57)
<223> OTHER INFORMATION: nucleotide sequence encoding the leader
      sequence
<220> FEATURE:
<221> NAME/KEY: misc_feature
<222> LOCATION: (133)..(192)
<223> OTHER INFORMATION: nucleotide sequence encoding CDR1
<220> FEATURE:
<221> NAME/KEY: misc_feature
<222> LOCATION: (235)..(285)
<223> OTHER INFORMATION: nucleotide sequence encoding CDR2
<220> FEATURE:
<221> NAME/KEY: misc_feature
<222> LOCATION: (382)..(435)
<223> OTHER INFORMATION: nucleotide sequence encoding CDR3

<400> SEQUENCE: 1
atggactgga cctggaggat cctcttcttg gtggcagcag ccacaggagc ccactcccag     60
gtgcaactgg tgcaatctgg ggctgaggtg aagaagcctg ggcctcagt gaaggtctcc    120 tgcaagacct ctggatacaa cttcaccggc tactctgctt ctggacatat cttcaccgcc    180
tactctgtgc actgggtgcg acaggcccct ggacaagggc ttgagtggat gggaaggatc    240
aaccctaaca gtggtgccac agactatgca cataaatttc agggcagggt caccatgtcc    300
agggacacgt ccatcagcac agcctacatg gaactgagca ggctgacatc tgacgacacg    360
gccatgtatt actgtgcgag agccgacaac tatttcgata ttgtgactgg ctatacttct    420
cattactttg actactgggg ccggggaacc ctggtcaccg tctcctcagc ctccaccaag    480
ggcccatcgg tcttcc                                                    496

<210> SEQ ID NO 2
<211> LENGTH: 165
<212> TYPE: PRT
<213> ORGANISM: Homo sapiens
<220> FEATURE:
<221> NAME/KEY: MISC_FEATURE
<223> OTHER INFORMATION: KRIX-1 heavy chain variable region
<220> FEATURE:
<221> NAME/KEY: MISC_FEATURE
<222> LOCATION: (1)..(19)
<223> OTHER INFORMATION: leader peptide
<220> FEATURE:
<221> NAME/KEY: MISC_FEATURE
<222> LOCATION: (45)..(64)
<223> OTHER INFORMATION: CDR1
<220> FEATURE:
<221> NAME/KEY: MISC_FEATURE
<222> LOCATION: (79)..(95)
<223> OTHER INFORMATION: CDR2
<220> FEATURE:
<221> NAME/KEY: MISC_FEATURE
<222> LOCATION: (128)..(145)
<223> OTHER INFORMATION: CDR3

<400> SEQUENCE: 2

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Gly Tyr Asn Phe
                35                  40                  45

Thr Gly Tyr Ser Ala Ser Gly His Ile Phe Thr Ala Tyr Ser Val His
    50                  55                  60

Trp Val Arg Gln Ala Pro Gly Gln Gly Leu Glu Trp Met Gly Arg Ile
65                  70                  75                  80

Asn Pro Asn Ser Gly Ala Thr Asp Tyr Ala His Lys Phe Gln Gly Arg
                85                  90                  95

Val Thr Met Ser Arg Asp Thr Ser Ile Ser Thr Ala Tyr Met Glu Leu
            100                 105                 110

Ser Arg Leu Thr Ser Asp Asp Thr Ala Met Tyr Tyr Cys Ala Arg Ala
        115                 120                 125

Asp Asn Tyr Phe Asp Ile Val Thr Gly Tyr Thr Ser His Tyr Phe Asp
130                 135                 140

Tyr Trp Gly Arg Gly Thr Leu Val Thr Val Ser Ser Ala Ser Thr Lys
145                 150                 155                 160

Gly Pro Ser Val Phe
                165

<210> SEQ ID NO 3
<211> LENGTH: 429
<212> TYPE: DNA
<213> ORGANISM: Homo sapiens
<220> FEATURE:
<221> NAME/KEY: misc_feature
<223> OTHER INFORMATION: KRIX-1 light chain variable region
<220> FEATURE:
<221> NAME/KEY: misc_feature
<222> LOCATION: (1)..(60)
<223> OTHER INFORMATION: nucleotide sequence encoding leader peptide
<220> FEATURE:
<221> NAME/KEY: misc_feature
<222> LOCATION: (130)..(165)
<223> OTHER INFORMATION: nucleotide sequence encoding CDR1
<220> FEATURE:
<221> NAME/KEY: misc_feature
<222> LOCATION: (211)..(231)
<223> OTHER INFORMATION: nucleotide sequence encoding CDR2
<220> FEATURE:
<221> NAME/KEY: misc_feature
<222> LOCATION: (328)..(357)
<223> OTHER INFORMATION: nucleotide sequence encoding CDR3

<400> SEQUENCE: 3
atggaaaccc cagctcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttgcc agcgcctact tagcctggta ccagcaaaaa     180
cctggccagg ctcccaggct cctcatctat ggtgcatcca gtagggccac cgacatccca     240
cacaggttca gtggcagtgg gtctgggaca gacttcactc tcaccatcag cagactggag     300
cctgaagatt ttgcagtgta ctactgtcag caatatggta cctcagcctt actcactttc     360
ggcggaggga ccaaggtgga gatcaaacga actgtggctg caccatctgt cttcatcttc     420
ccgccatct                                                             429

<210> SEQ ID NO 4
<211> LENGTH: 143
<212> TYPE: PRT
<213> ORGANISM: Homo sapiens
<220> FEATURE:
<221> NAME/KEY: MISC_FEATURE

```
<223> OTHER INFORMATION: KRIX-1 light chain variable region
<220> FEATURE:
<221> NAME/KEY: MISC_FEATURE
<222> LOCATION: (1)..(20)
<223> OTHER INFORMATION: leader peptide
<220> FEATURE:
<221> NAME/KEY: MISC_FEATURE
<222> LOCATION: (44)..(54)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(119)
<223> OTHER INFORMATION: CDR3

<400> SEQUENCE: 4

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ala Ser Ala Tyr Leu Ala Trp Tyr Gln Gln Lys Pro Gly Gln Ala
    50                  55                  60

Pro Arg Leu Leu Ile Tyr Gly Ala Ser Ser Arg Ala Thr Asp Ile Pro
65                  70                  75                  80

His Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Thr Ser Ala Leu Leu Thr Phe Gly Gly Gly Thr Lys Val Glu Ile
        115                 120                 125

Lys Arg Thr Val Ala Ala Pro Ser Val Phe Ile Phe Pro Pro Ser
    130                 135                 140

<210> SEQ ID NO 5
<211> LENGTH: 35
<212> TYPE: DNA
<213> ORGANISM: Artificial Sequence
<220> FEATURE:
<223> OTHER INFORMATION: Krix-1 heavy chain forward primer

<400> SEQUENCE: 5
cggggtaccc caccatggac tggacctgga ggatc                              35

<210> SEQ ID NO 6
<211> LENGTH: 40
<212> TYPE: DNA
<213> ORGANISM: Artificial Sequence
<220> FEATURE:
<223> OTHER INFORMATION: Krix-1 heavy chain reverse primer

<400> SEQUENCE: 6
tatggccgac gtcgactcat ttacccggag acagggagag                         40

<210> SEQ ID NO 7
<211> LENGTH: 34
<212> TYPE: DNA
<213> ORGANISM: Artificial Sequence
<220> FEATURE:
<223> OTHER INFORMATION: Krix-1 light chain forward primer

<400> SEQUENCE: 7
```

```
cccaagcttc caccatggaa accccagckc agct                                  34
```

<210> SEQ ID NO 8
<211> LENGTH: 36
<212> TYPE: DNA
<213> ORGANISM: Artificial Sequence
<220> FEATURE:
<223> OTHER INFORMATION: Krix-1 light chain reverse primer

<400> SEQUENCE: 8

```
aaacagcctc tagactaaca ctctcccctg ttgaag                                36
```

<210> SEQ ID NO 9
<211> LENGTH: 46
<212> TYPE: DNA
<213> ORGANISM: Artificial Sequence
<220> FEATURE:
<223> OTHER INFORMATION: Krix-1 forward mutagenic primer Asn47Gln

<400> SEQUENCE: 9

```
cctgcaagac ctctggatac caattcaccg gctactctgc ttctgg                     46
```

<210> SEQ ID NO 10
<211> LENGTH: 46
<212> TYPE: DNA
<213> ORGANISM: Artificial Sequence
<220> FEATURE:
<223> OTHER INFORMATION: Krix-1 reverse mutagenic primer Asn47Gln

<400> SEQUENCE: 10

```
ccagaagcag agtagccggt gaattggtat ccagaggtct tgcagg                     46
```

<210> SEQ ID NO 11
<211> LENGTH: 37
<212> TYPE: DNA
<213> ORGANISM: Artificial Sequence
<220> FEATURE:
<223> OTHER INFORMATION: Krix-1 forward mutagenic primer Thr49Ala

<400> SEQUENCE: 11

```
cctctggata caacttcgct ggctactctg cttctgg                               37
```

<210> SEQ ID NO 12
<211> LENGTH: 37
<212> TYPE: DNA
<213> ORGANISM: Artificial Sequence
<220> FEATURE:
<223> OTHER INFORMATION: Krix-1 reverse mutagenic primer Thr49Ala

<400> SEQUENCE: 12

```
ccagaagcag agtagccagc gaagttgtat ccagagg                               37
```

<210> SEQ ID NO 13
<211> LENGTH: 46
<212> TYPE: DNA
<213> ORGANISM: Artificial Sequence
<220> FEATURE:
<223> OTHER INFORMATION: Krix-1 forward mutagenic primer Asn47Glu

<400> SEQUENCE: 13

```
cctgcaagac ctctggatac gagttcaccg gctactctgc ttctgg                     46
```

<210> SEQ ID NO 14
<211> LENGTH: 46
<212> TYPE: DNA
<213> ORGANISM: Artificial Sequence

```
<220> FEATURE:
<223> OTHER INFORMATION: Krix-1 reverse mutagenic primer Asn47Glu

<400> SEQUENCE: 14
ccagaagcag agtagccggt gaactcgtat ccagaggtct tgcagg              46

<210> SEQ ID NO 15
<211> LENGTH: 46
<212> TYPE: DNA
<213> ORGANISM: Artificial Sequence
<220> FEATURE:
<223> OTHER INFORMATION: Krix-1 forward mutagenic primer Asn47Asp

<400> SEQUENCE: 15
cctgcaagac ctctggatac gacttcaccg gctactctgc ttctgg              46

<210> SEQ ID NO 16
<211> LENGTH: 46
<212> TYPE: DNA
<213> ORGANISM: Artificial Sequence
<220> FEATURE:
<223> OTHER INFORMATION: Krix-1 reverse mutagenic primer Asn47Asp

<400> SEQUENCE: 16
ccagaagcag agtagccggt gaagtcgtat ccagaggtct tgcagg              46

<210> SEQ ID NO 17
<211> LENGTH: 45
<212> TYPE: DNA
<213> ORGANISM: Artificial Sequence
<220> FEATURE:
<223> OTHER INFORMATION: scFv-KRIX-1VL forward primer

<400> SEQUENCE: 17
gtatctctcg agaaaagaga aattgtgttg acgcagtctc caggc               45

<210> SEQ ID NO 18
<211> LENGTH: 56
<212> TYPE: DNA
<213> ORGANISM: Artificial Sequence
<220> FEATURE:
<223> OTHER INFORMATION: scFv-KRIX-1VL reverse primer

<400> SEQUENCE: 18
cgccagagcc acctccgcct gaaccgcctc cacctcgttt gatctccacc ttggtc   56

<210> SEQ ID NO 19
<211> LENGTH: 56
<212> TYPE: DNA
<213> ORGANISM: Artificial Sequence
<220> FEATURE:
<223> OTHER INFORMATION: scFv-KRIX-1VH forward primer

<400> SEQUENCE: 19
caggcggagg tggctctggc ggtggcggat cgcaggtmca gctggtgcag tctggg   56

<210> SEQ ID NO 20
<211> LENGTH: 34
<212> TYPE: DNA
<213> ORGANISM: Artificial Sequence
<220> FEATURE:
<223> OTHER INFORMATION: scFv-KRIX-1VH reverse primer

<400> SEQUENCE: 20
gatctctaga tgaggagacg gtgaccaggg ttcc                           34
```

<210> SEQ ID NO 21
<211> LENGTH: 45
<212> TYPE: DNA
<213> ORGANISM: Artificial Sequence
<220> FEATURE:
<223> OTHER INFORMATION: scFv-KRIX-1VLVH with His(6)tag forward primer

<400> SEQUENCE: 21
gtatctctcg agaaaagaga aattgtgttg acgcagtctc caggc                45

<210> SEQ ID NO 22
<211> LENGTH: 40
<212> TYPE: DNA
<213> ORGANISM: Artificial Sequence
<220> FEATURE:
<223> OTHER INFORMATION: scFv-KRIX-1VLVH with His(6)tag reverse primer

<400> SEQUENCE: 22
catggtcgac tgaggagacg gtgaccaggg ttccccggcc                      40

<210> SEQ ID NO 23
<211> LENGTH: 46
<212> TYPE: DNA
<213> ORGANISM: Artificial Sequence
<220> FEATURE:
<223> OTHER INFORMATION: scFv-Asn47Gln KRIX-1VLVH(His) forward primer

<400> SEQUENCE: 23
cctgcaagac ctctggatac caattcaccg gctactctgc ttctgg               46

<210> SEQ ID NO 24
<211> LENGTH: 46
<212> TYPE: DNA
<213> ORGANISM: Artificial Sequence
<220> FEATURE:
<223> OTHER INFORMATION: scFv-Asn47Gln KRIX-1VLVH(His) reverse primer

<400> SEQUENCE: 24
ccagaagcag agtagccggt gaattggtat ccagaggtct tgcagg               46

<210> SEQ ID NO 25
<211> LENGTH: 867
<212> TYPE: DNA
<213> ORGANISM: Artificial Sequence
<220> FEATURE:
<223> OTHER INFORMATION: scFv-Asn47Gln KRIX-1VLVH(His)

<400> SEQUENCE: 25
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttgcc agcgcctact agcctggta ccagcaaaaa    180 cctggccagg ctcccaggct cctcatctat ggtgcatcca gtagggccac cgacatccca   240
cacaggttca gtggcagtgg gtctgggaca gacttcactc tcaccatcag cagactggag   300
cctgaagatt ttgcagtgta ctactgtcag caatatggta cctcagcctt actcactttc   360
ggcggaggga ccaaggtgga gatcaaacga ggtgaggcg ttcaggcgg aggtggctct   420 ggcggtggcg gatcgcaggt acagctggtg cagtctgggg ctgaggtgaa gaagcctggg   480
gcctcagtga aggtctcctg caagacctct ggataccaat tcaccggcta ctctgcttct   540
ggacatatct tcaccgccta ctctgtgcac tgggtgcgac aggcccctgg acaagggctt   600
gagtggatgg gaaggatcaa ccctaacagt ggtgccacag actatgcaca taaatttcag   660
ggcagggtca ccatgtccag ggacacgtcc atcagcacag cctacatgga actgagcagg   720
ctgacatctg acgacacagc catgtattac tgtgcgagag ccgacaacta tttcgatatt    780
gtgactggct atacttctca ttactttgac tactggggcc ggggaaccct ggtcaccgtc    840
tcctcacatc atcatcatca tcattga                                        867

<210> SEQ ID NO 26
<211> LENGTH: 288
<212> TYPE: PRT
<213> ORGANISM: Artificial Sequence
<220> FEATURE:
<223> OTHER INFORMATION: scFv-Asn47Gln KRIX-1VLVH(His)

<400> SEQUENCE: 26

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ala Ser Ala Tyr Leu Ala Trp Tyr Gln Gln Lys Pro Gly Gln Ala
        50                  55                  60

Pro Arg Leu Leu Ile Tyr Gly Ala Ser Ser Arg Ala Thr Asp Ile Pro
65                  70                  75                  80

His Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
                100                 105                 110

Gly Thr Ser Ala Leu Leu Thr Phe Gly Gly Gly Thr Lys Val Glu Ile
            115                 120                 125

Lys Arg Gly Gly Gly Gly Ser Gly Gly Gly Gly Ser Gly Gly Gly Gly
        130                 135                 140

Ser Gln Val Gln Leu Val Gln Ser Gly Ala Glu Val Lys Lys Pro Gly
145                 150                 155                 160

Ala Ser Val Lys Val Ser Cys Lys Thr Ser Gly Tyr Gln Phe Thr Gly
                165                 170                 175

Tyr Ser Ala Ser Gly His Ile Phe Thr Ala Tyr Ser Val His Trp Val
            180                 185                 190

Arg Gln Ala Pro Gly Gln Gly Leu Glu Trp Met Gly Arg Ile Asn Pro
        195                 200                 205

Asn Ser Gly Ala Thr Asp Tyr Ala His Lys Phe Gln Gly Arg Val Thr
210                 215                 220

Met Ser Arg Asp Thr Ser Ile Ser Thr Ala Tyr Met Glu Leu Ser Arg
225                 230                 235                 240

Leu Thr Ser Asp Asp Thr Ala Met Tyr Tyr Cys Ala Arg Ala Asp Asn
                245                 250                 255

Tyr Phe Asp Ile Val Thr Gly Tyr Thr Ser His Tyr Phe Asp Tyr Trp
            260                 265                 270

Gly Arg Gly Thr Leu Val Thr Val Ser Ser His His His His His
        275                 280                 285

<210> SEQ ID NO 27
<211> LENGTH: 40
<212> TYPE: DNA
<213> ORGANISM: Artificial Sequence
<220> FEATURE:
<223> OTHER INFORMATION: CHO-scFvKRIX-1VLVHQ(His) forward primer

<400> SEQUENCE: 27

```
cccaagcttg ccgccaccat ggaaacccca gckcagcttc                          40
```

<210> SEQ ID NO 28
<211> LENGTH: 54
<212> TYPE: DNA
<213> ORGANISM: Artificial Sequence
<220> FEATURE:
<223> OTHER INFORMATION: CHO-scFvKRIX-1VLVHQ(His) reverse primer

<400> SEQUENCE: 28

```
ccggaattct caatgatgat gatgatgatg tgaggagacg gtgaccaggg ttcc          54
```

<210> SEQ ID NO 29
<211> LENGTH: 450
<212> TYPE: DNA
<213> ORGANISM: Homo sapiens
<220> FEATURE:
<221> NAME/KEY: misc_feature
<223> OTHER INFORMATION: RHD5 heavy chain variable region
<220> FEATURE:
<221> NAME/KEY: misc_feature
<222> LOCATION: (1)..(60)
<223> OTHER INFORMATION: nucleotide sequence encoding the leader peptide
<220> FEATURE:
<221> NAME/KEY: misc_feature
<222> LOCATION: (133)..(162)
<223> OTHER INFORMATION: nucleotide sequence encoding CDR1
<220> FEATURE:
<221> NAME/KEY: misc_feature
<222> LOCATION: (205)..(255)
<223> OTHER INFORMATION: nucleotide sequence encoding CDR2
<220> FEATURE:
<221> NAME/KEY: misc_feature
<222> LOCATION: (352)..(384)
<223> OTHER INFORMATION: nucleotide sequence encoding CDR3

<400> SEQUENCE: 29

```
atggactgga cctggaggtt cctctttgtg gtggcagcag ctgcaggtgt ccagtcccag    60
gtgcagctgg tgcagtctgg ggctgaggtg aagaagcccg gtcgtcggt gatggtctcc    120 tgcaaggctt ctggaggcac cttcagcagc tttggtatca gctgggtgcg acaggcccct   180
ggacaagggc ttgagtgggt gggagggatc atccctatct ttggtacagc aaacaccgca   240
cggaacttcc agaatagagt caccattacc gcggacgaat tcacgagcac agcctacata   300
cgactgagga gcctgagatc tgaagatacg gccgtgtatt actgtgtcgg cggtcgagat   360
gcctacagct ttgatggttt tgatgtctgg ggccaaggga caatggtcac cgtctcttca   420
gcctccacca agggcccatc ggtcttcccc                                    450
```

<210> SEQ ID NO 30
<211> LENGTH: 150
<212> TYPE: PRT
<213> ORGANISM: Homo sapiens
<220> FEATURE:
<221> NAME/KEY: MISC_FEATURE
<223> OTHER INFORMATION: RHD5 heavy chain variable region
<220> FEATURE:
<221> NAME/KEY: MISC_FEATURE
<222> LOCATION: (1)..(20)
<223> OTHER INFORMATION: leader peptide
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE -continued

```
<222> LOCATION: (118)..(128)
<223> OTHER INFORMATION: CDR3

<400> SEQUENCE: 30

Met Asp Trp Thr Trp Arg Phe Leu Phe Val Val Ala Ala Ala Gly
1               5                   10                  15

Val Gln Ser Gln Val Gln Leu Val Gln Ser Gly Ala Glu Val Lys Lys
            20                  25                  30

Pro Gly Ser Ser Val Met Val Ser Cys Lys Ala Ser Gly Gly Thr Phe
        35                  40                  45

Ser Ser Phe Gly Ile Ser Trp Val Arg Gln Ala Pro Gly Gln Gly Leu
    50                  55                  60

Glu Trp Val Gly Gly Ile Ile Pro Ile Phe Gly Thr Ala Asn Thr Ala
65                  70                  75                  80

Arg Asn Phe Gln Asn Arg Val Thr Ile Thr Ala Asp Glu Phe Thr Ser
                85                  90                  95

Thr Ala Tyr Ile Arg Leu Arg Ser Leu Arg Ser Glu Asp Thr Ala Val
            100                 105                 110

Tyr Tyr Cys Val Gly Gly Arg Asp Ala Tyr Ser Phe Asp Gly Phe Asp
        115                 120                 125

Val Trp Gly Gln Gly Thr Met Val Thr Val Ser Ser Ala Ser Thr Lys
    130                 135                 140

Gly Pro Ser Val Phe Pro
145                 150

<210> SEQ ID NO 31
<211> LENGTH: 420
<212> TYPE: DNA
<213> ORGANISM: Homo sapiens
<220> FEATURE:
<221> NAME/KEY: misc_feature
<223> OTHER INFORMATION: RHD5 light chain variable region
<220> FEATURE:
<221> NAME/KEY: misc_feature
<222> LOCATION: (1)..(60)
<223> OTHER INFORMATION: nucleotide sequence encoding leader peptide
<220> FEATURE:
<221> NAME/KEY: misc_feature
<222> LOCATION: (124)..(156)
<223> OTHER INFORMATION: nucleotide sequence encoding CDR1
<220> FEATURE:
<221> NAME/KEY: misc_feature
<222> LOCATION: (202)..(222)
<223> OTHER INFORMATION: nucleotide sequence encoding CDR2
<220> FEATURE:
<221> NAME/KEY: misc_feature
<222> LOCATION: (316)..(348)
<223> OTHER INFORMATION: nucleotide sequence encoding CDR3

<400> SEQUENCE: 31
atggcatgga tccctctctt cctcggcgtc cttgtttact gcacaggatc cgtggcctcc      60
tctgggctga ctcagccaca ctcagtgtcc gtgtccccag acagacagc caacatcacc     120 tgctctagag ataagttggg tcataaattt gcttcctggt atcaacagaa gccaggccag    180
tcccctgctc ttctcatcta tcaagacagc aagcggccct cagggatccc tgagcgattc    240
tctggctcca actctgggaa cacagccact ctgaccatca gcgggaccca ggctatggat    300
gaggctgact attactgtca ggcgtgggac aacaccactg ccgtattcgg cggagggacc    360
aagttgacag tcctaagtca gcccaaggct gccccctcgg tcactctgtt cccgccctcc    420

<210> SEQ ID NO 32
<211> LENGTH: 140
<212> TYPE: PRT
```

<213> ORGANISM: Homo sapiens
<220> FEATURE:
<221> NAME/KEY: MISC_FEATURE
<223> OTHER INFORMATION: RHD5 light chain variable region
<220> FEATURE:
<221> NAME/KEY: MISC_FEATURE
<222> LOCATION: (1)..(20)
<223> OTHER INFORMATION: leader peptide
<220> FEATURE:
<221> NAME/KEY: MISC_FEATURE
<222> LOCATION: (42)..(52)
<223> OTHER INFORMATION: CDR1
<220> FEATURE:
<221> NAME/KEY: MISC_FEATURE
<222> LOCATION: (68)..(74)
<223> OTHER INFORMATION: CDR2
<220> FEATURE:
<221> NAME/KEY: MISC_FEATURE
<222> LOCATION: (106)..(116)
<223> OTHER INFORMATION: CDR3

<400> SEQUENCE: 32

Met Ala Trp Ile Pro Leu Phe Leu Gly Val Leu Val Tyr Cys Thr Gly
1               5                   10                  15

Ser Val Ala Ser Ser Gly Leu Thr Gln Pro His Ser Val Ser Val Ser
            20                  25                  30

Pro Gly Gln Thr Ala Asn Ile Thr Cys Ser Arg Asp Lys Leu Gly His
        35                  40                  45

Lys Phe Ala Ser Trp Tyr Gln Gln Lys Pro Gly Gln Ser Pro Ala Leu
    50                  55                  60

Leu Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Asn Thr
            100                 105                 110

Thr Ala Val Phe Gly Gly Gly Thr Lys Leu Thr Val Leu Ser Gln Pro
        115                 120                 125

Lys Ala Ala Pro Ser Val Thr Leu Phe Pro Pro Ser
    130                 135                 140

<210> SEQ ID NO 33
<211> LENGTH: 20
<212> TYPE: PRT
<213> ORGANISM: Homo sapiens
<220> FEATURE:
<221> NAME/KEY: MISC_FEATURE
<223> OTHER INFORMATION: KRIX-1 heavy chain CDR1

<400> SEQUENCE: 33

Gly Tyr Asn Phe Thr Gly Tyr Ser Ala Ser Gly His Ile Phe Thr Ala
1               5                   10                  15

Tyr Ser Val His
            20

<210> SEQ ID NO 34
<211> LENGTH: 17
<212> TYPE: PRT
<213> ORGANISM: Homo sapiens
<220> FEATURE:
<221> NAME/KEY: MISC_FEATURE
<223> OTHER INFORMATION: KRIX-1 heavy chain CDR2

<400> SEQUENCE: 34

Arg Ile Asn Pro Asn Ser Gly Ala Thr Asp Tyr Ala His Lys Phe Gln
1               5                   10                  15

```
Gly

<210> SEQ ID NO 35
<211> LENGTH: 18
<212> TYPE: PRT
<213> ORGANISM: Homo sapiens
<220> FEATURE:
<221> NAME/KEY: MISC_FEATURE
<223> OTHER INFORMATION: KRIX-1 heavy chain CDR3

<400> SEQUENCE: 35

Ala Asp Asn Tyr Phe Asp Ile Val Thr Gly Tyr Thr Ser His Tyr Phe
1               5                   10                  15

Asp Tyr

<210> SEQ ID NO 36
<211> LENGTH: 12
<212> TYPE: PRT
<213> ORGANISM: Homo sapiens
<220> FEATURE:
<221> NAME/KEY: MISC_FEATURE
<223> OTHER INFORMATION: KRIX-1 light chain CDR1

<400> SEQUENCE: 36

Arg Ala Ser Gln Ser Val Ala Ser Ala Tyr Leu Ala
1               5                   10

<210> SEQ ID NO 37
<211> LENGTH: 7
<212> TYPE: PRT
<213> ORGANISM: Homo sapiens
<220> FEATURE:
<221> NAME/KEY: MISC_FEATURE
<223> OTHER INFORMATION: KRIX-1 light chain CDR2

<400> SEQUENCE: 37

Gly Ala Ser Ser Arg Ala Thr
1               5

<210> SEQ ID NO 38
<211> LENGTH: 10
<212> TYPE: PRT
<213> ORGANISM: Homo sapiens
<220> FEATURE:
<221> NAME/KEY: MISC_FEATURE
<223> OTHER INFORMATION: KRIX-1 light chain CDR3

<400> SEQUENCE: 38

Gln Gln Tyr Gly Thr Ser Ala Leu Leu Thr
1               5                   10
```

ANTIBODIES WHICH BIND AND INHIBIT BLOOD FACTOR VIII

The present application is a continuation of U.S. application Ser. No. 10/566,851 (allowed), which was filed Feb. 1, 2006 now U.S. Pat. No. 7,785,594 (published as US 2006-0292149 A1 on Dec. 28, 2006), which is a 371 U.S. national phase of International Application No. PCT/BE04/00118, filed Aug. 16, 2004, and which claims benefit of GB 0319118.6, filed Aug. 14, 2003 and GB 0319345.5, filed Aug. 18, 2003, the entire contents of each of which is hereby incorporated by reference in this application.

FIELD OF THE INVENTION

The present invention relates to the modification of inhibitory antibodies in order to achieve a variable maximal inhibitory activity and its application in the development of antithrombotic agents as well as to pharmaceutical compositions and mixtures including such antibodies.

BACKGROUND OF THE INVENTION

The formation of blood clots does not only limit bleeding in case of injury (haemostasis) but can occlude important arteries or veins, leading to serious organ damage and death. Thrombosis is thus blood clot formation at the wrong time and place.

Upon damage of a vessel, the coagulation (clotting) system is immediately initiated producing thrombin and blood platelets adhering to matrix proteins, which in turn leads to the aggregation of additional platelets into a growing platelet plug in concert with the conversion of fibrinogen in the blood to the insoluble fibrin.

At each step of the coagulation cycle, a clotting factor zymogen undergoes limited proteolysis and itself becomes an active protease. This clotting-factor enzyme activates the next clotting factor zymogen until thrombin is formed which connects fibrinogen to the insoluble fibrin clot. The blood clotting factors include factor I (fibrinogen), factor II (prothrombin), tissue factor (formerly known as factor III), factor IV ($Ca^{2+}$), factor V (labile factors), factor VII (proconvertin), factor VIII (antihemophilic globulin, or 11AHG11), factor IX (Christmas factor), factor X (Stuart factor), factor XI (plasma thromboplastin antecedent, or "PTA"), factor XII (Hageman factor), factor XIII (fibrin stabilizing factor), and factors HMWK (high-molecular weight kininogen, or Fitzgerald factor), PREK (prekallikrein, or Fletcher factor), Ka (kallikrein), and PL (phospholipid).

Fibrinogen is a substrate for the enzyme thrombin (factor IIa), a protease that is formed during the coagulation process by the activation of a circulating zymogen, prothrombin (factor II). Prothrombin is converted to the active enzyme thrombin by activated factor X in the presence of activated factor V, Ca 2+ and phospholipid. Two separate pathways, called the "intrinsic" and "extrinsic" systems, lead to the formation of activated factor X. In the intrinsic system, all the protein factors necessary for coagulation are present in the circulating blood. In the extrinsic system, tissue factor, which is not present in the circulating blood, is expressed on damaged endothelium, by activated monocytes, by cells in the arteriosclerotic plaque or by cells outside the vessel wall. Tissue factor then acts as the receptor and essential cofactor for the binding of factor VII, resulting in a bimolecular enzyme (tissue factorVIIa) to initiate the extrinsic pathway of coagulation. This mechanism also activates the intrinsic pathway of coagulation.

As a summary, the coagulation system involves a cascade of complex and regulated biochemical reactions between circulating blood proteins (coagulation factors), blood cells (in particular platelets) and elements of an injured vessel wall. Venous thromboembolic disease (deep vein thrombosis, pulmonary embolism, atrial fibrillation) remains a major health issue, with an incidence of 1 to 3 per 1000 individuals per year and a high early mortality rate (Nordstrom et al. (1992) *J Intern Med.* 232, 155-160; Rosendaal (1997) *Thromb Haemost* 78, 1-6).

Current anticoagulant therapies primarily consist of heparin (or low molecular weight heparins) and vitamin K antagonists, which are both unsatisfactory and inconvenient. All treatments carry a significant risk of bleeding (Res. Comm. British Thoracic Soc. (1992) *Lancet.* 340(8824):873-6), which limits both the dose and duration of treatment and may require regular monitoring (Hylek & Singer (1994) *Ann Intern Med.* 120, 897-902; Cannegieter et al. (1995) *N Engl J Med.* 333, 11-17). New drugs are currently being developed, but none appears to match optimal criteria of efficacy, safety and convenience.

Antibodies directed to coagulation factors were recently developed as anticoagulant agents. Antibodies directed against Factor IX, Factor IXa, Factor X, Factor Xa, Factor XI, factor XIa, Factor VIII, Factor VIIIa, Factor V, Factor Va, Factor VII, Factor VIIa, thrombin, the Von Willebrand Factor, Tissue Factor and other elements of the coagulation cycle have already been described.

WO 97/26010 discloses antibodies inhibiting coagulation in what is described as "a self-limited manner". These antibodies are characterized by the fact that high concentrations of such antibodies prolong coagulation tests such as the APTT only in a limited manner and will not render blood unclottable in contrast to high doses of anticoagulant agents such as heparin. However, a limited increase in APTT does not exclude the risk of bleeding. It has not been shown that these antibodies having a so-called "self-limiting neutralizing activity" can avoid completely neutralizing their target coagulation factor, thereby exposing the patient to high bleeding risks. Indeed, in patients with complete deficiency of coagulation factors such as FVIII or FIX, APTT is also prolonged in only a finite manner. The blood of such patients is also not uncoagulable in contrast to blood treated with high doses heparin. However, such patients with severe FVIII or FIX deficiency suffer from dramatic hemorrhagic diseases called hemophilia A or B. As antibodies inhibiting coagulation factors in a "self-limited manner" have biological activities mimicking the blood defect in these patients, they may expose the patients to high bleeding risks.

WO 01/04269 discloses a human monoclonal antibody, Krix-1, which only partially inhibits FVIII activity whatever the (molar) excess of antibody over FVIII. This limited inactivation of FVIII was called a "plateau effect". By comparison with antibodies having "self-limiting neutralizing activity", antibodies such as Krix-1 have the advantage that they cannot completely inactivate the target coagulation factor. WO 01/04269 A1 discloses that despite this limited FVIII inactivation, Krix-1 was efficient in preventing thrombosis in a hamster model of venous thrombosis. This antibody was also effective in a mouse model of vena cava thrombosis (Singh et al. (2002) *Blood* 99, 3235-3240.). Krix-1 inhibits about 90% FVIII activity (range 85-95%) in normal human plasma.

Factor FVIII therefore appears as a potential target for anticoagulant drugs. However, it is likely that the bleeding tendency associated to the use of anti-FVIII antibodies will be related to the degree of inhibition of the target coagulation factor. It is therefore important to establish methods to generate antibody preparations with an optimal ratio between efficacy (antithrombotic action) and safety (low bleeding tendency).

So far, all of the anticoagulant agents tested in clinical studies are associated with an important risk of bleeding. Besides, LMWH requires frequent subcutaneous administrations and coumarin derivatives require regular monitoring.

Safer and more efficient methods for the prevention and treatment of venous thromboembolic diseases are therefore desirable. Ideal anticoagulant agents should not carry a risk of bleeding complications or of overdosing. They should not require regular monitoring, be easy to administer and well-tolerated. Finally, an antidote should be available.

As a summary, there is still a stringent need for good anti-coagulant therapies with better safety/efficacy ratios.

SUMMARY OF THE INVENTION

The present invention relates to a method for modifying the inhibitory activity of an antibody, preferably without significantly affecting the affinity. The invention further relates to antibodies or fragments thereof obtained by such a method and their use in developing antibody mixtures with a variable maximal inhibitory activity of their protein target. More in particular, this invention relates to human monoclonal antibodies or fragments thereof modified in different ways affecting the size of the antibody and not the affinity thereof so to partially inhibit in a variable maximal manner a coagulation factor. These may be used as antithrombotic agents. The present invention also relates to using such antibodies and fragments of such antibodies in a pharmaceutical preparation.

Thus, the present invention relates to a method for obtaining a library of at least two inhibitory antibodies against factor VIII with variable maximal inhibitory activity and with substantially the same affinity. The method comprises modifying the size of an inhibitory antibody against FVIII or fragment thereof either by modifying the glycosylation in the variable region of said inhibitory antibody or by reducing the antibodies to an antigen-binding fragment, after which modifications the antibodies or fragments are selected for which affinity to FVIII is not substantially affected.

According to a first embodiment of the present invention, a method is provided for modifying the inhibitory activity of an inhibitory antibody or a fragment thereof by modification of the glycosylation, e.g. in a variable region of the antibody. The affinity of said antibodies for their target protein may only be affected in a limited way. Particularly, according to one aspect of the present invention the dissociation constant of the modified antibody or fragment thereof is modified by a factor less than 3, preferably less than 2, most preferably less than 1.5. The present invention demonstrates that antibodies or fragments thereof can be developed with a modified inhibitory capacity, but a similar affinity, by modification of the glycosylation in a variable region of the antibody. More particularly, the present invention relates to a method for decreasing the inhibitory activity of an inhibitory antibody or a fragment thereof by deglycosylation. These antibodies are of use in situations where a variable or sub-maximal inhibition of a target protein is required, as in the field of coagulation. According to a second aspect of the invention, the production of antibody fragments is used to obtain further modulations of inhibitory activity, which fragments can themselves be modified by deglycosylation. In such a way a series of different antibodies with a varying maximal inhibitory activity is obtained.

The current limitation of human monoclonal antibodies to FVIII or fragments thereof is that there is no method allowing the production of antibodies with any given "plateau inhibition", which would allow the selection of the antibodies or fragments with an optimal ratio between safety and efficacy to treat or prevent thrombosis.

A further aspect of the present invention relates to a method of obtaining antibodies or fragments thereof with variable maximal inhibitory activity but similar affinity by modifying the glycosylation, more specifically in the variable region. In one embodiment the affinity of an antibody or fragment with modified glycosylation is less than 1 nM. Without being limited by theory, it is believed that this method is particularly suited for those antibodies where the epitope of the target protein corresponding to antigen-binding site is in the vicinity but does not correspond exactly to the active or interactive site of said protein. The modification of glycosylation is optionally obtained by exposing the native antibodies or fragments thereof to carbohydrate cleaving or transforming enzymes. Alternatively, the antibodies with modified glycosylation are obtained by producing the antibodies in cell lines with suitable glycosylation enzymes or by modifying the cell culture conditions to modify the activity of the glycosylation enzymes of the cell line producing the antibodies. In another embodiment of the present invention, the antibodies with modified glycosylation are obtained by genetically modifying the antibody in order to remove or introduce glycosylation sites, for example by site-directed mutagenesis. In a further embodiment, of the present invention the antibodies with modified glycosylation are obtained by chemical synthesis. Fragments can be obtained from complete antibodies or produced directly by recombinant or chemical synthesis by methods described in the art. Antibodies or fragments with a modified inhibitory capacity (and preferably a substantially unaffected affinity), are optionally identified by measuring the inhibitory capacity (and the affinity) of a native antibody, modifying the glycosylation of the antibody and again measuring the inhibitory capacity (and the affinity) of the modified antibody. Thus, according to a particular embodiment, the present invention relates to a method for producing an FVIII inhibitory antibody or fragment thereof said antibody or fragment inhibiting FVIII between 20 and 85% at saturating concentrations comprising the steps of:

providing an intact FVIII inhibitory antibody or fragment thereof and, modifying the glycosylation of said antibody or antibody fragment at the posttranslational level or modifying the glycosylation of said antibody or antibody fragment by altering essential amino acids in the glycosylation consensus sequence of the variable region of said antibody.

According to a further aspect of the present invention, the method of the invention is applied in the development of antibodies directed against a protein which is involved in a complex, i.e. a protein which for its biological function, requires interaction with other proteins. According to a specific embodiment, the method of the invention is used to modify the inhibitory activity of antibodies or fragments thereof directed against an element of the haemostasis system or to polypeptides or other molecules which bind to an element of the haemostasis system, yet more in particular to factors of the coagulation cascade, in order to obtain antibodies with variable inhibitory effect on blood coagulation. Thus, a method is presented which is of particular use in modifying the inhibitory effect of inhibitory antibodies directed against Factor V, Factor VII, Factor VIII (FVIII), Factor IX, Factor X, Factor XI, thrombin, the von Willebrand Factor or other elements of the coagulation cascade, so as to obtain antibodies variable maximal anti-coagulant activity.

In a more particular embodiment, the modification of glycosylation is applied to an antibody against FVIII or a fragment thereof, more specifically the monoclonal Krix-1 antibody or a fragment thereof. The method of the invention is used to obtain modified Krix-1 antibodies or fragments thereof demonstrating variable maximal inhibition of FVIII. More particularly, a method is described to obtain modified Krix-1 antibodies with an inhibitory capacity between 20% and 90%, more in particular between 20% and 80%, yet more in particular between 20% and 70% and still more in particular between 20% and 60%.

The present invention further relates to inhibitory antibodies or fragments thereof obtained by the method of the invention, with modified glycosylation and a modified inhibitory activity, characterised in that the affinity of said antibodies or fragments thereof for their target protein is substantially unaffected. The invention also relates to fragments, derivatives and proteins being similar to said antibodies. The antibodies of the present invention include fragments thereof such as, but not limited to, Fab fragments, F(ab')2 fragments and scFvs. In a more particular embodiment of the invention, antibodies and antibody fragments demonstrating variable maximal inhibition of FVIII are disclosed.

The present invention discloses antibodies or fragments thereof inhibiting FVIII activity by about 85, 50, 40, 30 and 20% More particularly the invention relates to an anticoagulation factor monoclonal antibody inhibiting less than 65% of FVIII activity and preventing thrombosis in mammal models of thrombosis.

The present invention further relates to monoclonal antibodies or fragments thereof modified as compared Krix-1 in that an altered glycosylation has resulted in a different maximal inhibition of FVIII activity. More particularly the invention relates to modified Krix-1 antibody or a fragment thereof which is an anti-coagulation factor monoclonal antibody inhibiting less than 65% of FVIII activity and preventing thrombosis in mammal models of thrombosis.

The present invention further relates to inhibitory or anti-coagulant antibodies and fragments thereof directed against FVIII derived from a cell line called Krix-1, with a modified inhibitory activity but retaining similar affinity for FVIII as Krix-1. In a more particular embodiment said antibody is derived from Krix-1 or a fragment thereof or a recombinant produced analogue of such a modified antibody, more in particular the variable regions of said antibody have an amino acid similarity of at least 80%, preferably at least 90% or more with the Krix-1 antibody or a fragment thereof. Such antibodies include antibodies or fragments thereof comprising an immunoglobulin heavy chain variable region comprising a sequence having at least 80%, preferably at elast 90%, more preferably at least 95%, most preferably at least 98% sequence homology with SEQ ID NO:2, wherein Asn at position 47 has been modified to Glutamine, Aspartic acid, or Glutamic acid or wherein Thr at position 49 has been modified to Alanine.

Such antibodies include antibodies obtained by chain shuffling whereby the antigen binding site of the antibody has the epitope specificity of the modified Krix-1, e.g. has the epitope specificity of KRIX-1Q or KRIX-1A. Such antibodies further include fragments of the modified Krix-1 or fragments of Krix-1 modified according to the present invention, provided they have anti-coagulant activity. Thus, the invention also relates to a chimeric antibody comprising a heavy and a light chain, wherein a variable region of said antibody is modified to introduce or remove N-glycosylation site, said antibody characterized by inhibiting the function of a coagulation factor in a limited manner, whereby thrombosis is inhibited and partial inhibition of coagulation is achieved.

In a particular embodiment of the present invention, said antibody is the recombinant antibody of Krix-1 or a fragment thereof, produced in any suitable host cell, e.g. in CHO cells. In a yet more particular embodiment, said antibody is a mutant of Krix-1 with modified N-glysosylation in the variable region, more particularly with a mutated glycosylation site at positions Asn47 to Thr49, more in particular with Asn47 changed to Gln47 (KRIX-1Q), Glu47 (KRIX-1E) or Asp47 (KRIX-1D) and/or Thr49 to Ala49 (KRIX-1A).

Moreover, the invention relates to the cell lines producing the antibodies according to the present invention, more particularly the cell lines producing antibodies with altered post-translational modifications, more particularly with the characteristics of Krix-1, KRIX-1Q or KRIX-1A.

According to another aspect of the invention, two or more antibodies or antibody fragments with different maximal inhibitory activity of a ligand can be combined resulting in a mixture with an intermediate inhibitory activity. A particular embodiment of the invention is a mixture of two or more inhibitory antibodies against FVIII or fragments thereof, which ensures a given maximal inhibition of FVIII whatever the excess of the mixture of antibodies over FVIII. Using combinations of different inhibitory antibodies and/or fragments thereof in specific ratios, mixtures with specific inhibitory activity of FVIII can be obtained. Thus, the present invention relates to a combination of two or more antibodies or antibody fragments with different maximal inhibitory activities. According to a specific embodiment the native antibody is combined with one or more antibodies or fragments thereof having a lower inhibitory activity. According to a further embodiment the native antibody is combined with an antibody or antibody fragment having a modified glycosylation with respect to the native antibody. Such combinations or mixtures are of interest for further adjustment of the inhibitory activity of the antibody, e.g. in the development of patient-specific pharmaceuticals as described herein.

The invention further relates to the use of the antibodies and antibody fragments of the present invention for the controlled inhibition of biological processes, more particularly in therapeutic applications. The invention further relates to the use of a combination of antibodies or fragments thereof with different maximal inhibitory activity of FVIII as therapeutic composition. A particular embodiment of the invention relates to the use of mixtures of one or more of the antibodies or fragments of the present invention having modified glycosylation with the corresponding unmodified antibodies or fragments for the controlled inhibition of their common ligand. Thus another aspect of the invention is a pharmaceutical composition comprising one or more antibodies or fragments thereof, more particularly one or more antibodies or fragments thereof having modified glycosylation and a pharmaceutically acceptable carrier.

More particularly, the usefulness of antibodies with modified inhibitory activity is demonstrated in the field of coagulation disorders. The antibodies and fragments thereof according to the invention are of use for the controlled inhibition of coagulation. Thus the invention relates to the use of antibodies or fragments thereof with modified inhibitory activity of coagulation factors in the manufacture of a medicament useful for the treatment of subjects suffering from a coagulation disorder, more in particular from a venous thromboembolic disease. The present invention furthermore relates to a method of treatment of coagulation disorders by using said antibodies or fragments. A particular object of the present invention is to provide an effective anti-thrombotic therapy with reduced risk of bleeding in animals, particularly in humans. This is achieved with the use of the antibodies or fragments of the present invention with modified maximal inhibitory activity of coagulation factors and mixtures thereof, more particularly with the use of inhibitory antibodies or fragments directed against FVIII with modified maximal inhibitory activity.

Accordingly, one aspect of the present invention is a method of treatment comprising administering an effective dose of one or more therapeutic monoclonal antibody(ies) or fragment(s) thereof which has been modified in such a way as to modify or introduce a glycosylation site in the antibody in order to modify the inhibitory effect of the said antibody on the activity and/or the interaction(s) of the ligand recognized by the said antibody(ies) with other proteins or reagents interacting with the said ligand.

Particularly, according to the present invention, a method is provided for inhibiting thrombosis comprising administering an effective dose of one or more monoclonal antibody or fragment(s) thereof which inhibit(s) a factor involved in coagulation. In a particular embodiment of the invention the antibody or at least one of the antibodies is modified in such a way as to modify or introduce a glycosylation site in the antibody in order to modify the inhibitory effect of the said antibody on the interaction(s) of the ligand recognized by the said antibody with other proteins or reagents interacting with the said ligand. A specific embodiment of the present invention is a method for adjusting antithrombotic treatment to the clinical situation of the patient based on varying the maximal inhibitory activity of anti-coagulating antibodies or fragments thereof. Thus, the present invention relates to the formulation of a medicament for the treatment or prevention of thrombosis, taking into account the clinical situation of the patient, which comprises the selection of one or more antibodies in order to obtain maximal inhibitory activity, suitable for said treatment.

Accordingly, one aspect of the present invention is pharmaceutical formulation for inhibiting thrombosis, which can be adjusted based on the clinical needs of the patient, comprising an effective dose of an anticoagulant monoclonal antibody or a mixture thereof derived from Krix-1 in which the glycosylation in the variable region has been modified, optionally in a mixture with unmodified Krix-1.

Alternatively, such pharmaceutical composition is a mixture of two compounds being selected from the group consisting of native Krix-1, a fragment of native Krix-1, Krix-1 with modified glycosylation in the variable region and a fragment of Krix-1 with a modified glycosylation in the variable region.

More particularly the pharmaceutical compound comprises one or more monoclonal antibodies which have been modified in the glycosylation in the region Asn47-Thr49. Optionally this modification is a mutation, more in particular with Asn47 changed in Gln47 (KRIX-1Q), Glu47 (KRIX-1E) or Asp47 (KRIX-1D) and/or Thr49 in Ala49 (KRIX-1A). Alternatively, this modification is obtained by contacting the native Krix-1 antibody or fragments thereof with conditions which ensure modification of the glycosylation at Asn47-49 (such as increased levels of deglycosylation enzymes or increased levels of enzymes involved in glycosylation, different cell lines for expressing antibodies or media formulation used for the cultivation of the cell lines).

Accordingly, one aspect of the present invention is a library comprising at least two anticoagulant antibodies with variable maximal inhibitory capacity of FVIII but with similar affinity for FVIII. According to a particular embodiment said library comprises antibodies derived from Krix-1 by modulation of the glycosylation of the variable region of Krix-1. The invention further relates to a method for manufacturing a medicament for the controlled treatment or inhibition of coagulation in the treatment of thrombosis, comprising selecting one or more of said anticoagulant monoclonal antibody(ies) derived from Krix-1 from the library of the invention. Particularly, the library comprises antibodies derived from Krix-1 by deglycosylation of the glycosylation site located at Asn47-Thr49.

Yet another aspect of the invention relates to a method for the identification of an antibody which competes with an inhibitory FVIII antibody comprising the steps of contacting FVIII or a fragment of FVIII comprising the C1 domain with a first inhibitory antibody and a candidate inhibitory antibody, and assaying the capacity of said candidate antibody to compete with the binding of the FVIII inhibitory antibody said FVIII or fragment of FVIII. In a particular embodiment of the invention the known inhibitory FVIII antibody used for the identification of novel, competing antibodies is Krix-1. According to a particular embodiment of the invention the antibodies obtained in such a way are further screened for their FVIII inhibitory activity. The present invention thus also relates to (purified) antibodies obtained from this method which can be used in mixtures together with Krix-1 or modifications thereof according to the present invention and in the generation of pharmaceutical compositions.

In the description and examples, reference is made to the following sequences:

SEQ ID NO: 1: nucleotide sequence encoding the Krix-1 heavy chain variable region
SEQ ID NO: 2: amino acid sequence comprising the Krix-1 heavy chain CDR regions
SEQ ID NO: 3: nucleotide sequence encoding the Krix-1 light chain variable region
SEQ ID NO: 4: amino acid sequence comprising the Krix-1 light chain CDR regions
SEQ ID NO: 5: recombinant Krix-1 forward primer heavy chain
SEQ ID NO: 6: recombinant Krix-1 reverse primer heavy chain
SEQ ID NO: 7: recombinant Krix-1 forward primer light chain
SEQ ID NO: 8: recombinant Krix-1 reverse primer light chain
SEQ ID NO: 9: Krix-1Q forward primer
SEQ ID NO: 10: Krix-1Q reverse primer
SEQ ID NO: 11: Krix-1A forward primer
SEQ ID NO: 12: Krix-1A reverse primer
SEQ ID NO: 13: Krix-1E forward primer
SEQ ID NO: 14: Krix-1E reverse primer
SEQ ID NO: 15: Krix-1D forward primer
SEQ ID NO: 16: Krix-1D reverse primer
SEQ ID NO:17: scFv-KRIX-1VL forward primer
SEQ ID NO:18: scFv-KRIX-1VL reverse primer
SEQ ID NO:19: scFv-KRIX-1VH forward primer
SEQ ID NO:20: scFv-KRIX-1VH reverse primer
SEQ ID NO:21: scFv-KRIX-1VLVH with His(6)tag forward primer
SEQ ID NO:22: scFv-KRIX-1VLVH with His(6)tag reverse primer
SEQ ID NO:23: scFv-Asn47Gln KRIX-1VLVH(His) forward primer
SEQ ID NO:24: scFv-Asn47Gln KRIX-1VLVH(His) reverse primer
SEQ ID NO:25: nucleotide sequence comprising the scFv-Asn47Gln KRIX-1VLVH(His)
SEQ ID NO:26: Amino acid sequence comprising the scFv-Asn47Gln KRIX-1VLVH(His)

SEQ ID NO:27: CHO-scFvKRIX-1VLVHQ(His) forward primer
SEQ ID NO:28: CHO-scFvKRIX-1VLVHQ(His) reverse primer
SEQ ID NO:29: nucleotide sequence encoding RHD5 VH region
SEQ ID NO:30: Amino acid sequence comprising the RHD5 VH region
SEQ ID NO:31: nucleotide sequence encoding RHD5 VL region
SEQ ID NO:32: Amino acid sequence comprising the RHD5 VL region

DEFINITIONS

The term "Antibody" ("Ab") as used herein refers to a monoclonal or polyclonal antibody molecule. "Fragments" of an antibody include molecules comprising: either both heavy and light chains, (such as Fab, F(ab)$_2$, F(ab')$_2$ or ScFV) or single heavy or light chains (e.g. light chain dimers), optionally including their constant region (or parts thereof), or optionally minor modifications (such as allotypic variants) of that constant region, parts, thereof, in particular the specificity-determining parts thereof, i.e. the variable regions of the antibodies, subparts thereof, in particular the hypervariable parts thereof, such as peptides made up of stretches of amino acids comprising at least one CDR, optionally with adjacent framework sequences, e.g. of up to about 10 amino acid sequences at one or both CDR.

Optionally, according to the present invention, antibodies are IgG antibodies, particularly IgG1. F(ab')2 refers the antibody fragment obtainable after pepsin cleavage and is built up of both light chains and parts of the heavy chains disulfide linked via the hinge region. The Fab fragment is obtainable from the intact antibody or from the F(ab')2 by papain digestion of the hinge region and contains a one light chain and one part of the heavy chain. Fragments of antibodies can also be obtained by synthesis or by recombinant methods described in the art. Fragments such as scFv fragments can be obtained by PCR amplification of the relevant parts of the antibody nucleotide sequence and cloning these in an expression vector together with appropriate additional sequences such as a linker sequence in the case of an scFv fragment.

The term "native antibody" as used herein refers to a glycosylated inhibitory antibody. The glycosylation of the 'native antibody' is the glycosylation as observed under standard culturing of a lymphoblastoid cell line producing said antibody, i.e. unmodified by the addition of enzymes or by mutations. Preferably, such a native antibody is a wild-type antibody, but it is envisaged that it can be an antibody which has been modified at a site different from the glycosyation consensus sequence. Additionally, an F(ab) fragment or other fragment of an antibody can be a "native" antibody fragment in the context of this definition as it contains the glycosylation pattern as present on the intact antibody. In the context of the present invention, when reference is made to the glycosylation of an antibody derived from Krix-1 compared to the native Krix-1 antibody, a comparison to the antibody as obtained from the Krix-1 cell line (deposited under the terms of the Budapest Treaty with the Belgian Coordinated Collections of Micro-organisms under accession number LMBP 5089CB on Jul. 1, 1999), under standard cultivation conditions is intended.

The term "derivative" as used herein refers to an antibody or fragment thereof which has been altered chemically or genetically in a way which does not affect its length or glycosylation in the variable region.

A "modified antibody" or "modified antibody fragment" as used herein refers to an antibody, which in comparison to the wild-type antibody, is different with respect to its size, more particularly, which is different either with respect to its glycosylation. but with a similar affinity to its ligand as the wild-type antibody. According to a further embodiment of the invention the inhibitory activity of the antibody is modified by reducing the size of the antibody without modifying the affinity, e.g. by producing fragments (e.g. Fab fragments and recombinantly expressed fragments such as ScFV fragments).

An antibody having both heavy and light chains linked by disulfide bridges (i.e. having a size identical to the wild-type antibody) is referred to as an "intact" antibody (regardless of its glycosylation status).

It is understood that the concept of the present invention can be applied to both intact antibodies and antibody fragments, i.e. a fragment of an antibody (obtainable by different methods as described herein) can be modified to further affect its inhibitory activity, either by a further fragmentation or by deglycosylation.

The term "antibody (or antibody fragment) with modified glycosylation" as used herein refers to antibodies or fragments thereof which have been engineered or produced in a way that their glycosylation differs from that of the native antibody, meaning that certain extra carbohydrates are present or certain carbohydrates are missing relative to the native antibody or a combination thereof at different positions. In the context of the present invention the modifications in the glycosylation of the antibodies occur in the variable region (i.e. VH and/or VL) of the antibodies.

An "inhibitory antibody" or an "antibody with inhibitory activity" as used herein refers to an antibody which inhibits the activity of its target protein at least partially. According to a particular embodiment of the present invention, the inhibitory antibodies inhibit the interaction of their target protein with another protein. A specific embodiment of an inhibitory antibody is an anti-Factor VIII antibody, more particularly an antibody inhibiting the binding of FVIII to other factors such as vWF and/or phospholipids. Preferably, the antibodies are directed against the C1 domain of FVIII. Inhibitory antibodies can be alloantibodies against exogenous FVIII. Inhibitory antibodies can be of human or animal origin. In the context of antibodies inhibiting the activity of factors of the coagulation cascade, also referred to as anti-coagulant antibodies herein, the maximal inhibitory of the antibody may be critical, complete inhibition of coagulation may cause side-effects such as uncontrolled bleeding.

A variable maximal inhibitory activity as used herein relates to a maximal inhibitory activity, as defined for an antibody or a mixture of antibodies according to the present invention, which can be modified. For instance, according to the present invention the maximal inhibitory activity of an antibody against FVIII is decreased, by modification of the glycosylation, more particularly by deglycosylation of the variable region. Thus, antibodies with variable maximal inhibitory activity are obtained. It is understood that in the context of the present invention for an antibody to be considered as inhibitory, its inhibitory effect should be at least 1%.

Alternatively, according to another embodiment of the present invention the maximal inhibitory activity of an antibody against FVIII is enhanced by modification of the glycosylation, more particularly by hyperglycosylation of the variable region using different cell lines or cell cultivation condition or expressing cells in cell types which have transgenic glycosylation enzymes. Such antibodies should have inhibitory effects of at most 97%, or at most 98% or at most 99%.

'Complementarity determining regions (CDR)' in the present invention refers to the hypervariable amino acid sequences within antibody variable regions which interact with the epitope on the antigen. In one embodiment of the present invention the CDR regions are the CDR1, CDR2 and CDR3 regions of the variable light (VL) and heavy (VH) chains respectively (L1, L2, L3 and H1, H2, H3 respectively) of antibodies directed against an element of the coagulation cycle.

"Humanized antibody" as used herein, refers to non-human antibody molecules in which amino acids have been replaced in the non-antigen binding regions in order to more closely resemble a human antibody.

A "Reshaped human antibody" or a "Human hybrid antibody" as used herein, refers to a human antibody in which amino acids in the antigen binding regions have been replaced with sequences in accordance with the present invention, e. g. CDR's, or other parts of variable regions which have been derived from the repertoire of human antibodies.

Sequence comparisons. Comparisons of protein or nucleotide sequences are designated in terms of sequence identity or sequence similarity. Where in accordance with the present invention comparisons are made between amino acid sequences of two VH regions or of two VL regions, or comparisons are made between two nucleotide sequences encoding CDRs, or sequences comprising CDRs, the level of sequence identity or similarity between two sequences may include having at least 80%, preferably at least 80% more preferably at least 90%, even more preferably at least 95% and most preferably at least 99% sequence identity or similarity between two sequences.

Nucleotide or amino acid sequences which are "identical" means that when two sequences are aligned, the percent sequence identity, i.e. the number of positions with identical nucleotides or amino acids divided by the number of nucleotides or amino acids in the shorter of the sequences, is higher than 80%, preferably at least 90%, even more preferably at least 95%, most preferably at least 99%, more specifically is 100%. The alignment of two nucleotide sequences is performed by the algorithm as described by Wilbur and Lipmann (1983) *Proc. Natl. Acad. Sci. U.S.A.* 80:726, using a window size of 20 nucleotides, a word length of 4 nucleotides, and a gap penalty of 4.

Two amino acids are considered as "similar" if they belong to one of the following groups GASTCP; VILM; YWF; DEAN; KHR. Thus, sequences which are similar means that when the two protein sequences are aligned the number of positions with identical or similar nucleotides or amino acids divided by the number of nucleotides or amino acids in the shorter of the sequences, is higher than 80%, preferably at least 90%, even more preferably at least 95% and most preferably at least 99%, more specifically is 100%.

The term "modified" denotes any protein (or polypeptide) molecule in which a single or a number of amino-acids have been either substituted by any other amino-acid residue or deleted. Such amino-acid substitution or deletion can be located anywhere in the protein molecule. It also denotes protein molecules in which amino-acid residues have been substituted and/or deleted at more than a single location. In the latter case, any combination of substitution and deletion can be considered. It also refers to polymorphisms (i.e. the regular and simultaneous occurrence in a single interbreeding population of two or more alleles of a gene, where the frequency of the rarer alleles is greater, typically greater than 1%, than can be explained by recurrent mutation alone).

The term "modifying the glycosylation of an antibody at the posttranslational level" refers to modifications such as changing culture conditions of antibody expressing cells, changing the cell type for expressing antibodies and the use of deglycosylating and/or glycosylation enzymes, either intracellularly in the cell expressing an antibody or part of an antibody or by treating an intact antibody or part thereof with these enzymes.

The term "Carbohydrate cleaving or transforming enzymes" as used herein relates to enzymes that are able to cleave carbohydrates, parts of a carbohydrate structure and/or different molecules coupled thereto (like N-acetyl) from a protein, a peptide or a certain amino acid therein or that are able to covalently bind carbohydrates to amino acids or to other carbohydrates on a protein or peptide. Examples of such cleaving enzymes are the peptide N-4(N-acetyl-beta-glucosaminyl)asparagine amidase F (PNGase F), also called N-glycosidase F, beta-galactosidase, sialidase, α- and β-mannosidase, α-fucosidase, β-N-acetylhexosaminidase, and hyaluronidase. Glycosylating enzymes include sialyltransferases and other glycosyltransferases.

"Antigen binding region" as used herein refers to the region of an antibody involved in the binding of the antigen. More in particular, the antigen binding region can be determined as the amino acids and their substituents which contact through non-covalent bonding amino acids or molecules of the target protein.

Nomenclature: the monoclonal antibody KRIX-1 produced in a lymphoblastoid cell line (LCL) is called Krix-1

The monoclonal antibody KRIX-1 produced in CHO cells line is called CHO-recKrix-1.

A monoclonal antibody KRIX-1 antibody with a substitution of Asn47 into Gln is called Asn47Gln Krix-1 or Krix-1Q.

The monoclonal antibody KRIX-1 antibody with a substitution of Asn47 into Asp and produced in CHO cells is called Asn47Asp Krix-1 or Krix-1D.

The monoclonal antibody KRIX-1 antibody with a substitution of Asn47 into Glu and produced in CHO cells is called Asn47Glu Krix-1 or Krix-1E.

The monoclonal antibody KRIX-1 antibody with a substitution of Thr49 into Ala and produced in CHO cells is called Asn47Gln Krix-1 or Krix-1A.

DETAILED DESCRIPTION OF THE INVENTION

The present invention will be described with reference to certain embodiments and to certain figures but the present invention is not limited thereto but only by the claims.

It was recently observed that a recombinant antibody produced in CHO cells inhibited FVIII significantly differently from the antibody produced in a human lymphoblastoid cells. This unexpected observation indicated that posttranslational modification could modulate the inhibitory activity of antibodies directed against FVIII, more particularly of Krix-1. The identification of a glycosylation site in the variable region of Krix-1 further showed that glycosylation of the variable region could modulate the activity of Krix-1.

The activity of Krix-1 treated with enzyme removing carbohydrate structures was therefore investigated. Deglycosylation of Krix-1 dramatically modified its inhibitory activity (down to about 60%). However, the affinity of Krix-1 for FVIII was not changed significantly. These observations were unexpected, because it has never been reported before that glycosylation can modulate the function of an antibody otherwise than by altering the affinity or specificity. Moreover, the glycans which act as ligands for receptors bind in a structure-specific manner, resulting in an on/off signal, not amenable to modulation. The ability to modify the activity of an antibody without significantly modifying its specificity or affinity makes it possible to adjust the inhibitory activity, e.g. limit the inhibitory activity to suppress possible side-effects, such as in the case of anti-coagulant antibodies. Moreover, the possibility to obtain a selection of antibodies with the same affinity to the antigen but different inhibitory activity, allows the mixing different "glycan-modified" antibodies to generate an antibody preparation with different (and very specific) maximal inhibitory activity ("plateau"). Moreover, the limitation of the modification of glycosylation to the variable region ensures that other characteristics of the antibody known to be influenced by glycosylation of the constant region (e.g. half-life) are not affected.

The fact that glycosylation of the antigen binding site of antibodies could alter their inhibitory capacity without significantly modifying their affinity was confirmed by the observation that recombinant antibodies carrying a point mutation in the glycosylation site inhibited only 40% FVIII activity. More interestingly, mixing the different modified forms of recombinant mAb-Krix-1 made it possible to obtain combinations with varying plateaus of FVIII inhibition, e.g. when administered in excess. Accordingly, this strategy allows the production of an anticoagulant FVIII preparation inhibiting FVIII in a very large therapeutic range, allowing to select the best ratio between anticoagulant action and bleeding risks. The long half-life of the antibodies allows to obtain these target inhibition for prolonged period of time.

Without being limited to theory, the present invention shows that the glycosylation of KRIX-1 does not significantly change the affinity for the target coagulation factor and thereby does not change the binding to the target coagulation factor demonstrates that the mechanism by which the glycosylation of KRIX-1 affects the inhibitory activity of KRIX-1 is by altering the interaction of the target coagulation factor with other proteins of the coagulation cascade at a site in the variable region. The present invention includes a method based on modification of the glycosylation site of the variable region of an antibody resulting in a modification of the inhibitory effect of the said antibody on the interaction(s) of the ligand(s) recognized by an antibody with other proteins or reagents interacting with the said ligand. According to a further embodiment of the invention the inhibitory effect of the antibody on the ligand is modified by changing the size of the antibody without altering its affinity for the ligand. This can be achieved by producing fragments of the inhibitory antibody.

The present invention thus provides a variety of antibodies and fragments thereof, which are characterized by modifications of the glycosylation of the antigen binding site of native antibodies resulting in a modification of the maximal inhibitory activity exerted by the antibodies optionally without significantly altering their affinity or specificity for their target protein. In a certain embodiment of the present invention, the antibodies are directed against an element of the coagulation system, more in particular against Factor VIII. Additionally, an optionally in combination therewith further variations of inhibitory activity can be obtained by modifying the size of the antibodies, i.e. by providing antibody fragments.

According to one aspect of the present invention, modification of the does not necessarily significantly affect its affinity for the antigen. More particularly, according to the first aspect of the present invention, the affinity of the antibody is changed due to modifications in glycosylation in such a way that the dissociation konstant (Kd) of the antibody is modified by a factor less than 3, which is considered as a substantially unaffected affinity of the antibody for the antigen; preferably the $K_D$ of the antibody is modified by a factor less than 2.5, more preferably less than 2, especially preferably less than 1.5. Thus antibodies having substantially the same affinity for an antigen are antibodies for which the $K_D$ of the antibody differ by a factor of less than 2.5, more preferably less than 2, especially preferably less than 1. Affinity of an antibody for its antigen can be measured in different ways known to the person skilled in the art. According to a particular embodiment of the present invention affinity of the antibody for the antigen is measured by surface plasmon resonance analysis, as described herein. According to a particular embodiment of the present invention the $K_D$ of the modified antibodies to the antigen is less than $1 \times 10^{-9}$M, preferably less than $0.5 \times 10^{-9}$M.

The present invention thus relates to antibodies with modified glycosylation, a modified inhibitory activity and a substantially unaffected affinity for their target protein. The present invention further relates to the use of said antibodies as a medicine. The present invention also relates to methods of preparing such antibodies, a method of selecting such antibodies and pharmaceutical compositions comprising them. The present invention also relates to said antibodies in mixtures with other antibodies, such as with their native antibody.

In a particular embodiment of the present invention, the antibodies are directed against a "protein which is involved in a complex". Proteins involved in a complex can be defined as proteins which interact with one other element next to their target during the performance of their specific activity. Such other elements can be proteins, peptides, phospholipids, salts, lipids, nucleic acids, organic molecules, et. An example of a protein involved in a complex is Factor VIII which interacts with phospholipids and/or the Von Willebrand Factor upon performing its activity (FVIIIa).

In a more particular embodiment of the present invention, the antibodies are directed against an element of the haemostasis system. Elements of the haemostasis system include the factors of the coagulation cascade and include factors such as Factor V, Factor VII, Factor VIII, Factor X, Factor XI, thrombin, the Von Willebrand Factor and other elements of the coagulation cycle and their active derivatives. In a more particular embodiment of the invention, the antibodies are directed against Factor VIII, more particularly against the C1 or C2 domain of factor VIII, although it is not limited thereto.

The invention further relates to the use of said antibodies and fragments in the manufacture of a medicament useful for the treatment of subjects suffering from a certain disorder wherein a protein (such as Factor VII) involved in a complex is involved. Such diseases can be selected from cardiovascular diseases, cancer, autoimmune diseases or immunology related disorders, inflammatory, metabolic, haematological or respiratory diseases. The invention further relates more in particular to the treatment of subjects suffering from a coagulation disorder, more in particular from a venous thromboembolic disease with said antibodies. Venous thromboembolic disease includes deep disorders such as vein thrombosis, pulmonary embolism and atrial fibrillation. The present invention furthermore relates to a method of treatment of coagulation disorders by using said antibodies. According to a specific embodiment of the present invention, the antibodies and fragments of the present invention are of use in the manufacture of a medicament for the treatment of sepsis or SIRS.

The present invention therefore relates to antibodies or fragments thereof with a modified glycosylation and a modified maximal inhibition, but a substantially unaffected affinity for its target protein. The antibodies can be completely deglycosylated or partially. The antibodies can be modified to bear different carbohydrates at different sites or can have an increased glycosylation. In a particular embodiment of the present invention, the maximal inhibitory capacity of the antibodies can be decreased or increased. Alternatively the maximal inhibitory activity is reduced by reducing the size of the antibody or fragment, provided that the affinity is substantially unaffected. In a particular embodiment of the invention, the inhibitory capacity of the antibodies of the invention are sub-maximal ($\leqq 99\%$) and can range between 20% or 99%. More in particular, the inhibitory activity of said antibodies can be 90%, 80%, 70%, 60%, 50%, 40%, 30% or 20%. The inhibitory activity of said antibodies can be measured by any known method in the art. For the field of coagulation, the inhibitory activity of for example antibodies against FVIII can be determined by using the Bethesda assay.

The present invention also relates to a method for preparing, from a (native) inhibitory antibody, a modified antibody with a modified glycosylation, a modified inhibitory capacity and a substantially similar affinity, characterised in that the method comprises the steps of measuring the inhibitory capacity and the affinity of the native antibody, modifying the glycosylation of the antibody and again measuring the inhibitory capacity and the affinity of modified antibody.

The present invention further relates to a method of developing at least two inhibitory antibodies with a different glycosylation, a different inhibitory capacity and a substantially similar affinity. The method of developing the antibodies of the present invention starts with the preparation and development of an inhibitory (native) antibody against a certain target protein. According to a particular embodiment of the invention, the native antibody is directed to or effectively 'binds' an antigen near to the active site of the target protein or to sites of the protein important for the activity of the target protein. More particularly, the antibodies can be directed against an epitope located at a certain distance from a physiologically functional site of the target protein (e.g. the binding of the target protein to another protein of a complex). This can be achieved by immunization with this epitope. Selection of the antibody is based on its inhibitory activity. The next step is to modify the glycosylation of the variable region of the native antibody by different methods (enzymatic cleavage, enzymatic adding of carbohydrates, mutations, etc.). Optionally this is performed taking into account accessibility of the glycosylation site and interaction with the antigen. Alternatively, selection is based on unaffected affinity and modified inhibitory activity compared to the native antibody (or to compared to each other).

In a particular embodiment of the present invention, a library of at least two antibodies directed against FVIII is provided with a different glycosylation in the variable region, a different inhibitory capacity and substantially similar affinity. Thus, the invention relates to the production of a modified antibody of an inhibitory native antibody with a modified inhibitory capacity and an affinity, which is substantially unaffected as compared to the native antibody, but with a modified inhibitory capacity. In a particular embodiment of the invention, said modified antibody (for use in said library) is obtained by producing the native antibody as a recombinant antibody in suitable host cells, such as CHO cells. Alternatively, said antibody or antibody fragment is prepared by site-directed mutagenesis, more in particular said antibody has no N-glycosylation site in the variable region. In another alternative, said antibody or antibody fragment is prepared by exposing antibodies to carbohydrate cleaving enzymes. In yet another embodiment said antibody or antibody fragment is produced by chemical synthesis. According to a particular embodiment, said antibody or antibody fragment has a factor VIII inhibitory capacity between 20% and 90%, more in particular between 30% and 80%, yet more in particular between 40% and 70% and still more in particular between 50% and 60% or any combination thereof.

In another embodiment of the present invention, the modified antibody directed against Factor VIII is produced by a cell line called Krix-I or by a cell line producing antibodies with the same characteristics. In a more particular embodiment said antibody is derived from a native antibody which is Krix-1 or a fragment thereof or a recombinant produced analogue of a modified Krix-1, more in particular said antibody has an amino acid similarity of at least 80%, preferably at least 90% with Krix-1 or a fragment thereof. In a yet more particular embodiment of the present invention, said antibody is the recombinant antibody Krix-1 or a fragment thereof, produced in CHO cells and with an inhibitory activity of around 84%. Removal of the glycosylation of Krix-1 at Asn47 in the consensus glycosylation sequence Asn47-X-Thr49-Y can be achieved in several ways. Mutation of Asn47 to any amino acid or mutation of Thr49 to any amino acid different from Serine, will result in the absence of glycosylation. The mutation Thr49Ser might have no effect on the glycosylation but could also result in a modified glycosylation pattern or the even the absence of glycosylation, as not every potential consensus glycosylation site, occurring in a protein seqeunce is also effectively glycosylated in the expressed protein. Alternatively, mutation of the amino acid at position 48 or 50 into Proline will prevent glycosylation but in addition can cause local distortion of the tertiary structure of the antibody. In a yet more particular embodiment, said antibody is a mutant of Krix-1 with mutated positions Asn47 to Thr49, more in particular with Asn47 changed in Gln47 (KRIX-1Q), Glu47 (KRIX-1E) or Asp47 (KRIX-1D) and/or Thr49 in Ala49 (KRIX-1A). The present invention also relates to antibodies derived from Krix-1 by incubating the native antibody with carbohydrate cleaving enzymes such as N-glucosidase-F, more particularly to antibodies obtained in this way and with an inhibitory activity of around 50%. The antibodies derived from Krix-1 can have an inhibitory activity of at least 20%, more particularly at least 40%, 50% or 80%.

When fragments are used which are expressed by recombinant technology (e.g. scFv fragments) deglycosylated forms can be obtained by expression of a protein comprising the glycosylation consensus sequence in a glycosylation deficient yeast strain or by expression in bacteria which perform no glycosylation at all.

These antibodies and fragments thereof carrying modified glycosylation in the variable region, optionally in or in the proximity of a CDR have the advantageous properties that they exhibit therapeutically useful maximal inhibitory activity different from the native antibody, while inactivating the target protein only partially even when the antibody is in a molar excess, like the native antibody. These glycan-modified antibodies and fragments thereof are therefore useful as agents for obtaining only a partial inhibition a target protein, more in particular as anticoagulant agents allowing to achieve desirable partial inhibition of a coagulation factor out of reach of the native antibody in the case of an antibody directed against an element in the coagulation system. Similarly, unmodified fragments, having the same affinity as the intact antibody, but a lower inhibitory activity can be used in combination with the optionally modified intact antibodies to obtain a mixture ensuring a particular inhibition. Thus the present invention allows, by selection or development of an antibody with a particular inhibitory capacity, the formulation of a medicament for controlling coagulation is a well-defined manner.

The fact that the affinity of the modified antibodies of the invention is not significantly changed is furthermore of critical value for their use in mixtures and means that the modified antibodies will, similarly to the native antibody displace the natural ligand. This allows the formulation of mixtures of antibodies in order to obtain a well-defined inhibitory activity. More particularly, this is of interest in the field of anticoagulant antibodies, where the maximal inhibitory activity may be critical. For instance, in some clinical settings, anti-FVIII antibodies with different inhibitory activities could be required. For example, short term prophylaxis of thrombosis following surgical intervention may be optimally treated with drugs with a potency different from those required for the treatment of a chronic condition such as atrial fibrillation.

Thus, according to a particular embodiment of the present invention, the modified antibody or antibody fragment is used in a mixture with other antibodies directed against the same target protein, yet more in particular directed against the same antigen or derived from the same cell line. This mixture can comprise the native antibodies together with modified antibodies directed against the same target protein or the mixture can contain two antibodies modified in a different way in their glycosylation pattern. The different parts of the mixture can be mixed in such quantities so that any wanted inhibitory activity can be obtained.

The present invention relates to a method for preparing antibodies with a modified glycosylation and modified maximal inhibition, but without an altered affinity or specificity for their target protein. Therefore, the present invention relates to a method of producing said antibodies comprising the step of exposing antibodies to carbohydrate cleaving or transforming enzymes. Alternatively, the method of preparation of the present invention comprises the step of producing the antibodies in cell lines with suitable glycosylation enzymes or by modifying the cell culture conditions to modify the activity of the glycosylation enzymes of the cell line producing the antibodies. In another embodiment of the present invention, the method of preparing said antibodies comprises the step of genetically modifying the antigen binding site of the antibody in order to remove or introduce glycosylation sites, for example by site-directed mutagenesis.

In a particular embodiment of the invention, the glycosylation of the antibody is modified in its variable region or in the amino acids in the proximity of the antigen binding region.

The present invention thus relates to antibodies which have a modified glycosylation pattern relative to the native antibody.

The native antibody can be prepared according to known methods in the art.

The initial data on intact antibodies being expressed in different cell lines, on intact antibodies being treated with deglycosilating enzymes, and on site directed mutagenesis of the glycosylation consensus size show that the inhibitory effect of such antibody is correlated with the size of the glycosylation. The present invention presents the concept that for inhibitory antibodies such as Krix-1, the inhibitory effect of the antibody decreases with the three-dimensional size. This concept is confirmed by the used of Fab fragments and scFv fragments of Krix-1 which have lower inhibitory levels that intact antibody.

The present invention further shows that mixtures of inhibitory antibodies, being derived from the same native intact antibody, with different individual inhibitory activity, result in a mixture wherein an intermediate inhibitory activity is obtained. This equally is applicable for mixtures of different native and intact antibodies which are competitive for each other such as a mixture of the monoclonal Krix-1 antibody (first antibody) and a second monoclonal antibody obtained from the RHD5 cell line.

Yet another aspect of the invention provides methods to isolate further inhibitory antibodies which can be used according to the present invention, based on their ability tocompete with a known inhibitory antibody, such as Krix-1. The present invention thus provides methods and tools to identify, starting from Krix-1, additional antibodies which compete with Krix-1 binding. Such an antibody is which is optionally is inhibitory, and which further optionally has a plateau effect. The experimental setup of such a method is described in example 13.

Monoclonal antibodies against a certain target protein can be produced by any technique which provides the production of antibody molecules by continuous cell lines in cultures such as the hybridoma technique originally developed by Kohler and Milstein (Kohler and Milstein (1975) *Nature* 256, 495-497), as well as the trioma technique, the human B-cell hybridoma technique (Kozbor et al. (1983) *Immunol. Today* 4, 72), the EBV-hybridoma technique to produce human monoclonal antibodies (Cole et al. (1985) in "Monoclonal Antibodies and Cancer Therapy," Alan R. Liss, Inc. p. 77-96) and the like, all are within the scope of the present invention.

The monoclonal antibodies may be human monoclonal antibodies or chimeric human-mouse (or other species) monoclonal antibodies or even from any other kind known in the art, such as coming from camels or lamas. Human monoclonal antibodies may be made of any numerous techniques known in the art (e.g. Teng et al. (1983) *Proc. Natl. Acad. Sci. U.S.A.* 80, 7308-7312; Kozbor et al. (1983), *Immunol. Today* 4, 72-79, Olsson et al. (1982) *Methods. Enzymol.* 92, 3-16). Chimeric antibody molecules may be prepared containing a mouse antigen-binding domain with human constant regions (Morrison et al. (1984) *Proc. Natl. Acad. Sci. USA.* 81, 6851; Takeda et al. (1985) *Nature* 314, 452).

Various procedures known in the art may be used for the production of polyclonal antibodies to epitopes of the target proteins. For the production of antibody, various host animals can be immunized by injection with a specific protein, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyosl, polyanions, peptides, oil emulsions, keyhole limpet hemocyanisn, dinitrophenols, and potentially useful human adjuvants such as BCG (Bacille Calmette-Guerin) and *Corynebacterium parvum.*

A molecular clone of an antibody to a selected protein epitope can be prepared by known techniques. Recombinant DNA methodology (see e.g. Maniatis et al. (1982), Molecular Cloning, A Laboratory Manual, Cold Spring Harbor Laboratory, New York) may be used to construct nucleic acid sequences which encode a monoclonal antibody molecule, or antigen binding region thereof.

The present invention provides for antibody molecules as well as fragments of such antibody molecules. A particular aspect of the invention provides antibody fragments with the same affinity as the intact antibody but Antibody fragments, which contain the idiotype of the molecule, can be generated by known techniques. For example, such fragments include but are not limited to the F(ab')2 fragment which can be produced by pepsin digestion of the antibody molecule, the Fab' fragments which can be generated by reducing the disulfide bridges of the F(ab')2 fragment and the Fab fragments which can be generated by treating the antibody molecule with papain and a reducing agent. Antibody molecules can be purified by known techniques, e.g. immunoabsorption or immunoaffinity chromatography, chromatographic methods such as HPLC (high performance liquid chromatography), or a combination thereof.

The antibodies of the present invention can be prepared by conventional hybridoma techniques, phage display, combinatorial libraries, immunoglobulin chain shuffling, site directed mutagenesis and humanization techniques to generate novel antibodies with limited maximal inhibitory activity.

The present invention further provides modified antibodies derived from native monoclonal antibodies being produced by on purpose immunization in animals, preferably in mouse, for instance by injecting human Factor VIII in mice and then fusing the spleen lymphocytes with a mouse myeloma cell line, followed by identifying and cloning the cell cultures producing anti-factor VIII antibodies as further as described in WO97/26010 and/or WO 01/04269. More particularly, in the context of the present invention, epitopes of the antigen flanking the 'active' or 'interactive' (e.g. binding with other factors of a complex) site of said antigen can be used for immunization, in order to promote the development of antibodies in which the inhibitory effect of the antibody is not linked directly to the binding of the antigen through the CDR.

One aspect of the present invention provides for antibodies which are modified in their glycosylation pattern. The modification of the glycosylation of native antibodies can be obtained through different methods known in the art. Modification of the glycosylation pattern in the antigen binding site of the antibodies of the present invention can be achieved by enzymatic treatment of purified antibodies. Alternatively, modification of the glycans of the antibodies of the present invention can be achieved by producing the antibodies in cell lines with suitable glycosylation enzymes or by modifying the cell culture conditions to modify the activity of the glycosylation enzymes of the cell line producing the antibodies. Alternatively, the antibodies of the present invention can also be produced by genetically modifying the antigen binding site of the antibody in order to remove or to introduce glycosylation sites.

Many carbohydrate cleaving or transferring enzymes can be applied in order to modify the glycosylation pattern of a native antibody. The glycosylation can be increased or decreased completely or partially. In a particular embodiment, the modification is obtained in the antigen binding region of the antibody. Enzymes can be applied on a native antibody in a different order and under variable circumstances (concentrations, time, temperature, buffer, etc.) in order to obtain antibodies with different glycosylation patterns.

Enzymes such as peptide N-4(N-acetyl-beta-glucosaminyl)asparagine amidase F (PNGase F), also called N-glycosidase F can be used. This enzyme has a broad specificity, and it releases nearly all known N-linked oligosaccharide chain from proteins (Plummer T H Jr et al. (1984) *J Biol Chem.* 259, 10700-10704). This enzyme releases tetra- and penta-antennary chains. It is noteworthy that the activity of the enzyme can only be predicted when the glycoprotein is fully denatured. Accordingly, the activity of the enzyme on an intact antibody must be controlled in each case. Methods to control the deglycosylation of the antibody are described in Current Protocols in Protein Science, Ed. G. Taylor, Unit 12.4; John Wiley & Sons, Inc.

In particular, the glycosylated and deglycosylated antibodies are compared by isoelectrofocusing.

Truncated glycoforms of IgG can be generated by sequential enzymatic treatment as described in Mimura et al. (2001) *J Biol Chem.* 276, 45539-45547, and summarized in FIGS. 1 and 2.

Sialic acids are the terminal sugars on many N- and O-linked oligosaccharides. To remove sialic acid, the native IgG in acetate buffer, pH 5.0, are exposed to sialidase (such as the sialidase from *Arthrobacter ureafaciens*, Roche Molecular Diagnostics, East Sussex, UK) at 37° C. for 24 h. Removal of sialic acids results in an increase in the isoelectric point of the protein. IEF can therefore be used to control removal of sialic acids.

Upon removal of sialic acids, galactose can be removed by treatement with beta-galactosidase (*Diplococcus pneumoniae*, Roche Molecular Biologicals) in acetate buffer, at 37° C. for 24 h. Following removal of sialic acid and galactose, N-acelylglucosamine can be cleaved by treatment with N-acetyl-beta-D-glucosaminidase (*D. pneumoniae*, Roche, Molecular Biochemicals) in 37° C. for 24 h. Mannose residues can then be removed by treatment with α-mannosidase (jack bean, Glyko, Oxfordshire, UK) at 37° C. for 48 h (Mimura Y. et al. cited supra).

Different types of sialidase have also been described. The sialidase (neuraminidase) from *Arthrobacter ureafaciens* releases both alpha 2,3- and alpha 2,6-linked sialic acids, whereas the sialidase from the Newcastle disease virus releases only alpha 2,3 linked sialic acids (Jassal et al. (2001) *Biochem Biophys Res Comm.* 286: 243-249). The endoglycosidase F2 cleaves the bound between the two GlcNAc residues in the core region, leaving one GlcNAc still bound to the protein. Endoglycosidase F2 preferentially releases biantennary complex-type oligosaccharides chains from glycoproteins but does not cleave tri- or tetraantennary chains Endoglycosidase F3 is another endoglycosidase with a narrow substrate range: it cleaves triantennary chains. A core fucosylated biantennary chain is the only other demonstrated substrate. It does not cleave high-mannose hybrid, nonfucosylated biantennary or tetraantennary chains. All linkages which can be cleaved by endoglycosydase F2 and F3 are not exposed in a mature antibody. Methods suitable to determine whether an antibody can be usefully modified by these endoglycosidase include SDS-PAGE, lectin binding methods using *Ricinus communis* agglutinin-1 and IEF as described above.

Conversely, glycan residues can be enzymatically added to carbohydrate expressed in the variable part of the antibody. For example, treatment with sialidase as described above can be followed by treatment with galactosyl-transferase and UDP-Gal in a suitable buffer (Krapp et al. (2003) *J Mol Biol.* 325, 979-989). The modified antibodies are then homogenous for galactosylation of the carbohydrate chain (biantennary digalactosylated glycoform).

The purification of antibodies carrying different oligosaccharides is also known to persons skilled in the art. The antibodies carrying different oligosaccharides can be purified by lectin affinity chromatography, such as Concanavalin A (binding to a bisecting GlcNAc). Aleuria aurantia differentiates on the basis of core fucosylation. *Ricinus communis* agglutinin 1 fractionates according to the number of galactose residues because this lectin exhibits specific affinity to oligosaccharides ending with galactose (Youings et al. (1996) *Biochem J.* 314, 621).

All carbohydrate residues are not exposed in a mature antibody. Methods suitable to determine whether an antibody can be usefully positively or negatively purified using the above lectin are well known by those skilled in the art. Unbound antibody can be tested to determine their inhibitory activity on FVIII using the Bethesda method (Kasper et al. (1975) *Thromb Diath Haemorrh* 34, 612). Similarly, the activity of the antibody captured on the column and eluted using a suitable buffer, can be tested using the Bethesda method (cited supra).

An alternative method for modifying the glycosylation of an antibody is to generate recombinant antibodies with modified glycosylation pattern by producing recombinant antibodies in cell lines selected as a function of their repertoire of glycosylation enzymes. Chinese Hamster Ovary cells (CHO) are well known example of such a cell line.

Although CHO cells have most of the human repertoire of glycosylation enzymes, they are deficient in particular glycosyltransferases. In particular, the alpha 2,6-sialyl-transferase gene (1,2) is not expressed endogenously in CHO cells. This enzyme adds terminal galactose sugars with sialic acid in the alpha 2,6 position on the Gal beta 1, 4GlcNAc-R sequence. However, CHO cells express a functional alpha 2,3-sialyl-transferase so that the terminal sialic acids are in alpha 2,3 linkage to galactose. Alpha-3/4 fucosyltransferase is also not synthesized by these cells (Grabenhorst et al. (1999) *Glycoconj. J.* 16, 81).

Another method to produce recombinant antibody with modified glycosylation pattern is to use a cell line genetically modified to express glycosylation enzyme from other strains. In particular, a CHO-K1 cell line transfected with an alpha 2,6-sialyltransferase gene cloned from another strain can be used (cited supra).

Any expression system is potentially suitable for the generation of recombinant antibody with modified glycosylation pattern such as yeast (for example *Saccharomyces, Pichia, Hansenula*), insect cells (baculovirus expression), plant cells or plants, or mammalian cells. For the expression of fragments of an antibody yeast expression provide an alternative for insect or mammalian cell expression. If no glycosylation at all is needed, the expression in bacteria is considered.

With respect to yeasts, the methylotrophic yeast *Pichia pastoris* was reported to attach an average of 8 to 14 mannose units, i.e. Man(8-14)GlcNAc(2) per glycosylation site (Tschopp in EP0256421) and approximately 85% of the N-linked oligosaccharides are in the size range Man(8-14) GlcNAc(2) (Grinna and Tschopp (1989) *Yeast* 5, 107-115.). *Aspergillus niger* is adding Man(5-10)GlcNAc(2) to N-glycosylation sites (Panchal and Wodzinski (1998) *Prep Biochem Biotechnol.* 28, 201-217). The *Saccharomyces cerevisiae* glycosylation deficient mutant mnn9 differs from wild-type *S. cerevisiae* in that mnn9 cells produce glycosylated proteins with a modified oligosaccharide consisting of Man (9-13)GlcNAc(2) instead of hyperglycosylated proteins (Mackay et al. in U.S. Pat. No. 5,135,854), However, characteristic for *S. cerevisiae* (wild-type and mnn9 mutant) core oligosaccharides is the presence of terminal alpha1,3-linked mannose residues (Montesino et al. (1998) *Protein Expr Purif.* 14, 197-207.). Oligosaccharides attached to N-glycosylation sites of proteins expressed in *P. pastoris* or *S. cerevisiae* och1mnn1 are devoid of such terminal alpha1,3-linked mannoses (Gellissen et al. (2000) *Appl Microbiol Biotechnol.* 54, 741-750). Terminal alpha1,3-linked mannoses are considered to be allergenic (Jenkins et al. (1996) Nat. Biotechnol. 14, 975-981). Therefor, proteins carrying on their oligosaccharides terminal alpha1,3-linked mannose residues are likely not suitable for diagnostic or therapeutic purposes.

The repertoire of glycosylating enzymes differs from cell type to cell type. In order to obtain a desired glycosylation pattern one or more glycosylating enzymes can be (over) expressed by transient or stable transfection. Equally one or more glycosylating enzymes can be temporarily (for example by antisense or siRNA technology) or permanently inhibited (gene inactivation). In certain embodiment yeast cells are used which have a limited repertoire of enzymes involved in glycosylation. Herein one or more human genes involved in glycosylation can be introduced to obtain a desired glycosylation pattern.

Generally glycosylation often improves the solubility of a protein. In certain embodiments, it is advantageous to express a recombinant protein with an extensive glycosylation (and good solubility) and to treat the recombinant protein afterwards with deglycosylating enzymes.

In certain embodiments it is advantageous to express to recombinant proteins with a (cleavable) secretion signal which direct the protein into the growth medium. This is for example the case for yeast cells which are difficult to lyse. In addition the recombinant protein can have a tag (e.g. His-tag) or additional domain in order to facilitate purification. Said tag or domain can also be cleavable (e.g. by Thrombin or factor X).

In a particular embodiment of the invention, the Factor VIII inhibitory activity of the recombinant antibody produced in any of these expression systems can then be evaluated in the Bethesda assay using the modification of the Nijmegen method as described above.

Furthermore, also culture conditions can be exploited to modify the glycosylation of the recombinant antibody. The concentration of dissolved oxygen at steady state in serum free culture has an effect on glycosylation of antibody. The extent of galactosylation is reduced with reduced dissolved oxygen concentrations (Kunkel et al. (1998). *J Biotechnol.* 62, 55-71). Supplementing the medium with more than 20 mM N-acetylglycosamine can also induce new antibody glycoforms (Tachibana et al. (1992). *Biochem Biophys Res Commun.* 189, 625-32; Tachibana et al. (1996) *In Vitro Cell Dev Biol Anim.* 32, 178-183). Glucocorticoid hormones and interleukin 6 are involved in the modulation of protein glycosylation (Canella and Margni (2002) *Hybrid Hybridomics* 21, 203). Other factors which influence glycosylation are changes in the pH of culture medium and the availability of precursors and nutrients.

Therefore, selection of the cell line and cell culture conditions can have a big influence on the glycosylation pattern.

Another alternative to the enzymatical modifications and the recombinant production of the antibodies is to use (site-directed) mutagenesis. New glycosylation sites can be introduced or existing glycosylation sites can be removed with this technique. N-glycosylation sites can be introduced by site directed mutagenesis in the variable region of the antibody. Preferably, the mutations are introduced as single amino acid changes, to minimize the effect of the amino acid substitution on the affinity of the antibody for the antigen. Addition of and N-glycosylation site is performed by creation of an Asn-X-Ser/Thr sequence, most commonly by mutating a codon to encode Asn. Moreover, it is preferable that the sites for additional glycosylation are selected at positions predicted to be accessible to glycosyltransferases. Alternatively, amino-acid stretches containing N-glycosylation sites can be selected in the published sequences of antibodies glycosylated in the variable region. The selection of antibodies inhibiting FVIII activity in a desirable manner can be made using the Bethesda assay (Kasper et al. (1975) cited supra). The protein structure can also be modified to indirectly modify glycosylation (Lund et al. (1996) *J Immunol.* 157, 4963, Lund et al. (2000), *Eur J Biochem.* 267, 7246). Site-directed mutagenesis is a method well-known to the person skilled in the art, and include the Zoller and Smith method (Zoller and Smith (1987) *Methods Enzymol.* 154:329-50).

The present invention also provides fragments of any of the above mentioned monoclonal antibodies such as Fab, Fab', F(ab')2, scFv, CDR's, single variable domains as well as derivatives, homologs and combination of these.

In a particular embodiment of the present invention, the antibodies are directed against elements of the coagulation system, more in particular against Factor VIII.

The present invention therefore relates to antibodies derived from Krix-I, more in particular to antibodies modified in their glycosylation pattern derived from Krix-I and with a modified factor VIII inhibitory activity. Particularly, the glycan-modified antibodies are derived from the human monoclonal antibody Krix-1, fragments thereof or contains one or several complementary determining region thereof. Exemplary antibodies with modified glycosylation site are antibodies produced by treatment of Krix-1 with N-glycosidase F. Particularly are genetically modified antibodies containing the mutations Asn47Glu (Krix-1E) and Thr49Ala (Krix-1A) in the CDR1 of the heavy chain of Krix-1.

Modification of the glycosylation modifies the Factor VIII inhibitory activity of mAb-Krix-1. A particular method to evaluate the inhibitory activity of an antibody with modified glycosylation pattern is the Bethesda assay (Kasper et al. (1975), cited supra) using the modification of the Nijmegen method (Verbruggen et al. (1995) *Thromb Haemost.* 73, 247-251). In this assay, normal pooled plasma, used as a FVIII source, is mixed with an equal volume of antibody. After an incubation of 2 h with antibody, the residual FVIII activity was measured by a Factor chromogenic or clotting assay.

The cell line named Krix-1 was disclosed in WO 01/04269 and was deposited with the BCCM/LMBP (Belgian Co-ordinated Collections of Microorganisms/Plasmid Collection Laboratorium voor Moleculaire Biologie, University of Gent K.L. Ledeganckstraat 35, B-9000 Gent, BE under accession number LMBP 5089CB on Jul. 1, 1999, by Dr. Marc Jacquemin, Center for Molecular and Vascular Biology, Onderwijs & Navorsing, Herestraat 49, 3000 Leuven, Belgium.

By partial inhibition of FVIII activity, we mean that the maximal inhibition of Factor VIII activity by a certain antibody is lower or equal to 99%, as determined using a suitable test method, such as the Bethesda assay. The residual Factor VIII activity is then measured using a coagulation or a Chromogenic Factor VIII assay. A suitable chromogenic assay is for example the Coatest$^R$ (Chromogenix-Instrumentation Laboratory SpA, Milano, Italy).

The antibodies described in this invention can be useful in the therapy or prevention of different diseases. In the case of antibodies directed against elements of the coagulation system, the antibodies are useful in therapeutic and pharmaceutical compositions for thrombotic disorders associated with myocardial infaction, unstable angina, atrial fibrillation, stroke, renal damage, pulmonary embolism, deep vein thrombosis, percutaneous translumenal coronary angioplasty, disseminated intravascular coagulation, sepsis, transplants, shunts.

The present invention allows the generation of pharmaceutical compositions for the treatment and prevention of disorders or syndromes wherein at the one hand partial inhibition of Factor VIII is desired but where on the other hand a certain level of remaining Factor VIII activity is beneficial in the treatment or prevention of said disorders or syndromes. An example hereof is systemic inflammation which is the possible endpoint of a number of clinical conditions including pancreatitis, ischemia, multiple trauma and tissue injury, haemorrhagic shock, immune-mediated organ injury and infection. Since quite comparable pathological changes are observed in systemic inflammation independently of the initial cause, the term "systemic inflammatory response syndrome" (hereinafter referred as SIRS) has been commonly quoted to account for such changes and is therefore used in the present application in accordance with the recommendations of the American College of Chest Physicians as formulated by R. C. Bone et al. in *Chest* (1992) 101, 1644-1655. The definition and aetiology of SIRS is also described in Nyström (1998) *J. Antimicrob. Chemother.* 41 Suppl A, 1-7. Sepsis represents a SIRS associated to infection. Shock, whether of septic origin or not, is characterized namely by (a) hypotension persisting despite adequate fluid resuscitation and (b) abnormalities related to hypoperfusion or organ dysfunction.

According to Bone et al. in *Chest* (1997) 112, 235-43, the early systemic inflammation, which is an integral part of SIRS, is normally compensated by a later anti-inflammatory response. An equilibrium between pro-inflammatory and anti-inflammatory events leads to a favorable clinical outcome. However, the balance between these two antagonistic events is fragile and easily disrupted, since many interacting mediators are involved. In recent years much knowledge has accumulated about the patho-physiology of SIRS and the development of related septic shock, the paradigm of which is due to infection with gram (−) microorganisms. Thus endotoxins liberated by such microorganisms activate a number of host cells and in particular monocytes and macrophages. This results in the production of pro-inflammatory cytokines including tumor necrosis factor (hereinafter referred as TNF), interleukins 1, 6 and 8 (hereinafter referred IL-1, IL-6 and IL-8). Enzymes produced by the same cells lead to activation of the coagulation, complement and bradykinin systems. Superoxide radicals and metabolites of arachidonic acid, including platelet activating factor (hereinafter referred as PAF) are produced according to Parillo et al. in *Ann. Intern. Med.* (1990) 113, 227-242.

Activation of the coagulation system together with adhesion of polymorphonuclear cells and platelets to the vascular endothelium is essential in the pathogenesis of SIRS since it results in the formation of thrombus in the microvasculature. Thrombi impair organ perfusion, which ends up with organ dysfunction or failure. At the intestinal level, this produces an increased absorption of endotoxins from the bacterial flora, which further boosts the release of pro-inflammatory cytokines and organ dysfunction. The disseminated intravascular coagulation (hereinafter referred as DIC) is therefore an essential component of the pathophysiology of sepsis and septic shock.

A compensatory anti-inflammatory response emerges later, from which the clinical outcome of sepsis will depend. Too weak or too strong responses can aggravate the clinical situation by failure to control DIC or by leading to uncontrolled bleeding and immune suppression with increased susceptibility to further infection. The individual factors intervening in this anti-inflammatory phase are not all identified with certainty but a number of molecules have been clearly implicated. Thus the levels of anti-thrombin (hereinafter referred as AT, a plasma serine protease inhibitor with a normal plasma concentration of 3 μmol/L), activated protein C (APC) and tissue factor pathway inhibitor (hereinafter referred as TFPI, another endothelial-bound protein), three potent inhibitors acting at various steps in the coagulation cascade, are severely reduced during sepsis and their plasma concentrations are inversely correlated with bad clinical prognosis according to E. F. Mammen in *Intensive Care Med.*

(1998) 24, 649-50. Such reduced levels are due both to increased consumption and reduced synthesis, namely by the liver.

The coagulation system is currently divided in an initiation phase, an amplification phase and an effective phase. Initiation occurs by activation of factor VII on tissue factor (TF) or by the contact factor XII. This results in the generation of small amounts of thrombin, which activates an amplification loop leading to more thrombin formation. Two co-factors in this amplification loop, factor V and factor VIII, are activated, their function being to increase by several logs of magnitude the cleavage of prothrombin and factor X respectively. The effective phase of the coagulation cascade eventually leads to the formation of fibrin and clot retraction. Thrombin therefore occupies a central role in the development of DIC associated with sepsis or SIRS of other origin. This discovery has led to therapeutic attempts to reduce thrombin formation. In humans, studies comparing antithrombin with a synthetic protease inhibitor (Maki et al. in *Gynecol. Obstet. Invest.* (1987) 23:230-240) or heparin (Blauhut et al. in *Thromb. Res.* (1985) 39:81-89) documented a significant attenuation of disseminated intravascular coagulation after antithrombin treatment, but neither included a placebo control group. According to Fourrier et al. in DIC, Excerpta Medica, Amsterdam (1993) 221-226, a placebo-controlled, double blind trial in patients with septic shock and DIC treatment with a plasma concentrate of antithrombin achieved significantly earlier correction of DIC but failed to decrease mortality in a significant manner. More recently, plasma-derived or recombinant AT have been tested in the control of sepsis, namely according to Eisele et al. in *Intensive Care Med.* (1998) 24:663-72. However all these embodiments encountered serious problems. Natural plasma antithrombin is a relatively poor inhibitor of thrombin (it achieves full inhibition of thrombin, but only at very high concentrations), but its inhibitory effect is increased 10,000 fold in the presence of heparin. High concentrations of antithrombin are necessary to prevent shock in animal models of sepsis, according to Büller et al. in *Am. J. Med.* (1989) 87:44-48 and Vinazzer in *Clin. Appl. Thromb/Hemost.* (1995) 1:62-65. Because of the moderate survival time of antithrombin in the circulation (a half-life of about 3 days was reported by Schwartz et al. in *Am. J. Med.* (1989) 87:53-60 and Menache et al. in *Blood* (1990) 75:33-39) and its consumption in SIRS, its activity should be monitored regularly. Theoritically, combined antithrombin and heparin therapy should be more effective than antithrombin alone in the management of shock, but unfortunately this form of treatment did not improve the outcome in shocked patients and was associated with an increased risk of bleeding.

The therapeutically effective amount may herein be defined as an anti-thrombin and/or activated protein C and/or tissue factor pathway inhibitor plasma level restoring amount. Such plasma levels may be easily and directly measured by the person skilled in the art by using methods such as disclosed in Laboratory Haematology (1989), ed. Chanarin, Churchill Livingstone, and in Laboratory techniques in Thrombosis, a manual ($2^{nd}$ revised edition of ECAT assay procedures, Eds Jespersen et al., Kluwer Academic Publishers (1999). It will be appreciated that, in view of the long half-life time of most IgG human antibodies, the partial inhibitors of the present invention being monoclonal antibodies of the said class will provide, in a majority of cases, an efficient prevention and/or treatment with a single administration.

The partial inhibitors of factor VIII with modified glycosylation which are used in the present invention show the following advantages:

they inhibit the function of FVIII to an extent sufficient to reduce, or partially inhibit, the formation of thrombin. Reduction, but not complete suppression, of the formation of thrombin prevents the development of disseminated intravascular coagulation (DIC) while allowing normal clot formation. Preventing DIC maintains normal organ perfusion and avoids organ dysfunction and failure.

keeping the formation of thrombin under control reduces activation of the compensatory anti-inflammatory response. Thus, activated protein C is generated by direct thrombin cleavage and the effect of tissue factor pathway inhibitor is dependent on the presence of activated factor X, the activation of which is directly dependent on factor VIII co-factor activity. Limited depletion of circulating anti-thrombin (AT), which directly combines with thrombin, also occurs. In other words, both the pro-inflammatory and anti-inflammatory compensatory responses are maintained under control by regulating the rate of formation of thrombin.

By modifying the glycosylation of the antibodies of the present invention it is possible to fine-tune the plateau effect, either by using one single antibody which glycosylation pattern, and therefor its inhibitory plateau has been altered, either by using a mixture of antibodies in such a ratio in order to obtain a desired plateau effect which is situated between the plateau effect of the individual compounds. For inflammation induced disorders, the inhibitory antibodies with altered glycosylation, allow to inhibit Factor VIII activity to a level wherein an appropriate balance is obtained between the inhibition of thrombin information and the generation of activated Protein C.

The present invention further provides a pharmaceutical composition for the prevention or treatment of coagulation disorders in animals, more particularly in humans, comprising, as an active ingredient, the antibody and fragments and modified versions thereof with a modified glycosylation pattern and inhibitory activity but unaffected affinity, such as disclosed hereinabove, in admixture with a pharmaceutically acceptable carrier.

Suitable pharmaceutical carriers for use in the pharmaceutical compositions of the invention are described for instance in Remington's Pharmaceutical Sciences 16 ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition.

Control release compositions may be obtained by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active ingredient into particles, e. g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

BRIEF DESCRIPTION OF THE DRAWINGS

The above detailed description, given by way of example, but not intended to limit the invention to specific embodiments described, may be understood in conjunction with the accompanying Figures, incorporated herein by reference, in which.

To remove sialic acid, the native IgG are exposed to sialidase. Upon removal of sialic acids, galactose can be removed by treatement with beta-galactosidase. Following removal of sialic acid and galactose, N-acelylglucosamine can be cleaved by treatment with N-acetyl-beta-D-glucosaminidase. Mannose residues can then be removed by treatment with alpha-mannosidase.

Figure 1:
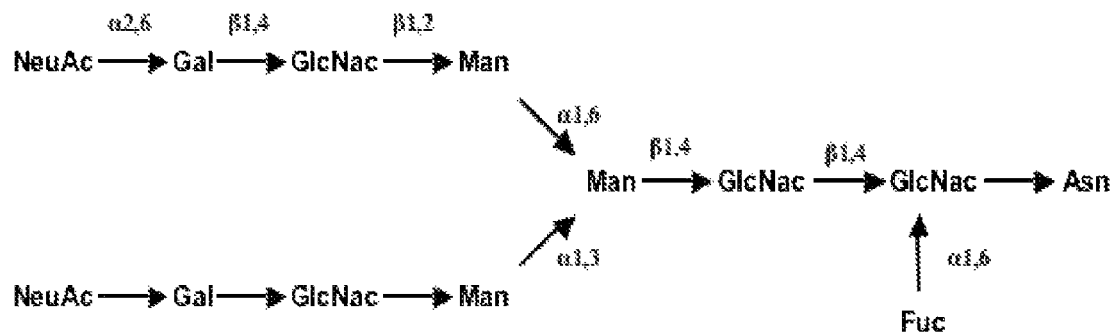
FIG. 1: Schematic representation of the biantennary structure most commonly found in the antigen binding part of antibodies. NeuAc=N-acetylneuramic acid (sialic acid); Gal=galactose; GlcNac=N-acetylglucosamine; Man=mannose; Fuc=fucose; Asn=asparagine.
Figure 2:
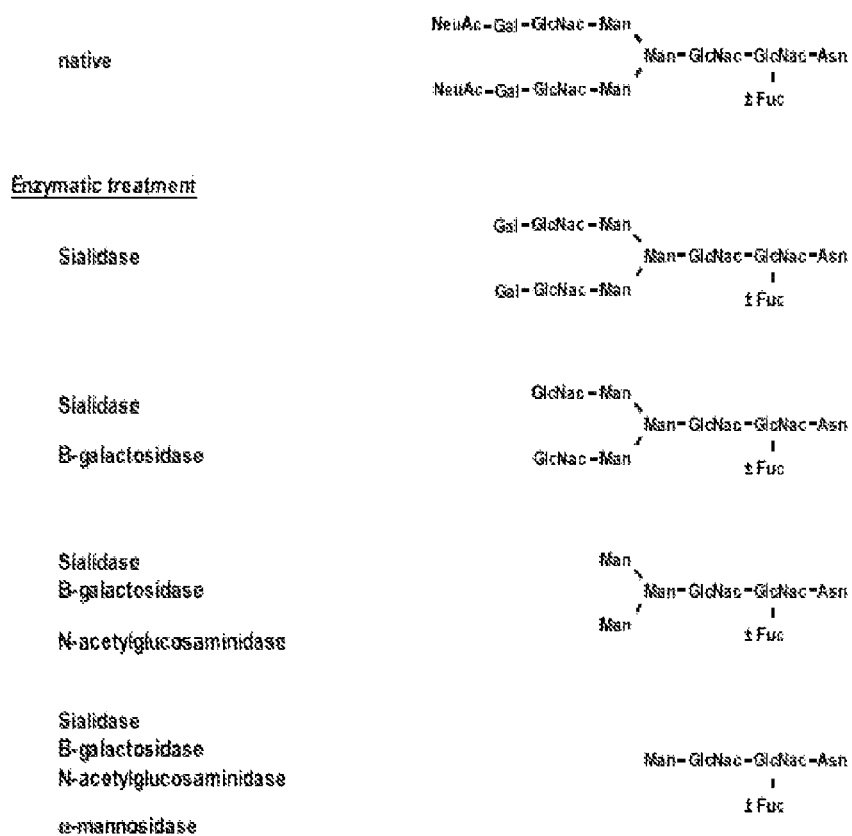
FIG. 2: Schematic representation of the removal of glycan by sequential enzymatic treatment.
Figure 3:
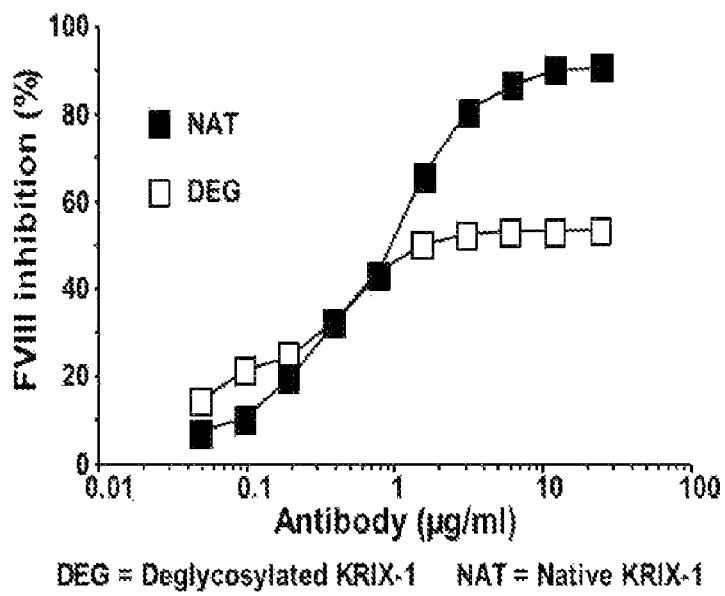

FIG. 3: Graph of experimental results showing the inhibitory activity of native and deglycosylated KRIX-1, in accordance with an embodiment of the invention. KRIX-1 was deglycosylated by treatment with N-glycosidase-F. To assess the inhibitory activity of native (NAT; closed symbol) and deglycosylated KRIX-1 (DEG; open symbol), one volume of antibody at various dilutions was mixed with one volume of a pool of normal human plasma and incubated for 2 h at 37° C. The residual FVIII activity was then measured in a chromogenic assay.

Figure 4:
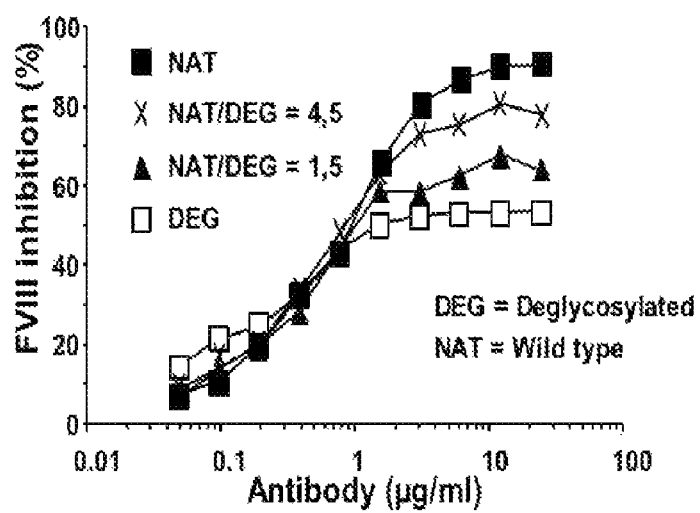

FIG. 4: Graph of experimental results showing that mixing deglycosylated KRIX-1 with native KRIX-1 reduces the maximal "plateau" inhibition of FVIII, in accordance with an embodiment of the invention.

Normal plasma was incubated for 2 h at 37° C. with various concentrations of Krix-1, deglycosylated Krix-1, and mixtures of native and deglycosylated Krix-1 at a ratio of 4.5 and 1.5 native versus deglycosylated antibody. After a 2 h incubation period at 37° C., the residual FVIII activity was measured in a FVIII chromogenic assay.

Figure 5:
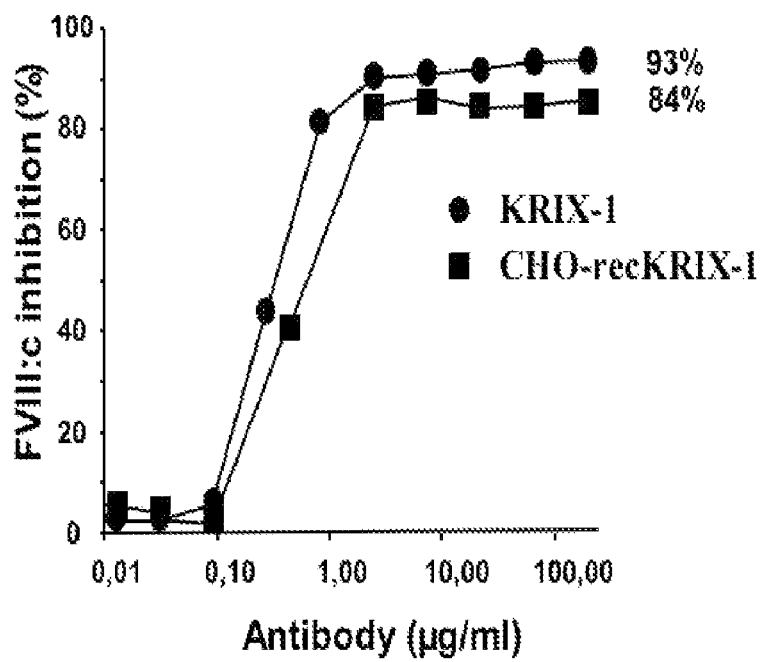

FIG. 5: Graph of experimental results showing the inhibitory activity of CHO-recKRIX-1 and KRIX-1 on FVIII activity in plasma, in accordance with an embodiment of the invention.

To assess the inhibitory activity of the antibody produced by the human cell line (KRIX-1) and the recombinant antibody produced in CHO (CHO-recKRIX-1), one volume of antibody at various dilutions was mixed with one volume of a pool of normal human plasma and incubated for 2 h at 37° C. The residual FVIII activity was then measured in a chromogenic assay.

Figure 6:
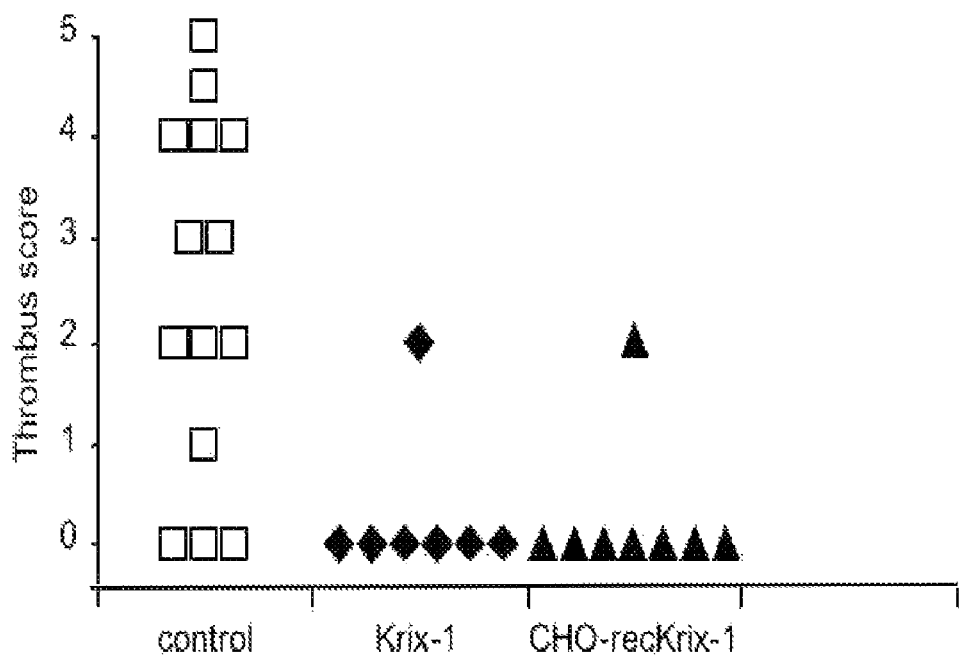

FIG. 6: Graph of experimental results showing the effect of KRIX-1 and CHO-recKRIX-1 on vena cava thrombosis in mice, in accordance with an embodiment of the invention.

Thrombus was induced in the inferior vena cava 16 hours after subcutaneous administration of 150 microgram KRIX-1 and CHO-recKRIX-1 or saline. Animals were sacrificed after 4 hours. Five transverse segments at 0.5 mm intervals through the infrarenal vena cava were scored 1 if thrombus was present or zero if absent, and the scores were summed.

Figure 7:
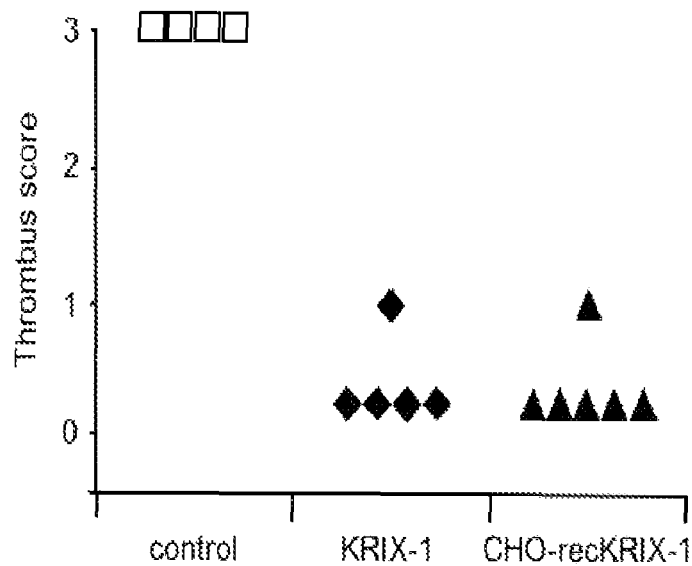

FIG. 7: Graph of experimental results showing that KRIX-1, CHO-rec-KRIX-1 protect against penile thrombosis and priapism in mated $AT^{m/m}$ males, in accordance with an embodiment of the invention.

Males were injected twice subcutaneously with vehicle (PBS), or with 100 microgram antibody mAb Krix-1 or rec-mAB Krix-1, three days before and on the day of mating. Thrombotic outcome was scored zero if the mice were free of thrombosis at the end of the 8-day follow-up, 1 if microscopic thrombosis without priapism was observed, 2 if macroscopic thrombosis without priapism occurred, and 3 if the males developed severe thrombosis with irreversible priapism. (#) One mouse each in the mAb Krix-1 or rec-mAb Krix-1 treated group was free of macroscopic thrombosis at the end of the experiment but could not be analyzed by microscopy and were therefore scored 1.

Figure 8:
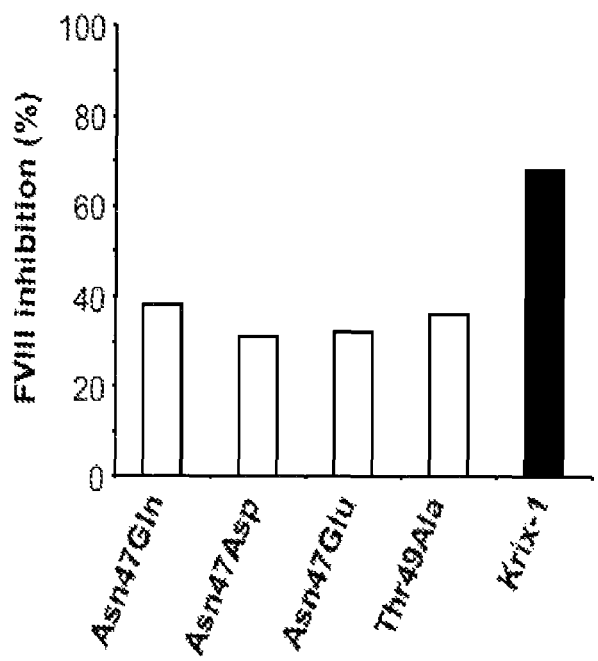

FIG. 8: Graph of experimental results showing the inhibitory activity of CHO-recKRIX-1 and mutated antibodies with N-glycosylation site in the variable region, in accordance with an embodiment of the invention.

To assess the inhibitory activity of the antibodies, one volume of antibody at various dilutions was mixed with one volume of a pool of normal human plasma and incubated for 2 h at 37° C. The residual FVIII activity was then measured in a chromogenic assay.

Figure 9:
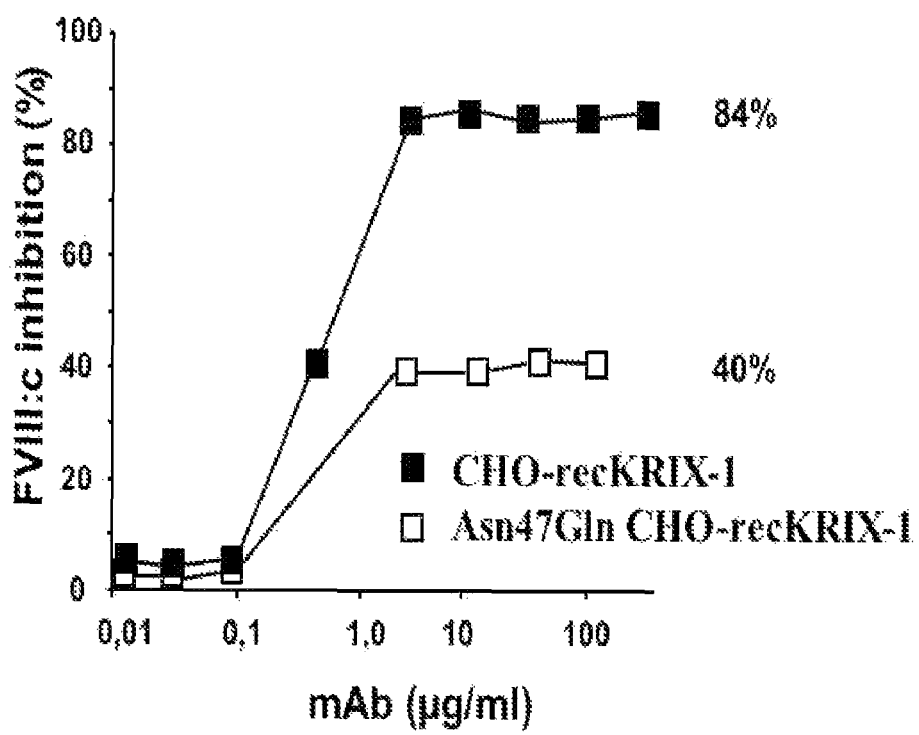

FIG. 9: Graph of experimental results showing the inhibitory activity of CHO-recKRIX-1 and CHO-recKRIX-1Q, in accordance with an embodiment of the invention.

To assess the inhibitory activity of the antibodies, one volume of antibody at various dilutions was mixed with one volume of a pool of normal human plasma and incubated for 2 h at 37° C. The residual FVIII activity was then measured in a chromogenic assay.

Figure 10:
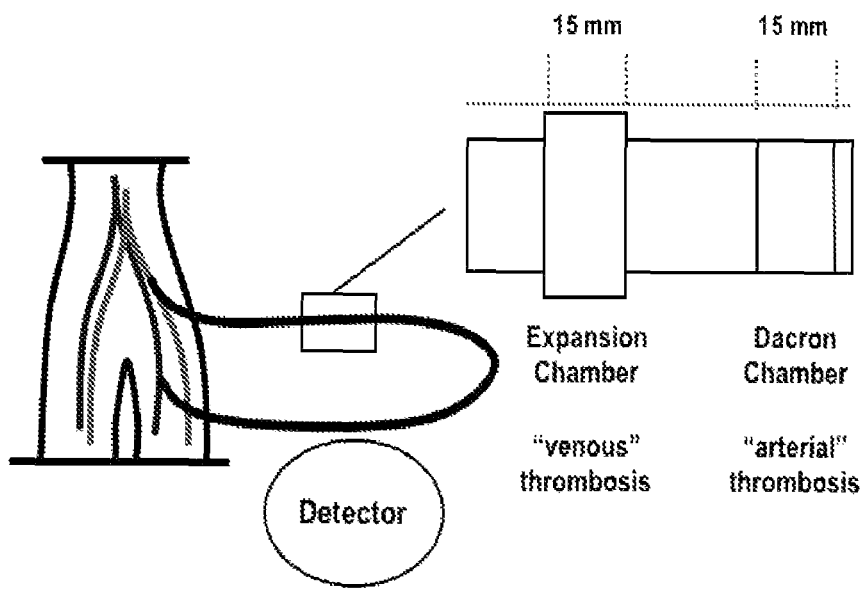

FIG. 10: Drawing representing the experimental protocol for extracorporeal thrombosis in baboons. Arterial and venous thrombogenic devices. Arteriovenous shunts were implanted in male baboon femoral vessels. Thrombogenic devices prefilled with saline were incorporated as extension segments into the permanent arteriovenous shunt. Platelet-dependent arterial thrombus was induced by inserting Dacron into the wall of Silastic tubing. Coagulation-dependent venous thrombosis was generated in an expansion chamber. The deposition of autologous radiolabeled platelets was followed with a gamma scintillation camera.

Figure 11:
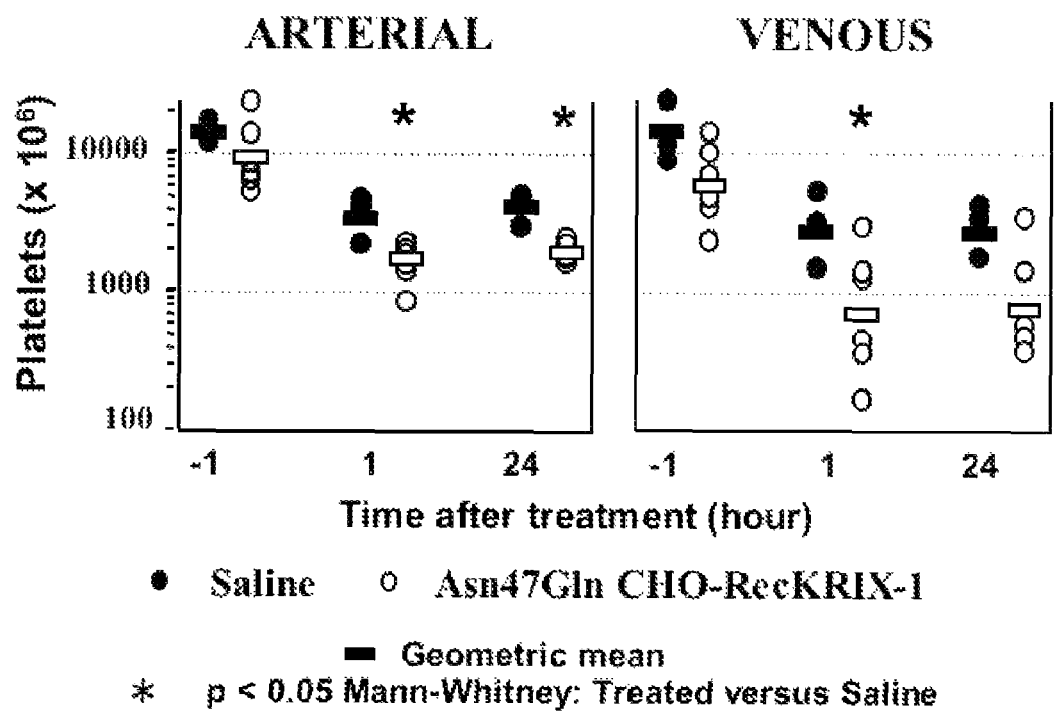

FIG. 11: A graph of experimental results showing the inhibition of platelet deposition in the arterial and venous thrombosis chambers before and after administration of CHO-recKRIX-1Q, in accordance with an embodiment of the invention.

Platelet deposition was recorded as a function of time in the expansion ("venous") thrombosis chamber (A) and in the Dacron ("arterial") thrombosis chamber (B) incorporated in an extracorporeal arteriovenous shunt implanted between femoral vessels. In the control studies, the devices were kept in place for 60 min or until occlusion of the catheter. The baboons were then treated with a single intravenous bolus of antibody. New thrombogenic devices were placed then for 60 minutes, 1 h, 24 h after the bolus injection. The extracorporeal shunts were then removed.

Figure 12:
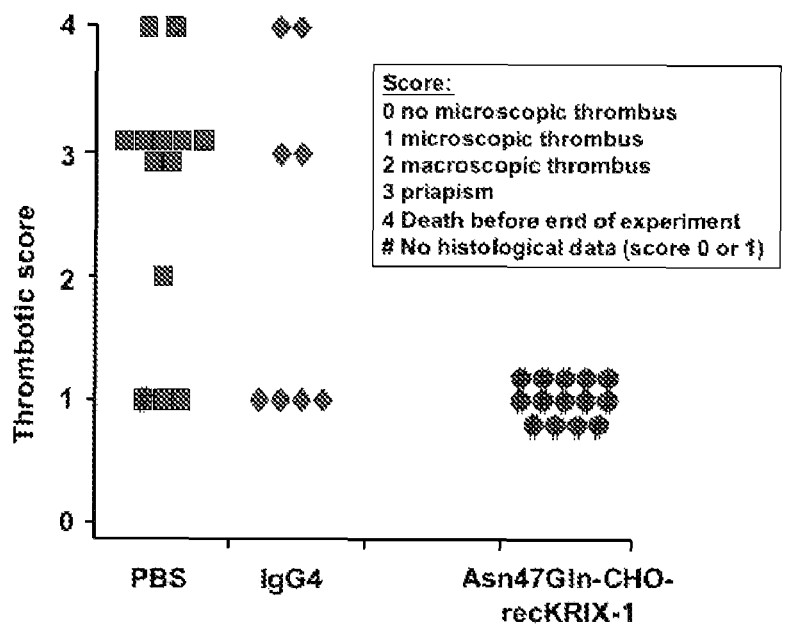

FIG. 12: Graph of experimental results showing that CHO-recKRIX-1Q protects against penile thrombosis and priapism in mated $AT^{m/m}$ males, in accordance with an embodiment of the invention.

Males were injected twice subcutaneously with vehicle (PBS), or with 100 g antibody CHO-recKRIX-1Q or a control IgG4 human monoclonal antibody (IgG4), three days before and on the day of mating. Thrombotic outcome was scored zero if the mice were free of thrombosis at the end of the 8-day follow-up, 1 if microscopic thrombosis without priapism was observed, 2 if macroscopic thrombosis without priapism occurred, and 3 if the males developed severe thrombosis with irreversible priapism. (#) Animals free of macroscopic thrombosis at the end of the experiment but which could not be analyzed by microscopy were scored 1.

Figure 13:
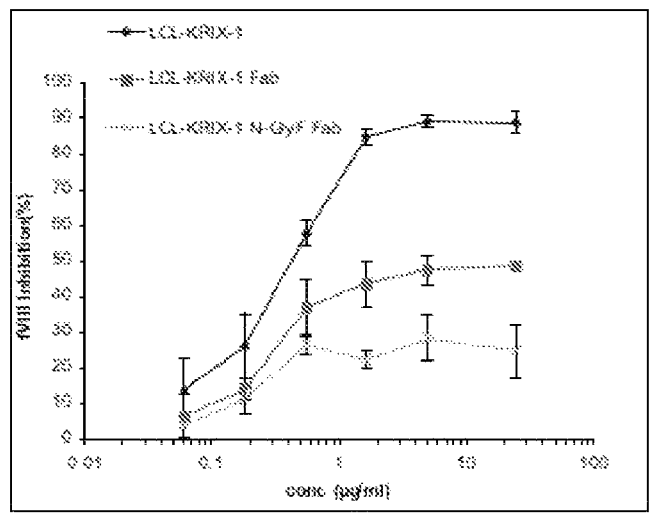
Figure 13:
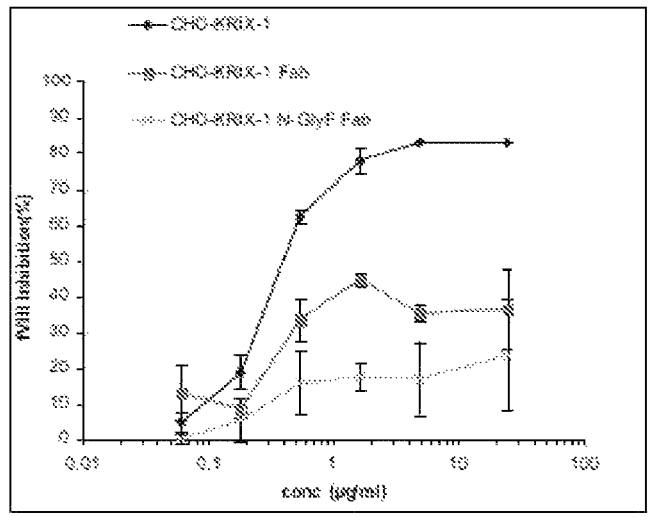

FIG. 13: Graph of experimental results showing the inhibitory activity of native and deglycosylated Fab fragment of LCL-KRIX-1 and CHO-KRIX-1, in accordance with an embodiment of the invention.

KRIX-1 was deglycosylated by treatment with N-glycosidase-F and Fab were produced by digestion with papain. To assess the inhibitory activity of intact antibodies and native and deglycosylated Fab, one volume of antibody at various dilutions was mixed with one volume of a pool of normal human plasma and incubated for 2 h at 37° C. The residual FVIII activity was then measured in a chromogenic assay.

Figure 14:
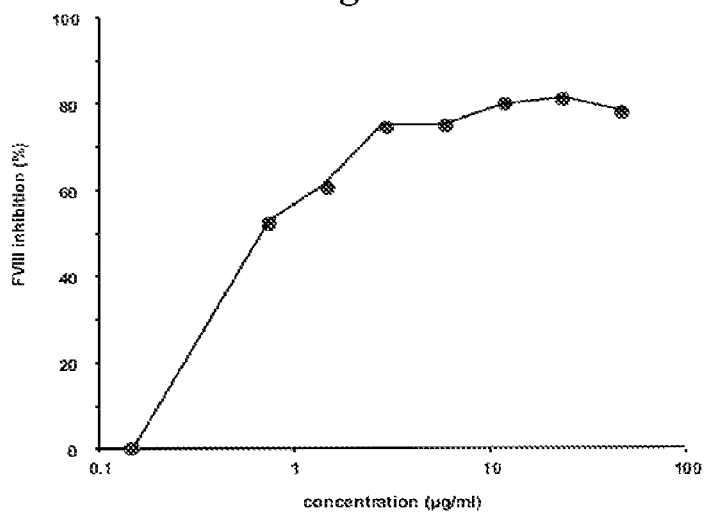

FIG. 14: Graph of experimental results showing the FVIII inhibitory activity of scFv fragment of KRIX-1 (scFv-KRIX-1VLVH(His)) produced in *Pichia pastoris*, in accordance with an embodiment of the invention.

To assess the inhibitory activity of scFv-KRIX-1VLVH (His), one volume of buffer with scFvKRIX-1VLVH(His) at various concentrations was mixed with one volume of a pool of normal human plasma and incubated for 2 h at 37° C. The residual FVIII activity was then measured in a chromogenic assay.

Figure 15:
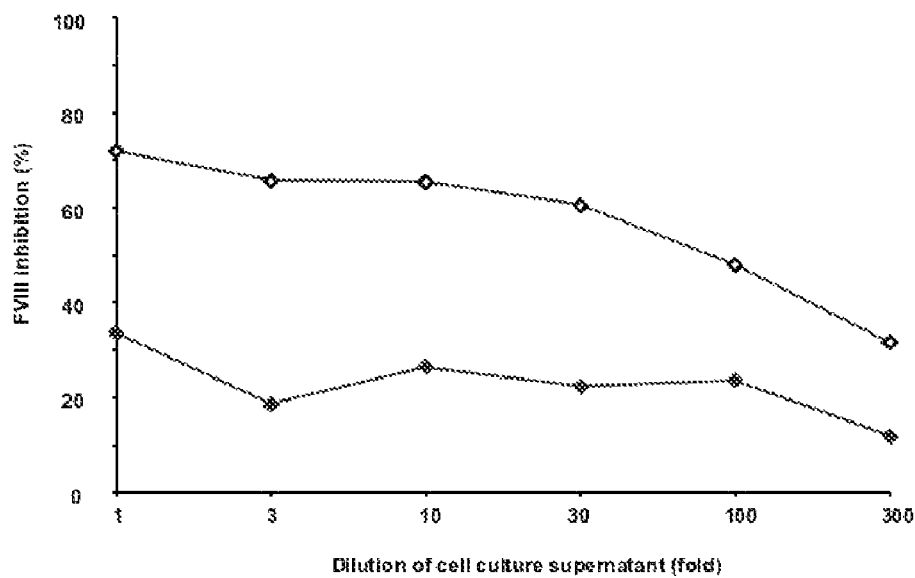

FIG. 15: Graph of experimental results showing the FVIII inhibitory activity of scFv fragment of KRIX-1 and KRIX-1Q, in accordance with an embodiment of the invention.

To assess the inhibitory activity of scFv fragment of KRIX-1 and KRIX-1Q, one volume of culture supernatant of CHO cells, transfected with an expression vector for scFv-KRIX-1VLVH(His) (open symbols) or scFv-KRIX-1VLVHQ(His) (closed symbols), at various dilutions was mixed with one volume of a pool of normal human plasma and incubated for 2 h at 37° C. The residual FVIII activity was then measured in a chromogenic assay.

Figure 16:
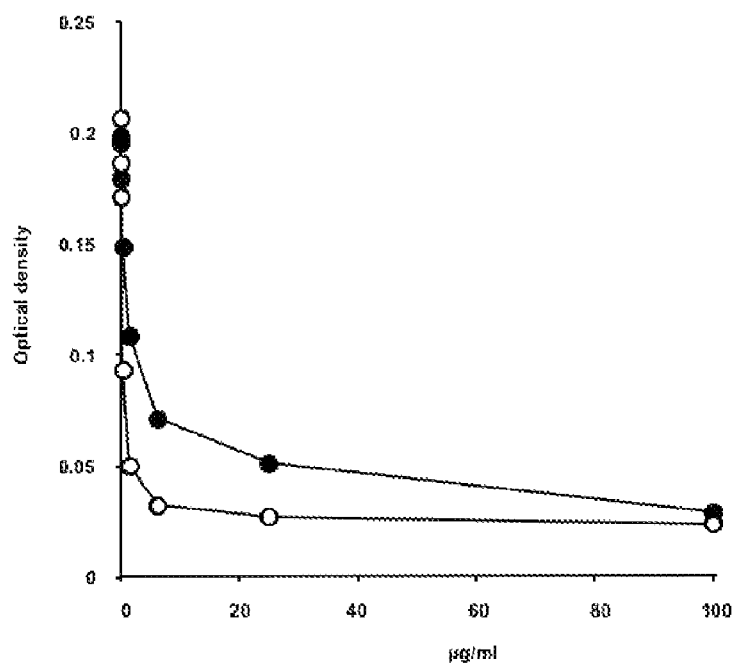

FIG. 16: Graph of experimental results showing the inhibition of FVIII binding to RHD5 by Krix-1 and RHD5.

Biotinylated rFVIII was mixed with different concentrations of RHD5 (closed symbols) or Krix-1 (open symbols) before addition to RHD5 coated plates. The plates were then incubated for 2 hours at 4° C. and the binding of FVIII was detected by the addition of avidine peroxidase and OPD.

FIG. 17: nucleotide and amino acid sequence of Krix-1 variable heavy and light chain (Asn and Thr residues of the glycosylation consensus site are indicated with an asterisk).

FIG. 18: nucleotide and amino acid sequence of scFv fragment of Krix-1Q. The mutated Gln47 residue is indicated.

FIG. 19: nucleotide and amino acid sequence of RHD5 variable heavy and light chain (Asn and Thr residues of putative glycosylation consensus sites are indicated with an asterisk).

EXAMPLES

The present invention will now be described with reference to the following specific, non-limiting examples.

Example 1

Effect of Deglycosylation on FVIII Inhibition by Krix-1

KRIX-1 (0.5 mg/ml in PBS) was mixed with N-glycosidase-F (roche diagnostics Gmbh, Mannheim, Germany) at final concentration of 2 U/ml. The mixture was incubated at 37° C. during 72 hours under gentle stirring.

The inhibitory activity of native and deglycosylated KRIX-1 was assessed in a Bethesda assay (Kasper et al. (1975), cited supra). Therefore, one volume of antibody at various dilutions in TBS (Tris 20 mM, NaCl 0.15 M, pH 7.4) was mixed with one volume of a pool of normal human plasma and incubated for 2 h at 37° C. The pool of normal plasma had been constituted by mixing plasma from 10 normal individual and buffered by addition of Hepes (100 mM) to a final concentration of 10 mM. The residual FVIII activity was then measured using a modification of the DADE FVIII chromogenic assay (Dade A G, Marburg, Germany). In this assay, thrombin-activated FVIII accelerates the conversion of factor X into factor Xa in the presence of factor IXa, PL and calcium ions; factor Xa activity is then assessed by hydrolysis of a p-nitroanilide substrate. Reagents, which were reconstituted according to the manufacturer's instruction, comprised bovine factor X (1 mM), factor IXa (0.3 mM) and thrombin (0.3 mM); CaCl2 (30 mM), PL (60 mM), a chromogenic factor Xa substrate ($CH_3OCO$-D-CHG-Gly-Arg-pNA.AcOH; 3.4 mM), and a thrombin inhibitor (L-amidinophenylalanine piperidine). Aliquots of 30 µl of plasma/antibody mixture were retrieved at the end of the 2 h incubation period and displayed in microtitration plates; 30 µl of the factor X and factor IXa/thrombin reagents were added sequentially. After 90 sec, 60 µl of the chromogenic substrate were added and the incubation extended for 10 min at 37° C. The reaction was then blocked by addition of 30 µl citric acid (1 M), and OD was measured at 405 nm. The residual FVIII activity was determined by comparing the $OD_{405\ nm}$ of test samples with that obtained with FVIII solutions of known concentrations. The residual FVIII activity was expressed as the percentage of activity measured in plasma aliquots handled and diluted exactly as test samples throughout the entire experiment.

Native KRIX-1 inhibited up to 90% of FVIII activity. By contrast, a maximal inhibition (plateau inhibition) of only 50% was achieved with deglycosylated KRIX-1 (FIG. 3).

Example 2

Mixing Native and Deglycosylated KRIX-1 Allows the Selection of Antibody Mixtures Inhibiting FVIII to Different Levels Mixtures containing different ratio of deglycosylated with N-glycosidase-F versus native KRIX-1 were prepared. Each mixture was diluted to various antibody concentrations ranging between 0.05 and 25 microgram/ml. One volume of each dilution was mixed with one volume of a pool of normal human plasma. After 2 hours period incubation at 37° C., the residual FVIII was assesed using a chromogenic assay (Factor VIII Chromogenic assay, Dade Behring, Marburg, Germany). The native and deglycosylated KRIX-1 inhibited FVIII activity by about 90% and 50%, respectively (FIG. 4). By contrast, a mixture of 4.5 native antibody for 1 deglycosylated antibody resulted in a maximal FVIII inhibition of about 80% whereas a mixture containing 1.5 native KRIX-1 for 1 native antibody inhibited about 65% FVIII activity (FIG. 4). Mixtures inhibiting FVIII activity to any level comprised between 50 and 90% can be similarly obtained by varying the ratio of native and deglycosylated KRIX-1.

Example 3

Recombinant Krix-1 Produced in CHO Cells (CHO-recKRIX-1) has a Lower FVIII Inhibitory Activity than Krix-1 (Produced by a Human Lymphoblastoid Cell Line)

RNA from KRIX-1 EBV-immortalised human B cells was isolated using TRIzol Reagent according to the manufacturer's instructions (Life Technologies). cDNA was synthesised with the SuperScript pre-amplification system for first-strand cDNA synthesis.

The sequences encoding the heavy or light chain were amplified by RT.PCR on mRNA prepared from KRIX-1 cells using the QuickPrep®Micro mRNA Purification Kit (Amersham Pharmacia Biotech, Rosendaal, The Netherlands). Specific PCR primers for the heavy chain were: forward primer 5'-cggggtacc ccacc ATGGACTGGACCTGGAGGATC-3' (SEQ ID NO:5) corresponding to nucleotides (nt) 1 to 21 (in capitals) of the cDNA sequence (WO 01/04269 A1), and containing a KpnI site (underlined) for cloning purposes and a Kozak sequence (bold italic); reverse primer: 5'-tatggccgac gtcgac tcaTTTACC-CGGAGACAGGGAGAG-3' (SEQ ID NO: 6) corresponding to nt 1800-1780 (capitals) of the 3' end of the human gamma-4 constant region (accession number K01316) and containing a stop codon (bold italic) and a SalI site (underlined) for cloning purposes. Specific primers for the light chain were: forward primer 5'-cccaag ctt ccacc ATGGAAACCCCAGCKCAGCT-3' (SEQ ID NO: 7) corresponding to nt 1-20 (capitals) of the cDNA sequence (WO 01/04269 A1), and containing a HindIII site (underlined) for cloning purposes and a Kozak sequence (bold italic); reverse primer: 5'-aaacagcctctaga ctaACACTCTC-CCTGTTGAAG-3' (SEQ ID NO: 8) corresponding nt 653-635 of the 3' end of the human kappa constant region (accession number V00557) and containing a stop codon (bold italic) and a XbaI site (underlined) for cloning purposes. After sequence verification, the heavy and light chain sequences were cloned consecutively into the pBudCE4 plasmid (Invitrogen, Merelbeke, Belgium) designed for double gene expression in eukaryotic cells under the control of the EF1-alpha and the CMV promoter, respectively, using the above indicated restriction sites. The final vector was used for stable transfection of CKO-K1 cells using the FuGENE6 system (Roche Diagnostics, Brussels, Belgium) according to the manufacturer's instructions. The transfected cells were cultured in DMEM (Life Technologies, Paisley, UK) supplemented with 10% FCS, 4 mmol/L glutamine and 80 mg/L gentamicine (Geomycin®, Schering-Plough, Heist-op-den-Berg, Belgium) in the presence of zeocin (0.7 mg/mL selection concentration or 0.35 mg/mL maintenance concentration; Life Technologies, Invitrogen), and were verified for antibody production by ELISA (see below). The cells were adapted to growth in serum-free medium by step-wise reduction of the FCS to 0%, and after clonal dilution, the best producer in terms of functionality (ELISA on huFVIII), as well as expression (ELISA with anti-human IgG4 detection antibody), was used for batch production. For detection of anti-FVIII antibodies, rFVIII was insolubilised by incubating plates for 2 h at 4° C. directly with 50 µl of rfVIII (1 microgram/ml) diluted in glycin-buffered saline (GBS). The plates were washed as above and 50 µl of culture supernatant were added for a further incubation of 2 h at 4° C. After washing, 50 µl peroxidase-labelled anti-human Fc gamma goat IgG (Sigma) diluted 1000-fold in Tris-casein were added. After 2 h at RT, the plates were washed again and supplemented with 100 µl OPD. The resulting OD was read at 492 nm in a Emax Microplate Reader (Molecular Devices, Menlo Park, Calif.). Negative and positive controls were culture medium and IgG purified from a high-titer inhibitor hemophilia A patient, respectively.

The recombinant antibody was purified from the cell culture supernatant by adsorption on immobilized protein A (High-TRAP Protein A, Pharmacia, Uppsala, Sweden). Culture supernatant was passed through a high-TRAP$^R$ protein A (Pharmacia, Uppsala, Sweden) at a flow rate of 1 ml/min. Bound IgG was eluted with citric acid 100 mM, pH3. After pH neutralisation with Tris pH9, IgG was dialysed against Phosphate buffered saline (PBS). The concentration of proteins was determined with the Bio-Rad assay (Biorad).

The recombinant antibody produced in CHO cells was called CHO-recKRIX-1. Interestingly, the maximal inhibition observed in large excess of this antibody reaches only 75-85% FVIII activity, which is lower than the 85-95% maximal (plateau) inhibition observed when FVIII is incubated with KRIX-1 (produced by the human lymphoblastoid cell line (FIG. 5).

Example 4

Prevention of Vena Cava Thrombosis Using CHO-recKRIX-1 in Mice

Thrombus was produced in the inferior vena cava of adult male wild-type mice (weight 18 g-31 g, age 8-10 weeks) using a previously described model (Singh et al. 2002 cited supra). Mice were anaesthetised with isoflurane, the inferior vena cava was exposed below the renal veins via a median laparotomy and a neurosurgical vascular clip (Braun Medical) was applied for 15 seconds on two occasions, 30 seconds apart to a segment of the vena cava. A 5/0 prolene thread was then placed alongside the vena cava and a stenosis produced by tying a 4/0 silk suture around the vena cava and the prolene thread. The thread was removed to allow blood flow to resume. The abdomen was closed and the animal allowed to recover. After 4 hours, the mice were reanaesthetised and a 1 cm portion of the inferior vena cava (between the point of ligature and iliac bifurcation) was excised and examined for the presence of thrombus. The excised segments were then washed in 10% PBS and soaked overnight in 1% paraformaldehyde. Vessel segments were embedded in paraffin wax and 7×10 µm transverse sections were cut at 0.5 mm intervals from the ligature down.

Sections were stained by haematoxylin and eosin, Martius Scarlet Blue (MSB) and a rabbit anti-platelet antibody (Accurate Chemical & Scientific Corporation, Westbury, N.Y. 11590). MSB stains fresh fibrin red or mature fibrin blue/gray, red cells yellow and collagen bright blue. Thrombus size was measured by scoring the 7 sections for the presence of thrombus, giving a score of 1 for the presence and 0 for the absence of thrombus in each. Scores were then added up for each animal. The investigators performing the operations and the microscopic analyses were blinded towards treatment groups.

Thrombosis was induced in three groups of wild-type mice 16 hours after subcutaneous injection of 150 microgram of antibody or saline. The statistical significance of differences between groups was evaluated on the presence or absence of thrombus using Fisher's exact test (2-sided). The effects on thrombus size were tested by comparing thrombus scores using the Mann-Whitney U test. Ten out of 14 mice injected with saline developed a thrombus, visible macroscopically, compared with 0 out of the 7 animals in each of the groups pretreated with either KRIX-1 or CHO-recKRIX-1 ($P<0.01$).

Histological analysis identified thrombi in 11 out of 14 control animals and 1, 1, and 2 thrombi, respectively, in animals treated with KRIX-1 or CHO-recKRIX-1 (FIG. 6). Accordingly, although CHO-recKRIX-1 inhibits FVIII activity significantly less than KRIX-1, CHO-recKRIX-1 inhibits very efficiently thrombosis and therefore offers a better safety/efficacy profile than the native KRIX-1 antibody.

Example 5

Antithrombotic Activity of CHO-recKRIX-1 in Mice with Type II Heparin Binding Site (HBS) Antithrombin Deficiency ($AT^{m/m}$)

The antithrombotic efficacy of CHO-recKRIX-1 was evaluated using the thrombotic priapism model in mice with type II heparin binding site (HBS) antithrombin deficiency (Dewerchin et al. submitted).

The mice were previously generated by targeted knock-in of an R48C mutation (corresponding to the "Toyama" R47C mutation in man, abolishing heparin/heparan sulphate binding and cofactor activity (Koide et al. (1983) *Thromb Res.* 31, 319-328; Koide et al. (1984) *Natl. Proc Natl Aced Sci USA.* 81, 289-293) in the HBS of antithrombin (AT) ($AT^{m/m}$ mice), resulting in life-threatening, spontaneous thrombosis at different sites, most prominently in the heart, liver, and in ocular, placental and penile vessels (Dewerchin et al, submitted for publication). The observation of priapism occurrence upon mating of males $AT^{m/m}$ provided the basis to the development of a physiological model of venous thrombosis, providing a defined endpoint and an easy grading of the thrombotic outcome.

Age-matched groups of sexually mature males (2 to 4 months) were subcutaneously injected twice (three days before mating and on the day of mating) with 100 µl of saline or with 100 µl of a 1 mg/ml solution of Krix-1, CHO-recKRIX-1Q or CHO-recKRIX-1. After the second injection, each male was mated to two wild type Swiss females, which were replaced by two new females on day 3 after mating. The formation of a vaginal mucus plug indicating recent mating was recorded daily for all females, and only the results obtained with males with confirmed sexual activity were incorporated in the analysis. Males were examined daily for development of priapism and were sacrificed when priapism was observed, or at day 8 after initial mating when the experiment was ended. At sacrifice, blood samples were collected for determination of residual FVIII activity and human IgG levels as described above. The penises were dissected and the presence of thrombus IN the dorsal penile vein and corpora cavernosae determined by visual inspection.

After sacrifice, the dissected penises were paraformaldehyde fixed, parafin-embedded and processed for histological analysis. Seven-µm transverse sections were stained with haematoxylin/eosin for microscopic analysis.

Scoring: Thrombotic outcome was scored using four categories: 0, no thrombosis; 1, thrombosis of the penile vein by microscopy; 2, macroscopically visible thrombosis of the penile vein; 3, irreversible thrombotic priapism. When no macroscopically visible thrombus was observed and no histology of the penile vein could be obtained for technical reasons, the animals were also scored 1. The investigators performing the injections and monitoring the mice were blinded towards the treatment groups. The statistical significance of differences between thrombus scores was tested using the Kruskal-Wallis or Mann-Whitney U test. The presence of a vaginal mucus plug in at least 2 females within the follow-up period for each these males treated with antibody or saline, confirmed actual sexual activity of the males.

KRIX-1, CHO-rec-KRIX-1 were able to prevent priapism in all mice tested (p<0.05 versus saline) (FIG. 7). In the group injected with 2×100 g KRIX-1 antibody, none of the five males developed priapism; four of them were also free of thrombosis upon visual inspection and by microscopic analysis at the end of the experiment; the remaining male did not show macroscopic thrombosis. For technical reasons, no histological analysis could be performed and the animal was therefore scored 1 (FIG. 7), the maximal score which could have been attributed if the analysis had been performed.

A similar outcome was observed for the recombinant CHO-rec-KRIX-1 antibody: none of seven treated males developed priapism; five males were also free of macroscopic or microscopic thrombosis (FIG. 7); one male showed only microscopically detectable thrombosis (score 1) (FIG. 7) and one male was free of macroscopically visible thrombosis but could not be analyzed by microscopy and was therefore also scored 1 (FIG. 3).

Example 6

Antithrombotic Activity of CHO-recKRIX-1Q in Mice with Type II Heparin Binding Site (HBS) Antithrombin Deficiency ($AT^{m/m}$)

As outlined in example 5, the antithrombotic efficacy of CHO-recKRIX-1Q was evaluated using the thrombotic priapism model in mice with type II heparin binding site (HBS) antithrombin deficiency (Dewerchin et al. (2003) *Circ Res* 93, 1120-1126).

In the present example, age-matched groups of sexually mature males were subcutaneously injected twice (three days before mating and on the day of mating) with 100 µl of saline or with 100 µl of a 1 mg/ml solution of CHO-recKRIX-1Q, a control human IgG4 monoclonal antibody, which does not recognise FVIII, or the vehicle (PBS).

CHO-recKRIX-1 was able to reduce thrombosis development (p<0.05 versus PBS and control IgG4) (FIG. 12). In the group injected with 2×100 microgram CHO-recKRIX-1Q antibody, none of the males died or developed priapism. All animals treated with CHO-recKRIX-1Q were also free of thrombosis upon visual inspection For technical reasons, no histological analysis could be performed and the animal were therefore scored 1 (FIG. 12), the maximal score which could have been attributed if the analysis had been performed. By contrast, in the groups treated with PBS or a control human IgG4 monoclonal antibody, several animals died or developed priapism (p<0.01, CHO-recKRIX-1Q versus PBS and control IgG4).

Example 7

Production and Characterisation of Variant of CHO-recKRIX-1 Devoid of N-Glycosylation Site in the Antigen Binding Site CHOrecKrix-1Q was produced by site directed mutagenesis on the pCR4-Blunt-TOPO-Krix-1H plasmid resulting in a single amino acid change in the heavy chain altering the Asn47 into Gln47 in order to disrupt the N-linked glycosylation site at Asn47-Thr49. Other plasmids comprising the coding sequence of the krix-1 antibody can similarly be used in the context of the present invention. Amino acid sequences comprising the CDRs of the heavy and light chains of Krix-1 are provided in SEQ ID NO:2 and SEQ ID NO: 4 respectively. Nucleotide sequences encoding sequences of the CDRs of the heavy and light chains of Krix-1 are provided in SEQ ID NO:1 and SEQ ID NO: 3 respectively.

The mutagenesis at Asn47 was obtained using the Site Directed Mutagenesis Kit (Stratagene, La Jolla, Calif.) in combination with the following specific PCR primers:

(SEQ ID NO: 9)
Forward primer:
5'-CCTGCAAGACCTCTGGATAC cAaTTCACCGGCTACTCTGCT

TCTGG-3' corresponding to nt 119 to 164 of the Krix-1 Heavy chain sequence (capital) containing two altered nucleotides (a to c and c to a; bold italic);

(SEQ ID NO: 10)
Reverse primer:
5'-CCAGAAGCAGAGTAGCCGGTGAA tTgGTATCCAGAGGTCTT

GCAGG-3' corresponding to nt 119 to 164 of the Krix-1 Heavy chain sequence (capital) containing two altered nucleotides (g to t and t to g; bold italic) CHO-recKrix-1A was produced by site directed mutagenesis resulting in a single amino acid change altering Thr49 into Ala49 in order to disrupt the N-linked glycosylation site at Asn47-Thr49

This was obtained using the Site Directed Mutagenesis Kit (Stratagene, La Jolla, Calif.) in combination with the following specific PCR primers:

(SEQ ID NO: 11)
Forward primer:
5'-CCTCTGGATACAACTTC gctGGCTACTCTGCTTCTGG-3' corresponding to nt 128 to 164 of the Krix-1 Heavy chain sequence (capital) containing two altered nucleotides (a to g and c to t; bold italic);

(SEQ ID NO: 12)
Reverse primer:
5'-CCAGAAGCAGAGTAGCC aGcGAAGTTGTATCCAGAGG-3' corresponding to nt 128 to 164 of the KRIX-1 Heavy chain sequence (capital) containing two altered nucleotides (g to a and t to c; bold italic);

CHO-recKrix-1E was produced by site directed mutagenesis resulting in a single amino acid change altering Asn47 into Glu47 in order to disrupt the N-linked glycosylation site at Asn47-Thr49

(SEQ ID NO: 13)
Forward primer:
5'-CCTGCAAGACCTCTGGATAC gAgTTCACCGGCTACTCTGCT

TCTGG-3' corresponding to nt 119 to 164 of the Krix-1 Heavy chain sequence (capital) containing two altered nucleotides (a to g and c to g; bold italic);

(SEQ ID NO: 14)
Reverse primer:
5'-CCAGAAGCAGAGTAGCCGGTGAA cTcGTATCCAGAGGTCTT

GCAGG-3' corresponding to nt 119 to 164 of the Krix-1 Heavy chain sequence (capital) containing two altered nucleotides (g to c and t to c; bold italic). CHO-recKrix-1D was produced by site directed mutagenesis resulting in a single amino acid change altering Asn47 into Asp47 in order to disrupt the N-linked glycosylation site at Asn47-Thr49.

(SEQ ID NO: 15)
Forward primer:
5'-CCTGCAAGACCTCTGGATAC gACTTCACCGGCTACTCTGCTTCTGG-

3' corresponding to nt 119 to 164 of the Krix-1 Heavy chain sequence (capital) containing one altered nucleotide (a to g; bold italic);

(SEQ ID NO: 16)
Reverse primer:
5'-CCAGAAGCAGAGTAGCCGGTGAAGT cGTATCCAGAGGTCTTGCAGG-

3' corresponding to nt 119 to 164 of the Krix-1 Heavy chain sequence (capital) containing one altered nucleotide (t to c; bold italic)

After sequence verification, the mutated heavy and wild-type (native) Krix-1 light chain were cloned into the pEE6.4 and pEE14.4 vector (Lonza Biologics, Portsmouth, N.H.) respectively. The two vectors were combined to a double gene vector—containing both heavy and light chain—using the NotI and SalI restriction sites present in both vectors. Heavy and light chain expression in eukaryotic cells is under the control of the hCMV-MIE promoter (present in pEE14.4 and pEE6.4). The double gene vector was linearised with SalI before transfection.

The linearised vector was used for stable transfection of CKO-K1 cells using the FuGENE6 transfection reagent (Roche, Brussels, Belgium) according to the manufacturer's instructions. The transfected cells were cultured in glutamine-free DMEM (JRH Biosciences, Lenexa, Kans.) supplemented with FBS 10%, GS Supplement (JRH Biosciences, Lenexa, Kans.) and 25 µM L-Methionine Sulfoximine (MSX) (Sigma-Aldrich, Bornem, Belgium) for selection.

The best producers were adapted to growth in serum-free medium (EX-CELL 302 serum-free medium w/o L-Glutamine, JRH Biosciences, Lenexa, Kans.)—supplemented with 25 µM MSX and GS Supplement—by step-wise reduction of the FBS to 0%. The best expressing (ELISA with anti-humanIgG4 detection antibody) functional cell line was used for batch production of the mutated rec-mAb-Krix-1, either using the adherent or the suspension cell line.

The recombinant antibody was purified from the cell culture supernatant by affinity chromatography using a HiTrap rProtein A FF column (Amersham Biosciences, Uppsala, Sweden). After concentration the rec-mAb-KRIX-1Q (A, E and D resp.) were assayed for functionality (Chromogenic assay to evaluate the ability of the mutated rec-mAb Krix-1 to inhibit fVIII activity). Inhibitory capacity towards fVIII was compared to that of the wild type rec-mAb Krix-1 (FIGS. 8 and 9). FVIII inhibition by these mutants ranged from 30 to 40%.

Measurement of Surface Plasmon Resonance (SPR).

The rate of FVIII association and dissociation to CHO-rec-KRIX-1Q, CHO-rec-KRIX-1A and native CHO-rec-KRIX-1 was analysed using a Pharmacia Biosensor BIAcore™ instrument (Pharmacia Biosensor AB). Purified antibody (20 microgram/ml in 10 mM sodium acetate buffer pH 5.0) was immobilised on the activated surface of a CM5 sensor chip, according to the manufacturer's instructions. All binding experiments were carried out in HBS at a constant flow rate of 10 µl/min. FVIII in Hepes Buffered Saline (HBS) was infused at various concentrations over the antibody coated on the sensor chip surface. At the end of each cycle, the surface was regenerated by flushing HCl, pH 2, for 36 sec. Control experiments ensured that FVIII bound only to insolubilised antibody. Thus, rFVIII did not bind to the sensor chip in the absence of antibody, and preincubation of rFVIII with soluble antibody prior to addition to the chip completely prevented FVIII binding.

Association and dissociation rate constants were determined by non-linear fitting of individual sensorgram data (O'Shanessy et al. 1993, *Analyt Biochem* 212: 457) using the BIA evaluation 2.1 software (Pharmacia Biotech, Uppsala, Sweden). Values of $k_{ass}$ and $k_{diss}$ were determined by averaging the values obtained for individual curves established with various analyte concentrations. Values of $k_{diss}$ were determined from the individual curves obtained with only the highest analyte concentration, in order to reduce bias due to rebinding of the analyte to free immobilized ligand. All data were analysed after correction of the baseline by subracting the response observed before injection of the analyte (rfVIII) from the response values obtained during the association and dissociation phases.

The dissociation constant ($K_D$) of FVIII from CHO-rec-KRIX-1Q, CHO-rec-KRIX-1A and native CHO-rec-KRIX-1 was very similar (Table 1). Accordingly, the glycosylation site in the antigen binding site of mAb Krix-1 influences the antibody inhibitory activity but does not contribute significantly to binding to FVIII.

TABLE 1 surface plasmon resonance analysis of FVIII binding to mAb Krix-1 and derivative thereof.

| Modified mAb Krix-1 (LCL): | $K_D$ (nM) |
|---|---|
| CHO-recKRIX-1 | 0.14 ± 0.03 |
| CHO-recKRIX-1Q | 0.17 ± 0.02 |
| CHO-recKRIX-1A | 0.13 ± 0.01 |

Example 8

Prevention of Arterial and Venous Thrombosis in Baboons

Methods
Protocol

Male baboons (*Papio ursinus*) were used. The animals weighed between 8 and 17 kg and were disease-free for at least 6 months prior to the experiments. All procedures were approved by the Ethics Committee for Animal Experimentation of the University of the Free State in accordance with the National Code for Animal Use in Research, Education, Diagnosis and Testing of Drugs and Related Substances in South Africa.

Permanent polytetrafluoroethylene (Teflon) and silicone rubber (Silastic) arteriovenous (AV) shunts were implanted in the baboon femoral vessels. Blood flow through the shunts varied between 100 and 120 mL/min. Handling of the baboons was achieved through anesthesia with ketamine hydrochloride (Anaket-V, Centaur Laboratory).

In each experiment, a thrombogenic device prefilled with saline to avoid a blood-air interface was incorporated as an extension segment into the permanent arteriovenous shunt by means of Teflon connectors (Kotze et al. (1983) *Thromb Haemost.* 70, 672-675). Platelet-dependent arterial thrombus was induced by using Dacron inserted into the wall of Silastic tubing (3-mm inside diameter) according to Hanson et al. (1985) *Arteriosclerosis* 5, 595-603 (FIG. 10).

The Dacron vascular graft material (1.26 cm$^2$) served as a generator of platelet-dependent arterial-type thrombosis. An expansion chamber (3.77 cm$^2$) was used to generate coagulation-dependent venous thrombosis. Blood flowed through the thrombogenic devices at a rate of approximately 120 ml/min. The initial shear stress was 318 sec$^{-1}$ for the Dacron section and 10 sec$^{-1}$ for the expansion chamber.

In the control studies, the devices were kept in place for 60 minutes or until they occluded, after which they were removed and blood flow through the permanent AV-shunt re-established. The baboons were then treated with a single intravenous bolus of 1.25 or 5 mg/kg CHO-rec-Krix-1QThe thrombogenic devices were placed for 60 minutes 1 h after antibody injection, after which the devices were removed and blood flow through the permanent AV-shunt reestablished. Additional 60-minute studies were carried at 24 h and 48 h after the antibody bolus injection. The extracorporeal shunts were then removed after the last thrombosis experiment. Blood samples were taken according to the sampling schedule either directly from the shunt or by venopuncture. FVIII activity, mAb Krix-1 concentrations monitored, PT, APTT, fibrinogen, were measured on all samples.

Graft Imaging.

Autologous platelets were labeled with 111In-tropolone and reinjected into the animal 1 h before the start of the control experiment. This allowed image acquisition on day 0, 1 and 2. To provide image acquisition on day 6 or 14 the labeling procedure was repeated. Image acquisition of the grafts was done with a gamma scintillation camera fitted with a high-resolution collimator. The images were stored on and analysed with a computer imaging and analysis system interfaced with the scintillation camera. Dynamic image acquisition, 3-minute image of a 5 ml autologous blood sample were also acquired each time the grafts were imaged to determine blood radioactivity (blood standard). Regions of interest of the graft and expansion segments were selected to determine the deposited and circulation radio-activity in the dynamic image. The total number of platelets deposited on the vascular graft material and in the expansion chamber were calculated.

In 6 animals treated with CHO-rec-KRIX-1E, platelet deposition was lower than in the control animal treated with saline in both the venous and arterial thrombosis chambers (FIG. 11).

Example 9

Treatment of Sepsis Related Conditions with Inhibitory Antibodies Against Factor VIII with Modified Glycosylation Injection of endotoxin elicits the production of pro-inflammatory cytokines among which IL-6 and TNF-α are important for their interactions with the coagulation system. Thus, IL-6 increases the production of tissue factor and, consequently, the generation of thrombin. It also increases the production of fibrinogen by an independent mechanism. TNF-α increases the levels of plasminogen activation inhibitor type I (PAI-1) and thereby reduces fibrinolysis.

Groups of six mice (C57Bl/6) are constituted for each treatment.

Wild type and F VIII knock-out mice are intravenously injected with 30 and 100 microgram of the following antibodies:

no antibody
control antibody (IgG4)
Krix1 antibody expressed in CHO cells (CHO-recKRIX-1)
mutated Krix 1 at Asn47 (CHO-recKRIX-1Q)
(KRIX-1)/(CHO-recKRIX-1Q) in a ¼ or other ratio Other mixtures comprising Krix-1 are envisaged for testing such as mixtures comprising fragments of native or deglycosylated Krix-1 (more particularly, Fab or scFv fragments). Other mixtures comprising Krix-1 and a second antibody (as disclosed in example 13) or derivatives thereof are also considered. A particular mixture comprises Krix-1 and RHD5 or fragments of Krix-1 and/or RHD5.

60 minutes after the administration of the antibody, the different mouse population are injected intraperitoneously with either microgram4 microgram or 40 microgram or 400 microgram lipopolysaccharide (from E. coli serotype 0:111: B4) per 20 g of body weight. 90 minutes later, for each experimental setting blood is taken of part of the population by cardiac puncture in citrate buffer for evaluation of cytokine and coagulation factor levels. Plasma is obtained by centrifugation for 5 minutes at 5,000 rpm.

The survival of the remaining mice is followed for one week.

The extent to which the fibrinolytic pathway is by a lipopolysaccharide injection of 40 microgram per 20 g body weight is evaluated by measuring concentrations of the two main pathway inactivators, namely PAI-1 (Plasminogen activator inhibitor-I) and $\alpha_2$-antiplasmin, using a sandwich-type ELISA with two specific monoclonal antibodies directed towards different sites of the molecule under evaluation.

The evolution of fibrinogen plasma concentrations is used as a reading of its conversion into fibrin.

Determination of zymogen and activated protein C can be measured for example in accordance to Richards et al. (1990) Clin. Chem. 36, 1892-1896.

The present experiment allows the identification of a suitable antibody or mixture of antibodies in order to prevent the endotoxin related sepsis. Analogous experiments can be devised for other components, or conditions which lead to the upregulation of the inflammatory cytokines IL-6 and/or TNF-alpha.

Example 10

Production of Antigen Binding Fragment (Fab) of Native and Deglycosylated Krix-1

LCL- and CHO-KRIX-1 (0.5 mg/ml in PBS) was mixed with N-glycosidase-F (Roche Diagnostics Gmbh, Mannheim, Germany) at final concentration of 2 U/ml. The mixture was incubated at 37° C. during 72 hours under gentle stirring.

Fab fragments were produced by incubating LCL- and CHO-KRIX-1 (0.5 mg/ml) in phosphate buffer ($KH_2PO_4$ 0.039M, $Na_2HPO_4$ 0.068M, pH 7.0 with Cysteine (0.05 M), EDTA (1 mM) and papain (10 microgram/ml). After 3 h incubation at 37° C., the reaction was stopped by adding 0.075M Iodoacetamine. After 30 min at 20° C., the mixture was dialysed against phosphate buffered saline (PBS). Undigested antibodies were removed by adsorption on HiTrap Protein A (Pharmacia).

The inhibitory activity of native and deglycosylated KRIX-1 Fab was assessed in a Bethesda assay (Kasper et al. (1975), cited supra) and is shown in FIG. 13.

Example 11

Production and Characterization of KRIX-1 and KRIX-1Q scFv Fragment

Cloning of scFv-KRIX-1VLVH in *Pichia* Expression Vector

An scFv fragment of KRIX-1 was constructed by adding a linker sequence between the 3' end of the KRIX-1 light chain variable part (VL) and the 5'end of the heavy chain variable part (VH). This was obtained by PCR amplification of KRIX-1 light chain and heavy chains using the following primers:

For the light chain: forward primer 5'-gtatct ctcgag *aaaaga*GAAATTGTGT-TGACGCAGTCTC-CAGGC-3' [SEQ ID NO:17] corresponding to the 5' end of the KRIX-1 VL sequence (capital), and containing a XhoI restriction site (underlined) and a KEX1 sequence (bold italic); reverse primer 5'-cgccagagccacctccgc-ctgaaccgcctc-caccTCGTTTGATCTCCACCTTGGTC [SEQ ID NO:18] corresponding to the 3' end of the KRIX-1 Jk sequence (capital), and containing a part of the linker sequence (italic)

For the heavy chain: forward primer 5'-caggcggaggtg-gctctggcggtg-gcggatcgCAGGTMCAGCTGGTG-CAGTCTGGG-3' (SEQ ID NO:19) corresponding to the 5' end of the KRIX-1 VH sequence (capital), and containing a part of the linker sequence (italic); reverse primer 5'-gatc tctagaTGAGGAGACGGTGACCAGGGTTCC [SEQ ID NO:20] corresponding to the 3' end of the KRIX-1 JH sequence (capitals), and containing a XbaI restriction site (underlined)

The PCR products were annealed and a second PCR was performed using the forward primer for the light chain (SEQ ID NO:17) and the reverse primer for the heavy chain (SEQ ID NO: 20). The resulting scFv-KRIX-1VLVH was cloned into the pPICZalphaC expression vector (Invitrogen, Merelbeke, Belgium)

Cloning of scFv-KRIX-1VLVH with His(6)tag in *Pichia* Expression Vector

A SalI restriction site was added to the scFv-KRIX-1VLVH sequence in order to clone it in frame with the His(6) sequence included in the pPICZalphaC expression vector (Invitrogen; Merelbeke; Belgium). This was obtained by PCR using the forward primer 5'-gtatctctcgag *aaaaga*GAAAT-TGTGTTGACGCAGTC-TCCAGGC-3' (SEQ ID NO:21) corresponding to the 5' end of the KRIX-1 VL sequence (capital), and containing a XhoI restriction site (underlined) and a KEX1 sequence (bold italic); and the reverse primer 5'-catggtcgacTGAGGAG-ACGGTGACCAGGGTTCCC CGGCC-3' (SEQ ID NO:22) corresponding to the 3' end of the KRIX-1 heavy chain JH sequence (capital), and containing a SalI restriction site (underlined).

The final pPICZalphaC-scFv-KRIX-1VLVH(His) vector was used to transform X33 cells for scFv production. The supernatant was tested to demonstrate the presence of a functional scFv fragment.

The scFv fragment was purified using the HisTrap Kit (Amersham Pharmacia Biotech, Uppsala, Sweden). After concentration the scFvKRIX-1VLVH(His) was tested in a FVIII chromogenic assay to evaluate the ability of the scFvKRIX-1VLVH(His) to inhibit FVIII activity. The FVIII inhibitory capacity was evaluated in a Besthesda assay according to the method in example 1 and is shown in FIG. 14.

Cloning of scFv-KRIX-1VLVHQ with His(6)tag in *Pichia* Expression Vector

The scFv-KRIX-1VLVHQ(His) was produced by site directed mutagenesis on the pPICZalphaC-scFv-KRIX-1VLVH(His) resulting in a single amino acid change in the heavy chain replacing Asn47 by a glutamine in order to disrupt the N-linked glycosylation site at Asn47-Thr49

This was obtained using the Site Directed Mutagenesis Kit (Stratagene, La Jolla, Calif.) in combination with the following specific PCR primers:

Forward primer: 5'-CCTGCAAGACCTCTGGAT AC cA a TTCACCG-GCTACTCTGCTTCTGG-3' (SEQ ID NO: 23) corresponding to nt 119 to 164 of the KRIX-1 Heavy chain sequence (capital) containing two altered nucleotides (a to c and c to a; bold italic).

Reverse primer: 5'-CCAGAAGCAGAGTAGCCGGT GAA tT gGTATC-CAGAGGTCTTGCAGG-3' (SEQ ID NO: 24) corresponding to nt 119 to 164 of the KRIX-1 Heavy chain sequence (capital) containing two altered nucleotides (g to t and t to g; bold italic).

The full length sequence of scFv-KRIX-1VLVHQ with His(6)tag is described in SEQ ID NO: 25 and 26.

Cloning of scFv-KRIX-1VLVH and scFvKRIX-1VLVHQ (His) with His(6)tag in a CHO Expression Vector The KRIX-1 light chain leader sequence was introduced into pPICZ C-scFv-KRIX-1VLVH(His) and pPICZ C-scFv-KRIX-1VLVHQ(His) by cloning of a HindIII/PstI restriction fragment of pCR4-KRIX-1L containing the leader sequence into HindIII/PstI digested pPICZ C-scFv-KRIX-1VLVH and pPICZ C-KRIX-1VLVHQ respectively. The resulting scFv sequence was adapted for cloning and expression purposes by PCR using the following specific primers:

Forward primer: 5'-cccaagctt gccgc caccATGGAAAC-CCCAGCKCA-GCTTC-3' (SEQ ID NO:27) corresponding to the 5' end of the KRIX-1 Light chain sequence (capital), and containing a HindIII site (underlined) and a Kozak sequence (bold italic).

Reverse primer: 5'-ccggaattc tcaatgatgatgatgatgatgT-GAGGAGACGGTGA-CCAGGGTTCC-3' (SEQ ID NO:28) corresponding to the 3' end of the KRIX-1 heavy chain JH sequence (capital), and containing a EcoRI site (underlined), a stop signal sequence (bold italic) and a His(6)tag sequence (italic)

The resulting PCR products were cloned into the pGEM-T-Easy vector (Promega; Leiden, Netherlands). After sequence verification the scFvKRIX-1VLVH(His) and scFv-KRIX-1VLVHQ(His) were cloned into the pEE14.4 vector (Lonza Biologics, Portsmouth, N.H.). The resulting vector was linearised with SalI before transfection.

The linearised vector was used for stable transfection of CKO-K1 cells using the FuGENE6 transfection reagent (Roche, Brussels, Belgium) according to the manufacturer's instructions. The transfected cells were cultured in glutamine-free DMEM (JRH Biosciences, Lenexa, Kans.) supplemented with FBS 10%, GS Supplement (JRH Biosciences, Lenexa, Kans.) and 50 μM L-Methionine Sulfoximine (MSX) (Sigma-Aldrich, Bornem, Belgium) for selection.

The best producers were adapted to growth in serum-free medium (EX-CELL 302 serum-free medium w/o L-Glutamine, JRH Biosciences, Lenexa, Kans.)—supplemented with GS Supplement and MSX in the respective concentration—by step-wise reduction of the FBS to 0%.

The supernatants were assayed for production of scFv-KRIX-1VLVH(His) and scFv-KRIX-1VLVHQ(His) in a FVIII chromogenic assay as described in example. The FVIII inhibitory capacity of the culture supernatant is shown in FIG. 15.

Example 12

Competition Between the Human Monoclonal Antibody RHD5 and KRIX-1

The human lymphoblastoid cell line RHD5 was derived by immortalisation of B lymphocytes from a patient who developed an autoimmune response to FVIII, according to described procedure (Jacquemin et al. (1998), Blood 92, 496-506). Briefly, $10^7$ peripheral blood mononuclear cells were resuspended in 2 ml culture medium and incubated for 2 hours at 37° C. with 200 μL Epstein-Barr virus supernatant (B95-8 strain). Cells were then seeded at 5,000 cells/well in 96-well microtiter plates (Nunc) containing feeder cells (3T6-TRAP cells irradiated with 7,000 rads). One hundred fifty microliters of culture supernatant was replaced every week by fresh culture medium. After 6 weeks, culture supernatant were tested in enzyme-linked immunosorbent assay for the presence of anti-FVIII antibodies. Positive cell line were transferred to 24-well plates and immediately cloned at 60 cells per 96-well plate without feeder cells. One clone, producing an antibody called RHD5, was selected.

This cell line producing the monoclonal antibody RHD5 was deposited with the BCCM/LMBP (Belgian Co-ordinated Collections of Microorganisms/Plasmid Collection) Laboratorium voor Moleculaire Biologie, University of Ghent, Technologiepark 927, B-9052 Zwijnaarde, Belgium in Jul. 30, 2004, with the D. Collen Research Foundation (Onderwijs & navorsing, Campus Gasthuisberg, Herestraat 49, B-3000 Leuven, Belgium) as depositor (accession number LMBP 6165CB).

The sequencing of the rearranged immunoglobulin genes coding for RHD5 was performed as described in Jacquemin et al, Blood 1998, cited supra.

The nucleotide and amino acid sequences of the variable regions of RHD5 heavy and light chain are listed in SEQ ID 29 to 32.

The antibody present in the culture supernatant was purified by adsorption on HiTRAP protein A (Pharmacia).

The inhibitory activity of native and deglycosylated KRIX-1 was assessed in a Bethesda assay (Kasper et al. (1975), cited supra) as described in example 1. RHD5 inhibited only partially FVIII activity up to the highest concentration tested. In a Bethesda assay performed by mixing one volume of antibody at 200 microgram/ml or of control buffer with one volume of plasma, the residual FVIII levels were 7.0±0.2 and 251.9±18.8 ng/ml, respectively (mean±SD of triplicates). The inhibition of FVIII activity reached at a final concentration of RHD5 of 100 microgram/ml was therefore 97%. Similarly, in a Bethesda assay performed by mixing one volume of antibody at 200 microgram/ml or of control buffer with one volume of full length recombinant FVIII (Recombinate$^R$, Baxter), the residual FVIII levels were 8.0±0.2 and 399.7±18.8 ng/ml, respectively (mean±SD of triplicates). The inhibition of FVIII activity reached at a final concentration of RHD5 of 100 microgram/ml was therefore 98%.

The ability of KRIX-1 to compete with RHD5 for FVIII binding was tested in ELISA. Polystyre microtitration plate were incubated overnight at 4° C. with 50 μL RHD5 at 2 microgram/ml in phosphate buffered saline (PBS). The plates were washed 4 times with PBS-Tween. Biotinylated recombinant FVIII (0.5 microgram/ml) in Tris-BSA-Tween was mixed with RHD5 or Krix-1 at various concentrations before addition to RHD5 coated plates.

After a two hours incubation period at 4° C., the plates were washed 4 times and bound biotinylated FVIII was detected by addition of avidine peroxidase (Sigma) at 1 microgram/ml. After 30 min at RT, the plates were washed again and supplemented with 100 µL OPD. The resulting OD was read at 490 nm in a Emax Microplate Reader (Molecular Devices, Menlo Park, Calif.).

Biotinylated FVIII used in the above experiment was prepared by incubating recombinant FVIII (100 microgram/ml) dialysed in Hepes buffer (Hepes10 mM, NaCl 0.15 M, CaCl2 10 mM, pH 8.5) with sulfo-NHS-LC-biotin (Pierce) at 1 microgram/ml for 2 hours at RT. The preparation was then dialysed against Hepes buffer and stored and −80° C.

As shown in FIG. 16, Krix-1 was able to completely prevent FVIII binding to RHD5. This competition between Krix-1 and RHD5 shows that mixing the two antibodies in different ratios will allow the production of antibody mixtures with inhibitory activity ranging between the inhibitory activity achieved with CHO-Krix-1 (85%) and that achieved with RHD5 (97-98%), similarly to the different inhibitory activities achieved by mixing Krix-1 and Krix-1Q in example 2. Similarly, mixing RHD5 and KRIX-1Q is predicted to allow the production of antibody mixtures with a very broad range of inhibitory activities ranging from 45% to 98%. It can also be predicted that mixing Fab fragment of KRIX-1Q with RHD5 should allow to produce an even broader range of inhibitory mixtures ranging from 20% to 98%.

Example 13

Identification of Alternative Inhibitory Antibodies to FVIII

The present example describes methods identify, starting from a first inhibitory antibody such as Krix-1, an additional second antibody can be identified, based on the fact that it competes with binding of such first inhibitory antibody such Krix-1. Preferably, the antibody identified in this way is inhibitory, and moreover has a plateau effect (partial inhibitory at molar excess (a 5, 10, 20, 50, or even 100-fold molar excess over FVIII). The procedure described below can be performed similarly using RHD5 in stead of Krix-1.

This is achieved using for example an assay wherein labelled Krix-1 (radioactive labelled or labelled with biotin or with a chromophoric group) is bound to Factor VIII. High numbers of uncharacterised antibodies are screened for their capacity to disrupt the binding of Krix-1 to FVIII.

Alternatively the uncharacterised antibodies are first incubated with FVIII insolubilised on microtiter plates, whereafter labelled Krix-1 is added and assayed for its binding to FVIII. Alternatively, Krix-1 and the second antibody are mixed together before assaying the residual binding of Krix-1 to FVIII.

Krix-1 being used in these assays can be glycosylated, partially glycosylated or completely deglylosylated (extensive enzymatic treatment or site directed mutagenesis at essential positions in the glycosylation consensus sequence). Krix-1 being used in these assays can be intact, a F(ab)2 fragment, a F(ab) fragment, a scFvscFv fragment or another fragment of Krix-1 with the capacity to bind to the C1 domain of FVIII.

Using these assays, antibodies which impair the binding of Krix-1 to the C1 domain of FVIII can be identified. This impairment can be achieved by an antibody directed to the same epitope in the C1 domain as for Krix-1, by an antibody directed to another epitope that the one of Krix-1 in the C1 domain, or by antibody with an epitope outside the C1 domain but which sterically competes with the binding of Krix-1 antibody to its epitope in the C1 domain. In this context, an assay wherein an intact Krix-1 is used which is heavily glycosylated is more likely to generate Krix-1 interfering antibodies than a fragment of Krix1 or deglycosylated Krix-1.

The screening for antibodies can for example be initiated by screening in first instance a scFv library for scFv fragments that bind to human FVIII and more particularly bind to the C1 domain of Factor VIII. For this technique, antibody fragments have been displayed on the surface of filamentous phage that encode the antibody genes (Hoogenboom and Winter (1992) *J Mol Biol.* 227, 381-388; Vaughan et al. (1996) *Nat. Biotechnol.* 14, 309-314; Tomlinson et al. (1992) *Hum Mol Genet.* 3, 853-860; Nissim et al. (1994) *EMBO J.* 13, 692-698; Griffiths et al. (1994) *EMBO J.* 12, 725-734). Variable heavy chain (VH) and variable light chain (VL) immunoglobulin libraries have been developed in phages. These phages can be selected by panning with antibody. The encoded antibody fragments can then be secreted as soluble fragments from infected bacteria. This display of antibodies on phages and the selection with antigen mimics immune selection and can be used to make antibodies without immunization starting from a single library of phages (Hoogenboom and Winter (1992) *J Mol Biol.* 227, 381-388). A human synthetic VH and VscFv library was made by recloning the heavy and light chain variable regions from the lox library vectors, wherein the heavy and light chain V-genes were shuffled at random and cloned for display as single-chain Fv (scFv) fragments on the surface of filamentous phage (Griffiths et al. (1994) *EMBO J.* 12, 725-34) [Centre for Protein Engineering of Dr. G. Winter, LMB-MRC, Cambridge, UK] into the phagemid vector pHEN2.

Using such library, antibody fragments can be identified which compete with the binding of an antibody such as Krix-1 to FVII. Hereafter, these fragments can be screened for their affinity of binding to FVIII and subsequently for their capacity of inhibiting FVIII activity and for the presence of a plateau effect of inhibiting FVIII activity at a molar excess. Considering the size of the fragments, it is envisaged that enlarging the size of these fragments, by cloning these scFv fragments into a complete antibody, will result in an increased inhibitory activity. In accordance with the invention, the glycosylation of the newly identified scFv fragment and the corresponding antibody can also be modified using the techniques described in the present invention.

Alternatively, antibodies isolated from hemophilia patent or more generally any existing antibody can be assayed for its capacity to compete with an antibody such as Krix-1 or RHD5.

Antibodies or fragments which have been obtained using the above mentioned assay are tested for their inhibitory effect on FVIII activity and/or for their capacity to disrupt a complex between FVIII and e.g. vWF. Further, inhibitory antibodies or fragments are then screened for the presence of partial FVIII inhibition at physiological excess ("plateau effect").

Any second antibody which competes with Krix-1 binding can be used in mixtures with native Krix-1 or a native fragment of Krix-1, or Krix-1 or a fragment with modified glycosylation to obtain a FVIII activity inhibition being lower than Krix-1 if the second antibody has no inhibitory activity, or has a plateau effect which is lower than that of Krix-1. Alternatively, mixtures between native Krix-1 or a native fragment of Krix-1, or Krix-1 or a fragment with modified glycosylation and a second antibody result in FVIII activity inhibition being higher than Krix-1 or its fragment if the second antibody has a fully inhibitory activity, or has a plateau effect which is higher than that of Krix-1. Equally, in these mixtures the second antibody can be replaced by a fragment of a second antibody such as a F(ab)2, Fab, scFv or another fragment, or can have a modified glycosylation in the variable region, if occurring on such second antibody.

We claim:

1. An isolated inhibitory antibody against factor VIII or a fragment thereof comprising the immunoglobulin variable light chain CDR1, CDR2, and CDR3 regions depicted in SEQ ID NO:36, SEQ ID NO:37, and SEQ ID NO:38 respectively, and comprising the immunoglobulin variable heavy chain CDR1, CDR2, and CDR3 regions depicted in SEQ ID NO:33, SEQ ID NO:34, and SEQ ID NO:35 respectively, wherein the glycosylation of said antibody or fragment thereof on the glycosylation site at amino acid positions 3 to 5 of the CDR1 region of the variable heavy chain is decreased relative to the glycosylation of the same antibody as produced by the EBV-immortalized human B cell line KRIX1 deposited with the Belgian Coordinated Collections of Micro-organisms under accession number LMBP 5089CB.

2. The isolated antibody according to claim 1 wherein said decreased glycosylation results from producing said antibody in CHO cells.

3. A pharmaceutical composition comprising the antibody according to claim 1.

* * * * *